United States Patent
Lee

(10) Patent No.: US 6,998,141 B2
(45) Date of Patent: Feb. 14, 2006

(54) MEDICATION COMBINATION FOR HEPATOMA AND PANCREATIC CANCER AND PREPARATION PROTOCOL

(76) Inventor: Chien-Yung Lee, 2F, No. 60, Shouhua Rd., Gangshan Jen, Kaohsiung Hsien (TW)

(*) Notice: Subject to any disclaimer, the term of this patent is extended or adjusted under 35 U.S.C. 154(b) by 494 days.

(21) Appl. No.: 10/252,123

(22) Filed: Sep. 23, 2002

(65) Prior Publication Data

US 2004/0013748 A1 Jan. 22, 2004

(30) Foreign Application Priority Data

Jun. 26, 2002 (TW) .............................. 02124451 A

(51) Int. Cl.
- *A61K 35/78* (2006.01)
- *A61K 47/00* (2006.01)
- *A61K 9/00* (2006.01)
- *A23K 1/17* (2006.01)

(52) U.S. Cl. ...................... 424/725; 424/400; 424/439; 424/442

(58) Field of Classification Search ................ 424/725, 424/400, 439, 442
See application file for complete search history.

(56) References Cited

*Primary Examiner*—Susan Coe
*Assistant Examiner*—Randall Winston
(74) *Attorney, Agent, or Firm*—Browdy and Neimark, PLLC

(57) ABSTRACT

This invention discloses a medication combination, consisting of Baizhu, Danggui, Hanxincao, Huotanmucao, Ainaxiang, Shuodiao, Malan, Ludou, Canger, Daqinggen, Banbianlian, Xingren, Nuzhenzi, Qianhu, Jiatonghao, Yinchenhao, Yujin, Zhishi, Banxia, and Fuling for treating hepatoma and pancreatic cancer, modifies the conventional extraction procedure and is characterized by the inclusion of Poria, which possesses an anti-tumor ability, as the excipient. This medication combination is based on a novel and continuous theory for cancer therapy and traditional Chinese medicine theories. It has made use of nature and characteristics of those abovementioned medications to lead and change the environments for cancer growth inside the patients' bodies, and then to result in the discomfort and revulsion of cancer cells in such environments. In another word, this medication combination alters the cancer environment via pharmacology and exerts a certain extent of anti-tumor effect on the primary or metastatic hepatoma and pancreatic cancer.

4 Claims, No Drawings

MEDICATION COMBINATION FOR HEPATOMA AND PANCREATIC CANCER AND PREPARATION PROTOCOL

FIELD OF THE INVENTION

The present invention relates to a medication combination, consisting of Baizhu, Danggui, Hanxincao, Huotanmucao, Ainaxiang, Shuodiao, Malan, Ludou, Canger, Daqinggen, Banbianlian, Xingren, Nuzhenzi, Qianhu, Jiatonghao, Yinchenhao, Yujin, Zhishi, Banxia, and Fuling for treating hepatoma and pancreatic cancer.

BACKGROUND OF THE INVENTION

The progression of cancer therapy has been idled in the perplexity of anti-tumor with lack of effective medication for internal use. The efficiencies of expedient treatments, such as thrombosis, radiation therapy, and chemotherapy were limited. Meanwhile, those extreme, harsh and complicated therapy courses have made patients suffered from horrible pains. With a doubtful presupposition of killing cancer cells, the neglect on the pathological deterioration of other areas or tissues has led to hideous hypersensitive reactions or dosage dependency.

Unfortunately, cancer researches have been restrained inside a fixed model. The idea of anticancer being equal to cancer curing has been wrongly believed. All beautiful and attractive theories should not be ensured before accomplishing and should be treated as hypothesis. Inapplicable or undesirable presumed theories must be with flaws or doubts. Therefore, it is urgently necessary to break this fixed model and present a novel idea, theory or remedy. Anticancer research in China has reached a certain level and more than 300 medications have been proven valuable through animal tests for anticancer, however, none of these medications could effectively treat cancers if used solely. The ultimate cause should be investigated (please refer to Chapter 12 in the new way to treat cancer in the $21^{th}$ century, a book of this Inventor).

With the advantages of ample resources of Chinese medicine and policy encourage, anticancer and cancer curing business in this countries have progressed enormously with many publications on highly effective medications, which are however not been applied by the industry. This may be due to the conventional descriptions on "discrimination of symptoms and discussion of treatments" were not widely understood and accepted.

SUMMARY OF THE INVENTION

The main aim of this invention is to present a medication combination for treating hepatoma and pancreatic cancer and to expand a new treatment of Chinese medicines by novel and continuous theories and remedies. Based on implication of "discrimination of symptoms and discussion of treatments", precise and simple description of "six elements", which is the composition of organism, will be widely accepted and blended into the medical trend to create a new way of Chinese medicines to cure cancers.

Another aim of this invention is to present a medication combination for treating hepatoma and pancreatic cancer with a convenient way of internal use, which could enhance the efficiency of curing cancer, reduce the medical cost and therefore, benefit overall cancer patients.

To achieve the abovementioned goals, the medication combination for treating hepatoma and pancreatic cancer comprises:

(a) one or more medications selected from the group consisting of Fuling, Baizhu and Danggui for improving the function of pancreas and connections to other organs;

(b) one or more medications selected from the group consisting of Hanxincao, Huotanmucao, Ainaxiang and Shuodiao fro eliminating barriers in permeability of the portal vein, liver and pancreas to decrease the pressure of the portal vein;

(c) one or more medications selected from the group consisting of Malan, Ludou, Canger, Daqinggen, Banbianlian, Xingren and Nuzhenzi for enhancing the defensive function, lymphatic circulation, and immunity, and (d) one or more medications selected from the group consisting of Qianhu, Jiatonghao, Yinchenhao, Yujin, Zhishi and Banxia for pathological amendments specific for hepatoma and pancreatic cancer.

The novel theory, pharmacology, pathology of hepatoma and pancreatic cancer, clinical trials and statistics of efficiency are described as follows.

DETAIL DESCRIPTION OF THE INVENTION

The Novel Theory

The traditional theories of anticancer could not break through the bottleneck of cancer curing nor enhance the efficiency. Therefore, this inventor has created continuous theories for curing cancer and to achieve the expected efficiency. To simply describe, the novel theories are sequentially "A theory on birth, growth, aging and death of a creature", "A theory on the developing environment of a creature", "A theory on surrounding pathology of cancer", and "A theory on variation of six elements in the cancer", which is a part of "A theory on six elements". These four theories are extension and innovation of viewpoints on Chinese medicine from all past dynasties. They are uniquely integrated with bio-philosophy and apply the characters of the ancient philosopher, Lao-Tzu (about 580 B.C.) to generate a precise and acceptable description.

Firstly in "A theory on birth, growth, aging and death of a creature" (please refer to Chapter 2 in the new way to treat cancer in the $21^{th}$ century, a book of this Inventor), it was stated that all normal creatures must go through stages of birth (reproduction), growth, aging and weakness, and death. Since cancer cells are organisms, they are not exceptional and also have limitations of weakness and death. If there is any method or medication able to alleviate the production and growth of cancer cells as well as promote the weakness and death, cancer will be curable without "resistance, killing, and extermination".

To achieve assumed targets abovementioned, the real situation, internal environment and causes for alternation for birth, growth, aging and death have to be understood in advance. Therefore, "A theory on the developing environment of a creature" (please refer to Chapter 1 in the new way to treat cancer in the $21^{th}$ century, a book of this Inventor) can be apprehended to have a certain extent of environmental adaptation, that is, to reproduce and grow in a nice environment but weak and die in a repulsive environment. Among these, the most valuable finding is that the formation of environment is totally depended on the nature, status and characteristics of materials. The normal human body is not a suitable environment for growth and activity of cancer cells. However, after a long-term influence by the nature, characteristic and direction of abnormal materials, the patient's body has become a suitable environment for cancer cells to survive, reproduce and growth, that is, a paradise for cancer cells. This is the philosophy of cancer formation. It should be noted that medication is one kind of material. The nature, characteristic and direction of medication are equal to the texture, smell, taste, and ingredient, which are overall pharmacology. By choosing the best material and applying its nature, characteristic and direction, another environment, which cancer cells are difficult to adapt and repulsive, could be formed in the patient's body to retard the reproduction and growth as well as to promote the weakness and death of cancer cells and therefore, cancers could be easily cured.

A constitution with an environment, which is suitable for the reproduction, survive and growth of cancer cells, is different from that of normal and therefore been nominated as "an unique constitution of cancer". After thoroughly examinations and experiments, it has been understood basically to form "A theory on surrounding pathology of cancer" (please refer to Chapter 3 and p 111 of appendix 4 in the new way to treat cancer in the $21^{th}$ century, a book of this Inventor). Such fixed surrounding pathology, present in all types of cancers, have 3 abnormal pathological findings, including reduced function of pancreas with poor connection to other organs, poor permeability of hepatic circulation and pancreas with generally high pressure, and malfunction of defensive tissues and lymphatic circulation. The environment with such 3 pathological findings is a suitable environment for cancer cells.

The conventional theories such as "discrimination of symptoms and discussion of treatments", "wind, cold, hot, dry, anger six wicked elements", "negative and positive, false or true, outside and inside", are not commonly recognized by ordinary people except scholars of Chinese medicine. These outstanding practical theories are indispensable in Chinese medicine, therefore, the inventor has derived "A theory on variation of six elements in the cancer" from "A theory on six elements" to make a concise and easy description. This philosophic theory, originally about the constitution of creatures, can be applied in the treatment and even in the cancer curing.

Similar to other creatures, the elements for constituting the cancer environment are energy (one), space (sky), essence (earth), humidity (water), air (wind), and temperature (fire). These are "six elements" for creature constitution. "Energy" refers the natural vitality, "space" refers the size of interspace, "essence" refers the real substance, "humidity" refers the amount of liquid water, "air" refers the ingredient in the air and "temperature" refers cold or hot. These six elements can be present by the conditions of inside, outside, sites, organs, and tissues of human body. By using the circulation of blood inside the human body as an example to describe the essence and combination of these six elements, the vascular wall is the "essence", vascular cavity or places that blood can permeate is the "space", the blood flow is based on "energy", and blood is a combination of elements, including humidity (water), essence (blood cells), air (oxygen and carbon dioxide), temperature (cold and hot).

Inside the human body, the key point for condition observation on tissues is the "alternation", that is different from the ordinary and normal, which is pathological finding, for examples, local inflammation, redness and swelling, hyperemia, pain, higher temperature of hepatic lobes, malmetabolism of water and higher temperature in pancreas, less movement in the intestines and complication in urination and excretion. All pathological variations could be traced to the root by description of six elements. As for the diagnosis and observation, "observation, listen, smell, question, and feeling the pulse" of Chinese medicine and X ray, scan, and all kinds of tests, as well as patient history and experiences can be employed. This invention is based on surrounding pathology and real condition of variation in these six elements to choose a best medication combination for treating hepatoma and pancreatic cancer. The nature, characteristic and direction of this combination will form an environment, which cancer cells hate to achieve the objective that cancer cells stop growing and then die.

There are indeed a few mistakes and confusion in the conventional theories of Chinese medicine. Spleen referred in Chinese medicine, not as the spleen in modern anatomy, is as pancreas in this description (please refer to "spleen is not the spleen" in appendix 2, in the book writing by the inventor). In addition, fire should be referred as temperature, instead of heat, and therefore, can be distinguished as cold and hot. Water is referred as humidity and classified as dry and wet. All materials or differentiation of materials have both positive and negative directions. The abovementioned is only for the correctness of this description.

As for the close relationships between environment and cancers, a few findings have been revealed by numerous studies. However, due to the limitation of certain objective conditions, these findings could not be further investigated. For examples, it was found that cancer cells are prone to anaerobic metabolism. The product of this metabolism, lactic acid, will contribute to form an acidic environment and therefore, is beneficial to increase the activity of $\beta$-glycosidase. This will promote the degradation of amygdalin into hydrocyanic acid and benzaldehyde and then to exert more powerful action against cancer.

In addition, as indicated in "Pharmacology of Chinese medicine" of Yi-Kui Lee, dilute alcohol- or water-extracts of banxia can significantly inhibit the growth of HCA, S180 and HeLa cells in animal models. In the aspect of mechanisms of such inhibition, as referred in "Pharmacology and clinical application of Chinese medicine" of Shou-Yi Liu, Banxia is able to significantly reduce the secretion of stomach acid, reduce the acidity of free acid and total acid and also inhibit the activity of pepsin.

From abovementioned studies, it was found that characteristics including anaerobic degradation, acidic tendency, higher acidity in free acid and total acid are present in the experimental environment resistant to cancer. The inhibitory activity and resistance to cancer of amygdalin, dilute alcohol- or water-extracts of banxia is based on the utilization of known environment or alteration of original environment to generate a cause and effect relationship, which is also the pioneer viewpoint of the theory of this invention. However, the human-cancer environment formed by persistent material situation is not that simple.

Pathological Anatomy

Types of primary hepatoma include a big and developing type with a single cancerous nodule (grain in liver), a nodal type with dispersed cancer nodules of various sizes, a fine type with numerous of micro nodules infiltrating the whole liver, a intrahepatic bile duct type with tumors inside bile duct. In the case of secondary hepatoma, numerous nodules of various sizes result in enlargement of liver with a hard and gray-yellowish cross-section. After maturation, necrosis occurs in the middle of tumor tissue and a hemispheric bulge occurs in the near surface with a tumor navel at the apex.

Over half of pancreatic cancers occur at hepatopancreticae, mostly at the epithelium of pancreas duct and sometimes at the epithelium of a lobule. Scirrhosity is the most common and followed in sequential by medullary cancer and column epithelial cancer. Glioma is the less.

Symptoms

The main complaint of hepatoma, in general, is the local swelling, hard and pain of right costal and liver region, stomach and abdomen. Based on the severity, the right costal and liver area may be stretched tight, swollen, hard and even obviously enlarged and harden. Such symptoms may be extended to the pit of the stomach or right abdomen. Various sizes of nodules, which are hard and tender, are touchable at the surface or bottom of liver. If severe, swollen bulk can be observed obviously and hard as rock. The severity of pain can be distinguished as tender, occasional, and dull, which may progress to become stuffy, persistent or sharp pain. Due to the tumor site, in addition, pain can be at both sides of costa and back and may extend to the right shoulder and arm. Distention of Stomach or abdomen without reasons may be due to the high pressure of hepatic circulation, which is the result of pancreatic hypofunction and poor permeability of liver. These may also induce the enlargement of spleen, bleeding of digestive tracts in the side circulation, dilation of subcutaneous veins, production of ascites, edema of the shin, inflammation of lymph nodes in clavicle, intermittent fever. The blood related symptoms include erythropenia, transformation and leukocytosis. In addition, symptoms also include darken, dryness, and jaundice of skin.

The main symptoms of pancreatic cancer include tenderness or persistent pain at the tip of stomach, pain and swelling at the right costal region, shoulder and arm, acid or salty saliva generated on the surface of tongue, which is a characteristic of pancreas condition. Tumors at the epithelium of pancreas lobe are more persistent and progressive, and could cause a person pale and skinny without appetite in a short period. Persistent jaundice commonly occurred with pancreatic cancer, as well as fever from bacterial infection. Most of survivors are complicated with symptoms of hepatoma.

Formulation

This medicine combination, for treating hepatoma and pancreatic cancer, consists of following powder, concentrated and extracted, at a fixed ratio. Fuling powder, included in each preparation, is employed to be the excipient.

| Fuling | Concentrated excipient |
|---|---|
| Baizhu | 3–7% |
| Danggui | 3–7% |
| Hanxincao | 4–8% |
| Huotanmucao | 2–6% |
| Ainaxiang | 2–6% |
| Shuodiao | 5–9% |
| Malan | 6–10% |
| Ludou | 5–9% |
| Canger | 3–7% |
| Daqinggen | 4–8% |
| Banbianlian | 3–7% |
| Xingren | 2–6% |
| Nuzhenzi | 4–8% |
| Qianhu | 3–7% |
| Jiatonghao | 3–7% |
| Yinchenhao | 3–7% |
| Yujin | 3–7% |
| Zhishi | 2–6% |
| Banxia | 2–6% |
| Total | |

These ingredients in each medication can be included or not included, as well as be augmented or subtracted, based on the small pathological variation among patients. The best configuration is 5% of Baizhu, 5% of Danggui, 6% of Hanxincao, 4% of Huotanmucao, 4% of Ainaxiang, 7% of Shuodiao, 8% of Malan, 7% of Ludou, 5% of Canger, 6% of Daqinggen, 5% of Banbianlian, 4% of Xingren, 6% of Nuzhenzi, 5% of Qianhu, 5% of Jiatonghao, 5% of Yinchenhao, 5% of Yujin, 5% of Zhishi, 4% of Banxia to make a total of 100%.

Pharmacological Description

Pharmacological description, as shown in pharmacological data sheet of each ingredient, is emphasized on improvement of 3 aspects in surrounding pathology, including improvement in the function of pancreas and connections to other organs, elimination of the barriers in permeability of the portal vein, liver and pancreas to decrease the pressure in the portal vein, enhancement in the defensive function, lymphatic circulation, and immunity, as well as pathological amendments specific for hepatoma and pancreatic cancer. Other compatible cancer treatments are also described.

The following descriptions are aimed on the main pathological symptoms of hepatoma and pancreatic cancer, as well as the pharmacology.

The pathology of swelling and pain in the major symptoms of hepatoma and pancreatic cancer is not exactly the same as others. After careful observation and examination, swelling and pain of hepatoma and pancreatic cancer are resulted from several causes. First, due to the stronger nerve responses in the local tissues of these cancers, such as liver ligament, connective tissue, the constrictor, and hepatopancreticae, tiny stimulations could induce contractions of these local tissues and then result in a poor transmission. As a consequence, the severity and frequency of swelling and pain are increased. For this reason, medication with the function of relaxing, smoothing and swaying the nerve is needed. Secondly, most of liver and pancreas mass are occupied by hepatic sinus and pancreas follicles, inside which fluid continuously flow through. A higher temperature of these vessels will be prone to induce inflammatory pathology of vessel walls. Once such condition occurs, the transmission will be hinder to induce swelling and pain. Thus, medication with the function of lowering the temperature and nourishing is needed. Lastly, secretions of liver and pancreas are similarly via mastoids of duodenum. Due to the poor permeability of liver and hypofunction of pancreas, stomach acid secretion is imbalanced and too much mucus, that is phlegm or slayer, is produced in stomach and intestines. In the hepatopancreatic circulation, such mucus will obstacle the circulation to worsen or prolong the swelling and pain. Therefore, it is necessary to include medication with the function of diluting the viscousness.

In addition to regulation of the surrounding pathology, the pharmacology of medicine combination for treating hepatoma and pancreatic cancer has to focus carefully on the actual variation of six elements in patient's body. Furthermore, medications with functions of relaxing, smoothing and swaying the nerve, lowering the temperature, and diluting the viscousness should be used in coordination. That is, to generate a repulsive environment, which is not suitable for survival of cancer cells, by utilization of medications with functions of relaxing, smoothing and swaying the nerve, lowering the temperature, and diluting the viscousness in the combination. In addition, by altering the cancerous environment to make it back to normal to achieve the objective of cure.

In this description, conventional and general statements, including spleen augment and correction, regulation and nourishment, circulation stimulation and stasis dispersal, softening and dispersal of bulge, fever alleviation and detoxication, relieving depression and wetness, as well as practical essential pharmacology is also added. Each medication and corresponding pharmacology is described as follow.

1. Improvement in the function of pancreas and connections to other organs:

Fuling is used in the concentrated extract of this series of cancer treatment to substitute as the effective and modified excipient for the traditional starches of grains and yams and therefore, integrated into each medication. This ingredient, a nutrient supplement, is able to promote the pancreas function and immunity, stabilize the nerve system, regulate rhythm of the heart, enhance water metabolism in organisms, facilitate urination, enhance the immunity of mice of normal or with tumors, and augment the phagocytosis of macrophages. It also has positive effect on various cancers, including nasopharyngeal cancer, gastric cancer, and cervical cancer.

Baizhu is able to enhance the pancreas function, augment the physical strength and immunity, regulate the connection of pancreas with other organs, promote the water metabolism of organisms and tissues, and facilitate urination, as well as prevent gastric ulcers and intestine cramps, care for the liver and gallbladder, enhance the phagocytosis of reticular endothelium and macrophages, and resist the oxidization. As indicated in Chinese medicine of Shang-Shi (1988) by Jia-Tsai Sun et al., Baizhu can reduce both of proliferation of cancer cells and tumor invasion.

Danggui can supplement necessary nutrients and inorganic elements, harmonize the connection of pancreas with other organs, enhance the hematopoiesis and circulation, eliminate the thrombi in vessels and prevent thrombosis, as well as promote the conversion of lymphocytes with an auxiliary anti-tumor effect.

2. Elimination of the barriers in permeability of the portal vein, liver and pancreas to decrease the pressure of the portal vein:

Hanxincao is able to lower the higher temperature in liver and pancreas, promote blood circulation, eliminate the thrombi, bacteria, cancer cells in the portal vein, as well as reduce the pressure of the portal vein, prevent the regression in side circulation and stop the bleeding.

Huotanmucao is able to improve the water metabolism, lower the blood temperature and detoxification, as well as alleviate the tightness of vessels or tendon ligament, resist the infection of bacteria or hepatitis B virus, and lower the blood pressure. It can also improve the microcirculation of liver and pancreas to promote the permeability.

Ainaxiang is able to eliminate the pathogenic causes of abnormality in circulation or abnormal pressure in blood capillaries (relieve rheumatic pain), promote the water metabolism of local tissues or organs (amend the wetness), maintain the suitable intra-abdominal temperature, stop diarrhea, smooth the circulation (blood stream) and eliminate the toxin inside the body (detoxication), as well as eliminate those inappropriate or hazardous gas in lymphatic or blood vessels. As indicated by Fuijimoto et al., the growth of Yoshida sarcoma could be inhibited by 5–10 kg/ml of blumealactone A, B, C extracted from the leaves of Ainaxiang.

Shuodiao is able to eliminate the causes for abnormal pressure in vessels and capillaries (relieve rheumatic pain), abolish the hindrance of water metabolism in local tissues or organs (expel the wetness), relieve the pain, help urination, promote circulation to disperse thrombi, and preserve liver function, as well as preserve the normal blood pressure and water metabolism around the tumor tissues to alleviate sharp pain caused by cancer.

3. Enhancement in the defensive function, lymphatic circulation, and immunity:

Malan, with a stable capability of detoxication, is able to enhance defensive function, lower the higher temperature around cancer tissues, and increase the nutrient elements in the blood to eliminate symptoms including inflammation, hyperemia and swelling. An ingredient, indirubin, is capable of resisting the tumor formation and enhancing the phagocytosis of monocytes of mice and also has significant effect on the abnormality of cancer environment.

Ludou, a nutrient, is able to supplement consumed energy, lower the high temperature caused by drastic ingredients (supplementing pancreas and clarify illusory heat), and eliminate toxic materials inside body, especially in liver and kidney to promote urination (detoxication and urination). It can also reduce cholesterol, resist atherosclerosis, and significantly alleviate the damage to kidney and liver. As indicated by Han-Yuan Chen et al in the Academic Journal of First Medical University in 1989, the diet containing Ludou powder can reduce the number and mass of lung cancer and hepatoma induced by morphine and nitrous acid. The pharmacological effect of Ludouhuang, a preparation of Ludou and less nutritious, is even stronger, especially in the aspects of detoxication and reduction in inflammation, and has positive influence on the cancer surrounding.

Canger is able to eliminate the causes for abnormal pressure of vessels and capillaries, relieve the higher temperature inside body and skin (dispersal of wind and heat), remove toxins in defensive system and tissues, and kill germs and bugs (detoxication and eradication of bacteria), as well as eliminate the obstacles in lymphatic circulation, and treat leprosy and early stage of blood fluke infection.

Daqinggen is capable of relieving the body heat and high temperature on skin caused by lymphatic alteration and reducing the high temperature of blood, liver and pancreas to promote lymphatic permeability and normal circulation.

Banbianlian can penetrate lymphatic microcirculation in deep area of organs to activate the defensive function and neutralize the toxins and promote urination, secretion of bile and resistance to venom, as well as treat liver cirrhosis, ascites and various cancers.

Xingren, used as external medicine of skin cancer on knees in ancient time, can go deep into acidic environment of cancer to alter the condition. As indicated in Shansi Journal of Medicine by Su-Lian Zhao, muscular injection of amygdalin significantly promoted the mitosis and proliferation of spleen T lymphocytes in mice.

Nuzhenzi is able to supplement mild nutrients and trace inorganic elements to liver and kidney to activate immunity and amend the nature and circulation of lymphatic system.

4. Pathological amendments specific for hepatoma and pancreatic cancer:

Qianhu can regulate body temperature, guide the inappropriate air in the tissue (leading the air), dilute and expel viscous liquid (reducing phlegm and making expectoration easy), promote metabolisms in digestive and respiratory system (metabolism), as well as to aid other medications in the metabolisms in lung, stomach, liver and pancreas to renovate the air and nature.

Jiatonghao can eliminate drastic elements in blood, lower the higher temperature of liver, gallbladder and pleura, and smooth the local lymphatic circulation to rapidly alleviate local inflammation and pain of cancer tissues.

Yinchenhao is able to eliminate retained water and lower the higher temperature and also able to lead hazardous materials and elements out of liver and gallbladder to promote the smooth flow of intrahepatic bile duct. It was indicated by Jen-Sha Lo in Academic Journal of Fu-Jian Medical College that decoction of Yinchenhao could resist tumor growth and inhibit mutations. In Communication of He-Han Chinese Medicine Association, Chiang-Shiu et al., have shown that Yinchenhao can direct hinder the proliferation of cancer cells.

Yujin can relax the hepatic ligament to reduce pressure and make the secretion of pancreas and bile smooth. In addition, Yujin can protect liver and myocardium against damage and enhance the immunity.

Zhishi can stimulate smooth muscles of stomach and intestine to increase the electric frequency and therefore, promote the excretions of abnormal materials. It can also dilute those viscous liquid in the hepatopancreatic circulation for the smooth flow in intrahepatic bile duct.

Banxia is able to anesthetize the nerve for vomit to alleviate the hypersensitivity of upper digestive tracts (stop vomiting and backflow), reduce the gastric acid secretion to diminish abnormal acidity in the cancer environment, prevent overproduction of viscous liquid to eliminate local hindrance in circulation. It also exhibited significant inhibition on the growth of hepatoma, sarcoma, and cervical cancer in animal studies.

| Pharmacological Data of Medication | |
|---|---|
| No. 1 | |
| Name of Chinese herbal medicine | Fuling    The formal name    *Poria cocos* (schw.) WOLF. |
| Foundation | Page 1596 of Dictionary of Chinese Medicine and page 554 of Chinese material medica Book 1 (published by Shanghai Scientific and Technical Publishing Company) |
| The place of origin, harvest season, and portion | Fuling is produced in Hubei and Anhui and matured after being cultured for 8 to 10 months. The plant is stripped to check and should be harvested if the color of surface is brown. It should be dug out on a shiny day and, after removing the dirt and sand, covered with straw to make it sweat (water). After the surface wrinkling, the surface skin is stripped off and Fuling is dried. |
| Procedures for preparation and extraction | 1. Those heavy, hard, brown-skinned, fine striped, no crack, white and smooth at the cross-section, and strongly sticky Fuling are selected, stripped to remove the skin, immersed to be soften, dissected to be thin sections and dried.<br>2. Fuling of 50 kg is grounded, screened through a sieve of 120 and stored as powder. |
| Active ingredients | Containing β-Pachyman, about 93% of dried weight, Pachymicacid, 3β-Hydroxylanosta-7.9(11), 24-trien-21-oil acid and additionally, gelatin, chitosans, fatty acid, sitosterol, lecithin, glucose, adenosine, histidine, choline, β-Pachymanase, lipase, proteinases, as well as 0.23% of inorganic Ash and elements including Fe, Ca, Mg, K, Na, Ce, and P. |
| Original pharmacological action | Originally, it is used to augment the nutrient, promote the pancreas function and immunity, stabilize the nerve system, regulate rhythm of the heart, enhance water metabolism in organisms, and facilitate urination.<br>Currently, it is used to enhance the immunity of mice of normal or with tumors, augment the phagocytosis of macrophages, and positively effect on various cancers, including nasopharyngeal cancer, gastric cancer, and cervical cancer. |
| Pharmacological application and purpose | Used to augment the nutrient and promote the pancreas function, immunity and water metabolism. In this invention, Fuling is used as an excipient. All concentrated extracts, except those were not extracted and dried, are mixed with pure Fuling powder instead of the conventional edible starches of grains and yams. |
| No. 2 | |
| Name of Chinese herbal medicine | Baizhu    The formal name    *AtractyLodes Macrocephala* Koidz |
| Foundation | Page 670 of Dictionary of Chinese Medicine and page 715 of Chinese material medica Book 7 (published by Shanghai Scientific and Technical Publishing Company) |
| The place of origin, harvest season, and portion | Baizhu is produced in Zhejiang. After the dryness of the portion aboveground in November, roots were dug out and clean to remove any dirt and stems and then baked at 100□. Till the surface is hot, temperature was reduced to 65□ for 4–6 hours |

-continued

| | Pharmacological Data of Medication |
|---|---|
| | with one inversion. Those fibrous roots were removed while half dried and then baked again till 80% dryness. After 5–6 days of storage for softening the surface skin, they were baked till being thoroughly dry. |
| Procedures for preparation and extraction | 1. Baizhu of 4 kg is washed clean, sectioned, immersed in water for 3 hours and then decocted in two parts.<br>2. After heating to evaporate the moisture till 3 liters of concentrate remaining, Fuling of 1 kg is mixed into.<br>3. Desiccation at 60° C.<br>4. The product is grounded and screened through a sieve of 100 and stored as powder. |
| Active ingredients | Tens of various volatile oil, including atractylone, atractylenolide, 14-acetyl-12-Senecioyl-2E, 8Z, 10E atractylentriol, scopolamine, fructose, inulin, Mannan AM-3, which is functional in immunity, and tyrosine. |
| Original pharmacological action | Baizhu is able to enhance the pancreas function, augment the physical strength and immunity, regulate the connection of pancreas with other organs, promote the water metabolism of organisms and tissues, and facilitate urination.<br>It modern pharmacological action include prevent gastric ulcers and intestine cramps, care for the liver and gallbladder, enhance the phagocytosis of reticular endothelium and macrophages, and resist the oxidization. As indicated in Chinese medicine of Shang-Shi (1988) by Jia-Tsai Sun et al., Baizhu can reduce both of proliferation of cancer cells and tumor invasion. |
| Pharmacological application and purpose | To improve the pancreas function and immunity, regulate the connection of pancreas with other organs, care for the liver and gallbladder, and significantly alter the cancer environment. |

No. 3

| Name of Chinese herbal medicine | Danggui | The formal name | *Angelica Sinensis* (Oliv) Diels |
|---|---|---|---|
| Foundation | Page 876 of Dictionary of Chinese Medicine and page 893 of Chinese material medica Book 5 (published by Shanghai Scientific and Technical Publishing Company) | | |
| The place of origin, harvest season, and portion | Danggui is produced in Min Chian of Gansu. At late October, roots are cleaned by removing any dirt and stems. After semi-dried by air ventilation, they are bound as a bundle and smoked to dry. | | |
| Procedures for preparation and extraction | 1. Danggui of 5 kg is washed clean, sectioned into 3 or 4 stripes, immersed in water for 3 hours and then decocted in two parts.<br>2. After heating to evaporate the moisture till 3 liters of concentrate remaining, Fuling powder of 1 kg is mixed into.<br>3. Desiccation at 45° C.<br>4. The product is grounded and screened through a sieve of 100 and stored as powder. | | |
| Active ingredients | 12 types of volatile oils, including carvacrol, 11 types of aldehydes, inculding verbenone, 26 neutral oils, including liqustilide, 17 placid ingredients including anqelicide and 18 amino acids, including lysine, as well as 9 phospholipids, including lysophos phatidylcholine and 23 inorganic elements and polysaccharide. | | |
| Original pharmacological action | To enhance the hematopoiesis and circulation, eliminate the thrombi in vessels and prevent thrombosis.<br>Modern Pharmacology: To positively affect the circulation and hemopoietic system and promote the conversion of lymphocytes with an auxiliary anti-tumor effect. | | |
| Pharmacological application and purpose | To supplement necessary nutrients and inorganic elements, promote the circulation and conversion of lymphocytes, strengthen the cardio function and eliminate the thrombi in blood | | |

No. 4

| Name of Chinese herbal medicine | Hanxincao | The formal name | *Scutellaria indica* L. |
|---|---|---|---|
| Foundation | Page 2303 of Dictionary of Chinese Medicine and page 214 of Chinese material medica Book 7 (published by Shanghai Scientific and Technical Publishing Company) | | |
| The place of origin, harvest season, and portion | Hanxincao is produced in Fujian and Taiwan. The whole weed is harvested in spring and summer, cleaned and sun-dried. | | |

-continued

| | Pharmacological Data of Medication |
|---|---|
| Procedures for preparation and extraction | 1. 5 kg of the whole weed is washed clean and immersed in water for 3 hours and then decocted in two parts.<br>2. After heating to evaporate the moisture till 3 liters of concentrate remaining, Fuling powder of 1 kg is mixed into.<br>3. Desiccation at 60° C.<br>4. The product is grounded and screened through a sieve of 120 and stored as powder. |
| Active ingredients | Including various types of flavone, including scutellarein, and 5 types of Sophoradin, as well as phenolic compounds, amino acids, organic acid and 2, 3, 4, 5, 2', 4', 5', 6'-Octamethoxychalcone. |
| Original pharmacological action | Hanxincao is able to lower the higher temperature of organisms, promote blood circulation, alleviate the inflammation and swelling of infected connective tissues, and augment the defense and detoxication, as well kill the pain, reduce inflammation and stop the bleeding |
| Pharmacological application and purpose | Hanxincao is able to lower the higher temperature in liver and pancreas, promote blood circulation, eliminate the thrombi, bacteria, cancer cells in the portal vein, as well as reduce the pressure of the portal vein, prevent the regression in side circulation and stop the bleeding. |

No. 5

| | | | |
|---|---|---|---|
| Name of Chinese herbal medicine | Huotanmucao | The formal name | Polyqonum chinenSeL |
| Foundation | Page 500 of Dictionary of Chinese Medicine and page 648 of Chinese material medica Book 2 (published by Shanghai Scientific and Technical Publishing Company) | | |
| The place of origin, harvest season, and portion | Huotanmucao is produced in Fujian and Taiwan. The portion of plant above ground is harvested between summer and autumn, cleaned, sectioned and sun-dried. | | |
| Procedures for preparation and extraction | 1. 1 kg of dried Huotanmucao is desiccated and ground and additional 5 kg is immersed in water for 3 hours and then decocted in two parts.<br>2. After heating to evaporate the moisture till 3 liters of concentrate remaining, the original powder of 1 kg is mixed into.<br>3. Desiccation at 60° C.<br>4. The product is grounded and screened through a sieve of 120 and stored as powder. | | |
| Active ingredients | The leave of Huotanmucao contain β-sitosterol, kaempferal, quercetin, ellaqicacid, qallicacid, 3-O-methylellaqic acid, kaempferol-7-qlucoside and kaempferol-3-O-qlucuronide | | |
| Original pharmacological action | Huotanmucao is able to improve the water metabolism, lower the blood temperature and detoxification, as well as alleviate the tightness of vessels or tendon ligament.<br>Modern pharmacology: to resist the bacteria or hepatitis B virus infection, and lower the blood pressure. | | |
| Pharmacological application and purpose | To improve the microcirculation of liver and pancreas to promote the permeability, lower the pressure of portal vein and regulate the hepatic and pancreatic functions. | | |

No. 6

| | | | |
|---|---|---|---|
| Name of Chinese herbal medicine | Ainaxiang | The formal name | *Blumea balsainifera* (L) DC. |
| Foundation | Page 562 of Dictionary of Chinese Medicine and page 738 of Chinese material medica Book 7 (published by Shanghai Scientific and Technical Publishing Company) | | |
| The place of origin, harvest season, and portion | Huotanmucao is produced in Taiwan. The portion of plant above ground is harvested in autumn, cleaned, sectioned and sun-dried. | | |
| Procedures for preparation and extraction | 1. 8 kg of dried sections is immersed in water for 12 hours and then decocted in two parts.<br>2. After heating to evaporate the moisture till 3 liters of concentrate remaining, Fuling powder of 1 kg is mixed into.<br>3. Desiccation at 45° C.<br>4. The product is grounded and screened through a sieve of 120 and stored as powder. | | |
| Active ingredients | The leave of Ainaxiang contain (2R, 3R)-dihydroquerce-tin-4'-methylether, blumealactone, A, B, C, and blumeatin, as well as borneol | | |

-continued

| Pharmacological Data of Medication | |
|---|---|
| Original pharmacological action | Ainaxiang is able to eliminate the pathogenic causes of abnormality in circulation or abnormal pressure in blood capillaries, promote the water metabolism of local tissues or organs, maintain the suitable intra-abdominal temperature, stop diarrhea, smooth the circulation and eliminate the toxin inside the body. As indicated by Fuijimoto et al., the growth of Yoshida sarcoma could be inhibited by 5–10 kg/ml of blumealactone A, B, C extracted from the leaves of Ainaxiang. |
| Pharmacological application and purpose | In conjunction with other medications, it can eliminate inappropriate or hazardous gas from lymphatic or blood vessels by its function of urging the blood flow. |

No. 7

| Name of Chinese herbal medicine | Shuodiao | The formal name | *Sambucus javanica* Reinuw |
|---|---|---|---|

| | |
|---|---|
| Foundation | Page 2455 of Dictionary of Chinese Medicine and page 541 of Chinese material medica Book 7 (published by Shanghai Scientific and Technical Publishing Company) |
| The place of origin, harvest season, and portion | Shuodiao is produced in South China along the coast and Taiwan. After harvested in summer and autumn, roots and stems are sectioned and used while fresh. Young branches and leaves are finely chopped and sun-dried followed by grounding, screening through a sieve of 120 and storing as powder. |
| Procedures for preparation and extraction | 1. 20 kg of fresh roots and stems are immersed in 2 liters of 18□ rice wine and then decocted in two parts.<br>2. After heating to evaporate the moisture till 3 liters of concentrate remaining, 1 kg of leaf powder is mixed into.<br>3. Desiccation at 60° C.<br>4. The product is grounded and screened through a sieve of 120 and stored as powder. |
| Active ingredients | The whole weed contains flavone, phenolic compounds, tannin, saccharide, and chlorogenic acid. In addition, the dried leaves contain β-sitosterol, stigmasterol, α-amyrin, palmitate, ursolic acid and massive potassium nitrate |
| Original pharmacological action | Shuodiao is able to eliminate the causes for abnormal pressure in vessels and capillaries (relieve rheumatic pain), abolish the hindrance of water metabolism in local tissues or organs (expel the wetness), promote circulation to disperse thrombi, relieve the pain, help urination<br>In a clinical report, it was indicated that injection of 100% Shuodiao solution is effective in treatint acute bacterial diarrhea and acute tonsillitis, as well as pneumonia. Decoction and power of Shuodiao is effective against acute and chronic hepatitis. |
| Pharmacological application and purpose | To promote circulation to disperse thrombi and preserve the normal blood pressure and water metabolism around the tumor tissues to alleviate sharp pain caused by cancer. |

No. 8

| Name of Chinese herbal medicine | Malan | The formal name | *Baphicacanthus cusia* (Nees) Bremek |
|---|---|---|---|

| | |
|---|---|
| Foundation | Page 1270 of Dictionary of Chinese Medicine and page 450 of Chinese material medica Book 7 (published by Shanghai Scientific and Technical Publishing Company) |
| The place of origin, harvest season, and portion | Malan is produced in Fujian and Taiwan. After harvested in autumn, the whole plant is washed clean and separated as roots, stems and leaves. Leaves and young branches are sun-dried, grounded and screened through a sieve of 100 and stored as powder. Roots and stems are sectioned and sun-dried. |
| Procedures for preparation and extraction | 1. 8 kg of roots and stems are immersed in water for 8 hours and then decocted in two parts.<br>2. After heating to evaporate the moisture till 4 liters of concentrates remaining. After cooling down, 1 kg of leaf powder is mixed into till sticky.<br>3. Desiccation at 45° C.<br>4. The product is grounded and screened through a sieve of 120 and stored as powder. |
| Active ingredients | Leaves of Malan contain indicant, indirubin, indigo, and tryptantrin while the whole plant contains lupeol, betumin, lupenone, 4(3H)-quinazolinone and 2,4(1H, 3H)-quinazolinedione. Roots contain additionally chrysophand and β-sitosterol. |

-continued

| Pharmacological Data of Medication | |
|---|---|
| Original pharmacological action | Malan is able to lower abnormal temperature of organisms, increase the nutrient elements in the blood, neutralize the toxins, alleviate inflammation and hyperemia and stop bleeding. In modern pharmacology, one ingredient of Malan, indirubin, is capable of resisting the tumor formation and enhancing the phagocytosis of monocytes of mice. It has been proven to be clinically effective in treating infections of Spirochaete, Influenza Meningitidis, Mumps and Rosella. |
| Pharmacological application and purpose | To significant effect on the abnormality of cancer environment by functions of alleviating inflammation and hyperemia and detoxication. |

No. 9

| Name of Chinese herbal medicine | Ludou | The formal name | Viqna radiate (L.)R |
|---|---|---|---|

| | |
|---|---|
| Foundation | Page 2271 of Dictionary of Chinese Medicine and page 694 of Chinese material medica Book 4 (published by Shanghai Scientific and Technical Publishing Company) |
| The place of origin, harvest season, and portion | Ludou is produced in Taiwan. During mid August, seeds are mature, harvested and screened to remove any undesirable materials and then sun-dried. |
| Procedures for preparation and extraction | 1. 10 kg of seeds are washed clean and dried. A hole of 1 cm is drilled at the middle of fresh bamboo tubes with two end joints being kept and Ludou seeds are put in with 1/3 space left. The hole is then closed by bamboo plug, paraffin, and tape wrapping for air proof.<br>2. Immersion in urines of health person for at least 49 days.<br>3. Immersion with turning in a bucket of flowing spring. The inlet direction of spring is from bottom and outlet from the top for at least 49 days.<br>4. In a water reservoir with a presumed volume of 40 tons, spring water inlet from top. Those bamboo tubes with Ludou are immersed at the bottom of reservoir for at least 49 days.<br>5. After retrieving, bamboo tubes are placed on a clean ground and turned one or twice a day for sun, dew, wind, and rain. After 49 days, the bamboo tubes are open, sun-dried, ground, and screened through a sieve of 100 and stored as powder. |
| Active ingredients | Ludou contains carotene, riboflavine, blobulin, fructose and phophoslipids, such as phosphatidylcholine, phosphatidylethanolamine, phosphatidylinositol, phosphatidylglycerol, phosphatidylserine, and phosphatidicacid. |
| Original pharmacological action | Ludou, a nutrient, is able to supplement consumed energy, lower the high temperature caused by drastic ingredients (supplementing pancreas and clarify illusory heat), and eliminate toxic materials inside body, especially in liver and kidney to promote urination (detoxication and urination). In modern pharmacology, it can also reduce cholesterol, resist atherosclerosis, inhibit the increase of BUN, promote the excretion of creatine, increase the urination amount to promote the excretion of urine phosphate and significantly alleviate the damage to kidney and liver. As indicated by Han-Yuan Chen et al in the Academic Journal of First Medical University in 1989, the diet containing Ludou powder can reduce the number and mass of lung cancer and hepatoma induced by morphine and nitrous acid. |
| Pharmacological application and purpose | To eliminate toxic materials inside body, especially in liver, pancreas and kidney and lower the high temperature around tumors. The pharmacological effect of Ludouhuang, a Ludou extract, is even stronger, especially in the aspects of anti-infection and reduction in inflammation in cancer surrounding area. |

No. 10

| Name of Chinese herbal medicine | Canger | The formal name | Xanthium sibiricum patrex widd. |
|---|---|---|---|

| | |
|---|---|
| Foundation | Page 1069 of Dictionary of Chinese Medicine and page 1010 of Chinese material medica Book 7 (published by Shanghai Scientific and Technical Publishing Company) |
| The place of origin, harvest season, and portion | Canger is produced in Fujian and Taiwan. After harvested in spring, the whole plant is washed clean, sectioned and sun-dried. |

| | -continued |
|---|---|
| | Pharmacological Data of Medication |
| Procedures for preparation and extraction | 1. 6 kg of newly dried Canger are firmly pressed into a pot with adding of 2 liters of 18° C. rice wine. After heat steaming for softening, water is added into and decoction is performed twice.<br>2. After heating to evaporate the moisture till 3 liters of concentrates remaining, 1 kg of Fuling powder is mixed into.<br>3. Desiccation at 60° C.<br>4. The product is grounded and screened through a sieve of 120 and stored as powder. |
| Active ingredients | The whole plant contains strumaroside, xanthinin, and xanthumin, as well as derivatives of Sophoradin, soluble nucleoside, glucose, fructose, amino acid, Tartaric Acid, succinic acid, fumaric acid, Malic Acid, potassium nitrate, calcium sulfate, and iodine. |
| Original pharmacological action | Canger is able to eliminate the causes for abnormal pressure of vessels and capillaries, relieve the higher temperature inside body and skin (dispersal of wind and heat), remove toxins in defensive system and tissues, and kill germs and bugs (detoxication and eradication of bacteria).<br>In clinical reports, it has been reported to treat leprosy and chronic rhinitis, functional metrorrhagia and early stage of blood fluke infection. |
| Pharmacological application and purpose | To permeate lymphatic tissues for removing toxins in defensive and endoreticular systems. |

No. 11

| | | | |
|---|---|---|---|
| Name of Chinese herbal medicine | Daqinggen | The formal name | *Clerodendron Cyrtophyllum* Turez |
| Foundation | Page 129 of Dictionary of Chinese Medicine and page 567 of Chinese material medica Book 6 (published by Shanghai Scientific and Technical Publishing Company) | | |
| The place of origin, harvest season, and portion | Daqinggen is produced in Jiangsi. Roots and stems are dug out in summer, washed, sectioned and sun-dried. | | |
| Procedures for preparation and extraction | 1. 8 kg of Daqinggen sections are immersed in water for 12 hours, heated and decocted in two parts.<br>2. After heating to evaporate the moisture till 3 liters of concentrates remaining, 1 kg of Fuling powder is mixed into.<br>3. Desiccation at 60° C.<br>4. The product is grounded and screened through a sieve of 120 and stored as powder. | | |
| Active ingredients | The stems contain crytophyllone A and B, teuvincenone F, sugiol, triedelin, clerodolone, clerosterol, and stigrna-5, 22, 25-trien-3B01. | | |
| Original pharmacological action | Daqinggen is capable of relieving the body heat and high temperature on skin caused by lymphatic alteration and reducing the high temperature of blood, as well as helping in detoxication of lymphatic tissues. | | |
| Pharmacological application and purpose | To lower the higher temperature in blood and hepatic vessels and promote lymphatic permeability and normal circulation. | | |

No. 12

| | | | |
|---|---|---|---|
| Name of Chinese herbal medicine | Banbianlian | The formal name | *Lobelia Chinensis* Lour |
| Foundation | Page 754 of Dictionary of Chinese Medicine and page 613 of Chinese material medica Book 7 (published by Shanghai Scientific and Technical Publishing Company) | | |
| The place of origin, harvest season, and portion | Banbianlian is produced in Anhui, Fujian and Taiwan. After harvested in spring and autumn, the whole plant is washed clean and sun-dried. | | |
| Procedures for preparation and extraction | 1. 4 kg of Banbianlian are immersed in water for 3 hours and then decocted in two parts.<br>2. After heating to evaporate the moisture till 3 liters of concentrates remaining, 1 kg of Fuling powder is mixed into.<br>3. Desiccation at 60° C.<br>4. The product is grounded and screened through a sieve of 120 and stored as powder. | | |

-continued

| | Pharmacological Data of Medication |
|---|---|
| Active ingredients | Banbianlian contains alkaloids, mainly L-lobeline, lobelanine, lobelanidlne, isolobelanine, flavonoids, saponin, amino acid, polysaccharides, inulin, p-hydroxyacid, and succinic acid. The root and stem of Banbianlian contains lobelinin. |
| Original pharmacological action | Banbianlian can lower the higher temperature in tissue, activate defensive tissues, promote detoxication (elimination of heat and detoxication), enhance water metabolism, eliminate ascites and swelling of shin (helpful in elimination of water and swelling), penetrate lymphatic microcirculation of internal and neutralize the toxins.<br>In modem pharmacology, it can promote urination, secretion of bile and resistance to venom, as well as treat liver cirrhosis, ascites and various cancers. |
| Pharmacological application and purpose | To penetrate into the lymphatic microcirculation of deep portion of tissue and activate defensive organs to promote detoxication. |

No. 13

| Name of Chinese herbal medicine | Xingren | The formal name | *Armeniaca Vulgaris* Lam |
|---|---|---|---|
| Foundation | Page 1100 of Dictionary of Chinese Medicine and page 93 of Chinese material medica Book 4 (published by Shanghai Scientific and Technical Publishing Company) | | |
| The place of origin, harvest season, and portion | Xingren is produced in Northern China and east of Inner Mongolia. During the maturation season of June and July, the fruits are picked. After removing the flesh and washing and being dries, the kernel is retrieved by cracking the nutlet and sun-dried and protected from eaten by bugs. | | |
| Procedures for preparation and extraction | 1. 5 kg of Xingren are washed, cracked and immersed in water for 3 hours and then decocted in two parts. After heating to evaporate the moisture till 3 liters of concentrates remaining, 1 kg of Fuling powder is mixed into.<br>2. Desiccation at 60° C.<br>3. The product is grounded and screened through a sieve of 80 and stored as powder. | | |
| Active ingredients | Xingren contains amygdalin of around 4%, prunasin, fatty oil of about 50%, which is consist of 8 fatty acids, including 27% of linoleic acid, 67% of oleic acid and 5.2% of palmitic acid, as well as chlorogenic acid and neochlorogenic acid.<br>Apart from these, KR-A and KR-B with functions of anti-inflammation and pain killing, and volatile ingredients related to the scent of Xingren are also contained | | |
| Original pharmacological action | Xingren is able to alleviate the hypersensitivity to the trachea and bronchus in lung (stop coughing and smooth panting), lubricate the intestines and smooth excretion. It was used as external medicine of skin cancer on knees in ancient time. As indicated in Shansi Journal of Medicine by Su-Lian Zhao, muscular injection of amygdalin significantly promoted the mitosis and proliferation of spleen T lymphocytes in mice. | | |
| Pharmacological application and purpose | To go deep into the acidic environment of cancer to collaborate with other medications in altering the condition for treating cancers. | | |

No. 14

| Name of Chinese herbal medicine | Nuzhenzi | The formal name | *Ligustrum Lucidum* Ait |
|---|---|---|---|
| Foundation | Page 237 of Dictionary of Chinese Medicine and page 183 of Chinese material medica Book 6 (published by Shanghai Scientific and Technical Publishing Company) | | |
| The place of origin, harvest season, and portion | Nuzhenzi is produced in Zhejiang and Jiangsu. Seeds are harvested in December. After removing stems, leaves and others, seeds are placed in hot water to scald and then sun-dried. | | |
| Procedures for preparation and extraction | 1. 8 kg of Nuzhenzi are washed and immersed in water for 3 hours and then decocted in two parts.<br>2. After heating to evaporate the moisture till 3 liters of concentrates remaining, 1 kg of Fuling powder is mixed into.<br>3. Desiccation at 60° C.<br>4. The product is grounded and screened through a sieve of 120 and stored as powder. | | |
| Active ingredients | Nuzhenzi contains oleanolic acid, ursolic acid, various nucleosides, polysaccharides, and 7 types of phospholipids of a | | |

-continued

| | Pharmacological Data of Medication |
|---|---|
| | total 0.39%, as well as 11 elements, including K, Ca, Mg, Mg, Na, Zn, Fe, Mn, Cu, Ni, Cr, and Ag. Ligustrin, one ingredient, is able to activate the immunity. |
| Original pharmacological action | Nuzhenzi is able to supplement mild nutrients and trace inorganic elements to liver and kidney for augmenting hepatic and pancreatic functions, reduce the abnormal high temperature and non-specific heat caused by retentions of drastic elements in liver and kidney, alleviate the permeability of lymphatic system, reduce cholesterol in blood and reduce white blood cells. |
| Pharmacological application and purpose | To supplement trace inorganic and mild nutrients elements, amend cytokines and lymphatic circulation to activate the immunity. |

No. 15

| Name of Chinese herbal medicine | Qianhu | The formal name | Peucedanum Praeruptorum Dunn |
|---|---|---|---|
| Foundation | Page 1723 of Dictionary of Chinese Medicine and page 1008 of Chinese material medica Book 5 (published by Shanghai Scientific and Technical Publishing Company) | | |
| The place of origin, harvest season, and portion | Qianhu is produced in Sichuan and Jiangsi. Roots are dug out in winter and sun-dried after removal of dirt. | | |
| Procedures for preparation and extraction | 1. 6 kg of Qianhu are washed, and sectioned. 1 kg of these are grounded and the other 5 kg are immersed in water for 8 hours and then decocted in two parts.<br>2. After heating to evaporate the moisture till 3 liters of concentrates remaining, 1 kg of original Qianhu powder is mixed into.<br>3. Desiccation at 45° C.<br>4. The product is grounded and screened through a sieve of 100 and stored as powder. | | |
| Active ingredients | Qianhu contains various coumarins, incuding praeruptorin A, coumaringlycosides, such as marmesinin, and D-mannitol, β-sitosterol, galactitol, daucosterol, and pd-saponin V. | | |
| Original pharmacological action | Qianhu can regulate body temperature, guide the inappropriate air in the tissue (leading the air), dilute and expel viscous liquid (reducing phlegm and making expectoration easy), alleviate the nerviness in lung and upper digestive tracts, and promote metabolisms in digestive and respiratory system (metabolism). | | |
| Pharmacological application and purpose | To aid other medications in the respiratory, circulatory, and digestive systems to renovate the air and nature, especially in the metabolism in lung, stomach and pancreas. | | |

No. 16

| Name of Chinese herbal medicine | Jiatonghao | The formal name | Crassocephalum, crepidioides (Benth) |
|---|---|---|---|
| Foundation | Page 2183 of Dictionary of Chinese Medicine and page 792 of Chinese material medica Book 7 (published by Shanghai Scientific and Technical Publishing Company) | | |
| The place of origin, harvest season, and portion | Jiatonghao is produced in Fujian and Taiwan. The whole plant is harvested while being in buds in summer, washed and spread in ventilated place for 1 to 2 hours followed by chopping and storage. It is best to concentrate and extract right away. The efficiency sharply decreased after being ground or stored. | | |
| Procedures for preparation and extraction | 1. 8 kg of dried Jiatonghao are immersed in 1 liter of 18° C. rice wine for 3 hours and then decocted in two parts.<br>2. After heating to evaporate the moisture till 3 liters of concentrates remaining, 1 kg of Fuling powder is mixed into.<br>3. Desiccation at 45° C.<br>4. The product is grounded and screened through a sieve of 120 and stored as powder. | | |
| Active ingredients | Not clear | | |
| Original pharmacological action | Jiatonghao can eliminate drastic elements in blood, lower the higher temperature, enhance water metabolism of organisms, promote urination and excretion, and reduce inflammation. It was originally a folk prescription, but significantly effective in treating pain and high fever caused by pleurisy and pleuritic infection. | | |

-continued

| | Pharmacological Data of Medication |
|---|---|
| Pharmacological application and purpose | To eliminate drastic elements in blood, lower the higher temperature, especially in pleura, enhance water metabolism of organisms, and assist other medications in quickly relieving the local swelling and pain of hepatoma and pancreatic cancer. |

No. 17

| Name of Chinese herbal medicine | Yinchenhao | The formal name | *Artemisia Capillaris* Thunb |
|---|---|---|---|
| Foundation | Page 1588 of Dictionary of Chinese Medicine and page 687 of Chinese material medica Book 7 (published by Shanghai Scientific and Technical Publishing Company) | | |
| The place of origin, harvest season, and portion | Yinchenhao is produced in Fujian and Taiwan. Young branches are harvested in late spring and semi-dried in the shade followed by sun-dried. | | |
| Procedures for preparation and extraction | 1. 1 kg of Yinchenhao is grounded and another 5 kg of Yinchenhao are immersed in water for 3 hours and then decocted in two parts.<br>2. After slow heating to evaporate the moisture till 3 liters of concentrates remaining, 1 kg of original Yinchenhao powder is mixed into.<br>3. Desiccation at 45° C.<br>4. The product is grounded and screened through a sieve of 120 and stored as powder. | | |
| Active ingredients | The portion above ground contains volatile oil such as α-β-alkene and limonene, various styrenes and di-biethyl compounds such as capillone, various phenolic compounds such as phenol, and 15 types of fatty acids such as palmitica acid. The portion above ground contains 4 phenoxyketones such as capillarisin, as well as flavone such as cirsilineol, which is beneficial for gallbladder, and capillartemisin A and B. | | |
| Original pharmacological action | Yinchenhao is able to eliminate retained water and lower the higher temperature with functions of alleviating heat, eliminating inflammation and being beneficial for gallbladder. In modern pharmacology, it can conserve the functions of liver and pancreas, alleviate heat, eliminate inflammation, kill pain and resist microbiological infections. As indicated by Jen-Sha Lo in Academic Journal of Fu-Jian Medical College, decoction of Yinchenhao could resist tumor growth and inhibit mutations. In Communication of He-Han Chinese Medicine Association, Chiang-Shiu et al. have shown that Yinchenhao can direct hinder the proliferation of cancer cells. | | |
| Pharmacological application and purpose | To eliminate retained water from liver and gallbladder and lower the higher temperature and also able to lead hazardous bacteria and cancer cells out to promote the normalization of intrahepatic environment. | | |

No. 18

| Name of Chinese herbal medicine | Yujin | The formal name | *Curcuma chuanyujin* C. K. Hsiehet H. Zhang |
|---|---|---|---|
| Foundation | Page 1316 of Dictionary of Chinese Medicine and page 637 of Chinese material medica Book 8 (published by Shanghai Scientific and Technical Publishing Company) | | |
| The place of origin, harvest season, and portion | Yujin is produced in Sichuan. In late December, after removing withered stems and leaves, the underground portion is dug out and cleaned to remove dirt. After being steamed for 15 minutes, it is baked to dry and fibrous roots removed. | | |
| Procedures for preparation and extraction | 1. 6 kg of Yujin are sectioned. 1 kg of Yujin is grounded into fine powder and another 5 kg of Yujin are immersed in water for 8 hours and then decocted in two parts.<br>2. After heating to evaporate the moisture till 3 liters of concentrates remaining, 1 kg of original Yujin powder is mixed into.<br>3. Desiccation at 60° C.<br>4. The product is grounded and screened through a sieve of 120 and stored as powder. | | |
| Active ingredients | Curcumin, demethoxycurcumin, and bidemethoxycrucumin are contained. | | |
| Original pharmacological action | Yujin can promote blood and lymphatic circulation, relax the tightness of ligaments in liver, pancreas, and stomach, kill pain and promote the bile secretion.<br>In modern pharmacology, Yujin can protect liver and myocardium against damage and enhance the immunity. | | |

-continued

| | Pharmacological Data of Medication |
|---|---|
| Pharmacological application and purpose | To loosen the liver ligament and promote the circulation of liver and pancreas to help bile secretion. |

No. 19

| Name of Chinese herbal medicine | Zhishi | The formal name | *Citrus aurantium* L |
|---|---|---|---|

| | |
|---|---|
| Foundation | Page 1508 of Dictionary of Chinese Medicine and page 874 of Chinese material medica Book 4 (published by Shanghai Scientific and Technical Publishing Company) |
| The place of origin, harvest season, and portion | Zhishi is produced in Sichuan, Hunan, and Jiangsi. Youthful fruits are picked in May and June, cross-sectioned and sun-dried. |
| Procedures for preparation and extraction | 1. 6 kg of Zhishi are immersed in water for 8 hours and then decocted in two parts.<br>2. After heating to evaporate the moisture till 3 liters of concentrates remaining, 1 kg of Fuling powder is mixed into.<br>3. Desiccation at 60° C.<br>4. The product is grounded and screened through a sieve of 100 and stored as powder. |
| Active ingredients | Hesperidin, neohesperidin, naringin, synephrine, and N-methyltyramine are contained. Seeds contain limonoids, as well as 19-hydroxydeacetylnomilinic acid-17-B-D-glucoside. |
| Original pharmacological action | Zhishi can stimulate digestive tracts to eliminate abnormal materials and their aggregation, and dilute viscous liquid in the circulation (reduce phlegm and expel wetness). |
| Pharmacological application and purpose | Zhishi can stimulate smooth muscles of stomach and intestine to increase the electric frequency and therefore, promote the excretions of abnormal materials. It can also dilute viscous liquid in the hepatopancreatic circulation for the smooth flow in intrahepatic bile duct. |

No. 20

| Name of Chinese herbal medicine | Banxia | The formal name | *Pinellia ternate* (Thunb) Breit |
|---|---|---|---|

| | |
|---|---|
| Foundation | Page 775 of Dictionary of Chinese Medicine and page 513 of Chinese material medica Book 8 (published by Shanghai Scientific and Technical Publishing Company) |
| The place of origin, harvest season, and portion | Banxia is produced in Hubei, Henan and Shandong. Stem tubers are dug out in October and November. After removing dirt and being classified by size, stem tubers are skinned by pounding under flowing water, washed clean and sun-dried. Immersions in lime and licorice root are performed in sequential till numb taste and even yellow coloring of sections. |
| Procedures for preparation and extraction | 1. 1 kg of Banxia, which has been prepared and sectioned, is sprayed with 10 cc of water to mix. Another 4 kg of Banxia is immersed in water for 8 hours and then decocted in two parts.<br>2. After heating to evaporate the moisture till 2.5 liters of concentrates remaining, original powder is mixed into.<br>3. Desiccation at 60° C.<br>4. The product is grounded and screened through a sieve of 120 and stored as powder. |
| Active ingredients | Over 60 ingredients, such as volatile oil and 3-acetoamino-5-methylisooxazole are contained, as well as ephedrine, choline, amino acid, and inorganic elements such as Ca, K, Na, Fe, Al, Mg, Mn, T, and P. In addition, it contains polysaccharide amylose, banxia protein, and pancreatin. |
| Original pharmacological action | Banxia is able to anesthetize the nerve for vomit to alleviate the nerviness of upper digestive tracts (stop vomiting and backflow), dilute and prevent the formation of viscous materials in intestines, and reduce the gastric acid secretion.<br>In modern pharmacology, it can reduce gastric acid secretion to reduce the acidity of free and total acids, inhibit the activity of pepsin for protection against acute damage and promote the repair of mucous membrane. In the Pharmacology of Chinese Medicine, Yi-Kui Lee indicated that water extract of Banxia exhibited significant inhibition on the growth of hepatoma, sarcoma, and cervical cancer in animal studies. |

| | -continued |
|---|---|
| | Pharmacological Data of Medication |
| Pharmacological application and purpose | To reduce the acidity of free and total acids, reduce the viscosity of circulation to lead to the easy access of cancer medications for altering the environment. |

Preparations of Medication

Abovementioned powder medicines, after concentration and extraction (please refer to Pharmacological Data of Medication for procedures), are mixed at indicated ratios in a blender. After adding an appropriate amount of water, the slightly moistened powders are processed as tablets of 0.5 mg/tablet by a tablet presser, desiccated at 45° C. and stored in sealed glass bottles. Stored at a dry and cool place for further use.

Usage

Regardless of stages, primary or metastatic, or undergone therapy of dissection, thrombosis, chemotherapy, or radiation, any patients with hepatoma or pancreatic cancer could use. At 90 minutes after every meal, 8 tables are swallowed with water. The dosage should be decreased or halved for children.

Matters Needing Attention

Tablets could be only taken after at least 10 days of chemotherapy or radiation therapy, if patients have undergone. While taking these tablets, thrombosis, chemotherapy and radiation therapy are prohibited. Other medications or health foods are also contradicted to prevent interference. Torrid foodstuffs, such as onion, garlic, chives, alcohol, Chinesered pepper, thick sauce, and spices, including prickly ash, star anise, cinnamon, clove and fennel, are prohibited to use. The living place should not use toxic materials such mosquito coil incense or spray or germicide. Intensive exercise is not recommended and all social activities or engagements should be halted.

The Clinical Trial

The Aim and Description of this Trial:

By complying with certain regulations, one medication combination for treating hepatoma and pancreas was continuous given to evaluate the actual efficiency and statistically analyzed to conclude.

For consideration of subjects' lives and continuity of trials, alternative medications was administrated in case of non-cancer diseases and accidental symptoms and this trial medicine was continued without directly affecting the trial results.

The Strict Standards of Trial Subjects:

The Expelling of Trial Subjects:

Any patients, who have not been diagnosed by well-equipped hospitals, were expelled. Patients with cancers other than hepatoma or pancreatic cancer or with insignificant main symptoms, which may mislead the evaluation, were expelled. Those patients had undergone less than 3 treatment courses (12 days for each course) were also expelled due to a too short continuity, which may be misleading.

The Duration of Trial:

This trial has been carried out from March 1997 to December 2001. Regardless of tumor stages, types or efficiency, any patient complies with the abovementioned standard was recruited into this trial.

The Maintenance of Data:

All related information, in addition to be serially kept in "the practical execution of clinical trial" enclosed in this proposal, is maintained in the database of original hospitals which make the diagnosis and this execution unit.

Standards for Evaluation:

Significant efficiency: the main symptoms or pain of cancer disappear, or dispersion of partial tumor mass is seen by scientific examination such as scan and such dispersion continues till the end of trial. These are classified as significant efficiency.

With efficiency: the main symptoms or pain of cancer reduce significantly, or recession of tumor mass is seen by scanning and such recession of tumor continues till the end of trial.

Inefficiency: the main symptoms or pain of cancer are improved insignificantly, not improved, or continuing deteriorated.

Unknown: unable to evaluate due to unclear responses of subjects or lose contact. These unknown cases are classified as no efficiency.

Efficiency and Statistical Analysis:

A total of 77 cancer patients matched the standards of this trial.

Efficiency: in this trial, the efficiency rate is 79%, including 25 patients with significant efficiency and 36 patients with efficiency to give a total of 61 patients. Meanwhile, 13 patients with no efficiency and 3 patients were unknown to give a total of 16 patients (21%).

Gender: 55 male (71%) and 22 female (29%)

Category of hospitals: 20 patients from the $1^{st}$ grade hospitals (teaching hospitals, such as National Taiwan University Hospital, National Cheng Kung University Hospital, and Kaoshiung Medical Univeristy Hospital), 54 patients from the $2^{nd}$ grade hospitals (region hospitals, such as Navy General Hospital, Veterans General Hospitals, Chang Gung Hospital, and Chi Mei Hospital), 3 patients from the $3^{rd}$ grade hospitals (well-equipped general hospitals), and none from the $4^{th}$ grade hospitals (general hospitals without adequate equipments).

Prior to joining the trial: 6 patients (8%) directly enrolled into this trial and 68 patients (88%) join this trial after having inefficient treatments including dissection, thrombosis, chemotherapy, and radiation therapy. Furthermore, 3 patients were uncertain in this aspect.

Recurrence, spreading and metastasis: after treatment with western medications, the recurrence, spreading and metastasis have occurred in 21 patients (27%) and inefficiency and deterioration have occurred in 41 patients (53%).

Age: the average age of these 77 patients was 62 years old with the highest being 91 and the lowest being 36.

Descriptions of Ordinary Subjects in this Trial

Only 9 cases are concisely stated in this description and the detailed statements of these 9 cases and other 68 cases are enclosed in appendix 1.

1. No. 2, Mr. Wang, Born in 1932, Male

After being diagnosed as pancreatic cancer in a hospital of the $2^{nd}$ grade at March 2001, he was hospitalized and treated at the original hospital with a implantation of a bile catheter. This execution unit was informed on March 15 and he was treated for a total of 3 times with medications for 15 days.

On April 17, he was transferred to another hospital of the $2^{nd}$ grade to undergo a surgical dissection of gallbladder, pancreatic-bile duct, a part of pancreas, duodenum (about 2 inches), and stomach (½) since all abovementioned areas have been infiltered by cancer cells. On May 10, he officially came in for seeking treatment. His main symptoms including hindrance in upper digestive tracts and stomach and continuous hiccup after meals, as well as numbness and tightness in right costal area, tiredness and fatigue, thirst, darken of facial skin and red spots on the left forehead. After a course of medication, these main symptoms disappeared and the medication was stopped.

On Oct. 26, 2001, the main symptoms reappeared and he decided to continuously use this medication and enrolled into this trial. The main symptoms disappeared again, including red spots on the left forehead, and have not recurred again so far (May 2002).

2. No. 5, Mr. Chiang, Born in 1929, Male

After being diagnosed as hepatoma in a hospital of the $2^{nd}$ grade on September 1998, he was admitted into hospital and has accepted one thrombosis procedure.

On Nov. 22, 1998, he was enrolled into this trial and his main symptoms are swelling of right costal area, abdominal illness, skin itchiness, insufficient strength, movement difficulty, dizziness and unable to stand, and lost of appetite. On December 7, during the first course of treatment, such symptoms were significantly alleviated and the original hospital urged him to go back for checking.

On Apr. 3, 1999, 120 days after the treatment, he was back to receive this medication due to the deterioration, insufficient strength, sharp pain of right costal region and hardness of tumor area and his symptoms were significantly improved on April 17, during the second course of treatment. On May 3, the pain was mild and occasional and his tumor mass has become soft.

3. No. 8, Mr. Lee, Born in 1941, Male

After being diagnosed as hepatoma (5.5 cm) in a religious hospital of the $2^{nd}$ grade on May 1998, he was admitted into the hospital and transferred to a teaching hospital of the $1^{st}$ grade on May 2 for a hospitalization of 34 days. The original swelling has been dispersed, however, with no improvement for other symptoms.

He started to receive this medication from on Jul. 7, 1998, and his main symptoms at that time included pain and swelling at the right costal region, emaciation, tiredness and fatigue, and weary movement, as well as high blood pressure and gout. On August 5, during the first course, local pain and gout has vanished and protein inversion has been reduced.

On Nov. 29, 1998, his vitality, physical strength and life were as normal and he joined a travel group to Mainland China. On Mar. 2, 1999, during a group tour to southern part of this island, he complained a weakness of feet and shin and occasional sprain and his AFP decreased from 1200 to 205. A further improvement on his condition was observed on June 19.

4. No. 18, Mr. Lin, Born in 1967, Male

After being diagnosed as hepatoma (8.0 cm) in a hospital of the $3^{rd}$ grade on June of 1999, he was transferred to another two teaching hospitals of the $1^{st}$ grade for conformation. He has undergone twice of thrombosis procedures and scanned again at the mid November in a southern teaching hospital of the $1^{st}$ grade. The scan results showed that tumor has already metastasized to lung and inoperable.

He started to receive this medication on Dec. 2 of 1999, and his main symptoms included occasional pain, back pain and numbness at the right costal region, pain at the lower right shoulder, and skin rashes without itching. On December 14, during the first course, these main symptoms have been significantly improved. On Jan. 11 of 2000, tumor mass has been proven to be contracted by scanning, however, lung was slightly enlarged.

On Mar. 29 of 2000, the original tumor has contracted from 8.0 cm to 3.6 cm without any change for lung.

5. No. 23, Miss Zhuo, Born in 1961, Female

After being screened and diagnosed as sigmoid colon cancer in a hospital of the $2^{nd}$ grade in central Taiwan on August of 1998, she has undergone a partial dissection right away. In the follow-up at October, tumor has metastasized to intrahepatic bile duct with a size of about 2.0 cm. She has received three times of chemotherapy in time, however, her condition continued to deteriorate.

She started to receive this medication on Jan. 19 of 1999, and her main symptoms included numbness and pain of right costal region, shoulder and back with a radiation towards outside, irregular breathing in chest, sharp pain of local surgical area while coughing and occasional constipation. On February 3, during the first course of treatment, the main symptoms have been improved. On April 22, tumor on intrahepatic bile duct has significantly contracted to as 1.3 cm proven by scan and the main symptoms disappeared.

6. No. 25, Miss Hu, Born in 1954, Female

After being screened and diagnosed as ovary cancer in a military hospital of the $2^{nd}$ grade in southern Taiwan on November of 1999, she has undergone a surgery to remove the ovary and surrounding lymph nodes (her uterus has been removed at 9 years age due to myoma. She had another surgery at May 11, 2000 to dissect a 7 cm of intestine due to metastasis. Not for a long time, via scanning in a hospital of the $2^{nd}$ grade, a metastasized tumor of 0.9 cm was found in liver and her condition was deteriorating. In fear of another operation, she refused to have chemotherapy or radiation therapy. According to doctors of these 3 hospitals, she may die before June of 2000 if doing nothing.

She started to receive this medication on Apr. 21, 2000 in a critical condition. Based on the experience, tumor may have already metastasized into bones and her main symptoms included local mass, swelling and pain at lower abdomen, indigestion and gas accumulation at stomach, sour and pain and being unable to lift of right shoulder, pain of right costal region and chest, swelling and hardness of legs, tiredness and gasping, insufficient physical energy, and hindrance in urination and excretion.

After taking this medication, her main symptoms were significantly alleviated or even disappeared. Although her condition was undulated due to the complexity or accidental infections, all could be alleviated by this medication. Her CA125 level was back to normal from original 44.1, so did CEA, which is maintained below the normal levels. At the end of trial, she was near normal and still alive now (May 26, 2002).

7. No. 30, Mr. Hao, Born in 1960, Male

After being diagnosed as hepatoma in a famous hospital of the 2$^{nd}$ grade in southern Taiwan on February of 1999, he has undergone a surgery for dissection and stayed in that hospital for treatments and follow-up. On Sep. 7 of 2000, he collapsed due to sharp pain of right costal region and checked in-the Emergency Department of the original hospital. However, doctors reckoned that several tumors have recurred and liver transplantation was impossible. He could only depend on regularly take drug for anesthesia to relieve pain.

He started to receive this medication on Sep. 13 of 2000. His main symptoms included persistent and sever pain at right costal region, indigestion of stomach and swelling of abdomen, constipation (only 4 times in a month) with scattered stool, but normal urination. On September 24, during the first course of treatment, severe pain has vanished to skip the usage of anesthesia and the swelling has amended.

On Oct. 7 of 2000, he has transferred to a teaching hospital of the 1$^{st}$ grade in northern Taiwan for examination. His condition has been proven to be greatly improved and thrombosis and chemotherapy were applicable.

8. No. 42, Mr. Chen, Born in 1959, Male

After being diagnosed as hepatoma complicated with liver cirrhosis in a religious hospital of the 2$^{nd}$ grade in southern Taiwan in April of 1998, he was transferred to another hospital of the 2$^{nd}$ grade on April 9 for thrombosis procedure but the condition was still deteriorating.

He started to receive this medication on Apr. 19 of 1998. His main symptoms included occasional pain at right costal region, swelling and indigestion of stomach and swelling of feet, tiredness and lack of strength, and yellow-brownish facial skin. On May 1, during the first course of treatment, the main symptoms have been improved and on May 13, further improved since the liver tumor was dispersed as seen in scan. On December 27, all symptoms have all vanished and his spirit and physical strength has back to normal.

9. No. 44, Mr. Chen, Born in 1962, Male

After being diagnosed as hepatoma in a hospital of the 2$^{nd}$ grade in southern Taiwan in March of 1997, his condition has been slightly improved after treatment. On October 20 of 1999, he admitted into a public hospital for examination due to haematemesis and the results showed a recurrence hepatoma of 3.7 cm.

He started to receive this medication on Nov. 11 of 1999. His main symptoms included occasional pain at right costal region, indigestion of stomach, poor appetite, one excretion in 2 to 3 days and yellowish urination. On November 25, the pain of right costal region has alleviated and the swelling of stomach has vanished. The scan performed on Jan. 13 of 2000 has shown that the recurred tumor mass of 3.7 cm has significant reduced with no sign of tumor cells.

Concluded from abovementioned, this invention, one medication combination for hepatoma and pancreatic cancer, is based on continuing novel theories, including "A theory on birth, growth, aging and death of a creature", "A theory on the developing environment of a creature", "A theory on surrounding pathology of cancer", and "A theory on the relationship of six elements and pathology in a creature" to utilize "the nature and tendency of medication" to generate a repulsive environment for cancer cells via a way of "soft conquers tough" complying with the principle of nature. Therefore, the goal of curing the cancer is achieved. Such theory and remedy are invented by this inventor, which are the characteristics of this invention and different from the conventional views and remedies of "resistance, killing, and extermination of cancers". Furthermore, the medications and their ratios as listed in the claims are made of concentrated and extracted powder for the purposes of quick effects and preciseness. However, the crude preparation, decoction, and preparations for oral and intravenous injection with cancer curing effects are still included this claim.

| The practical subject in this clinical trial  No. 1 | |
|---|---|
| Cancer type: hepatoma<br>Original number of case: 98032102<br>The hospital making diagnosis:<br>Chang Gung Hospital in Kaohsiung<br>Hospital grade: regional (the 2$^{nd}$ grade)<br>Diagnosis method: CT and ultrasonic scan | Name of subject: Mr. Zin-Su Wang<br>Date of birth: 1947<br>Address: Dunggang, Pingtung Hsien<br><br>Date of diagnosis: March, 1998<br>Place of hospital: Kaohsiung Shien, Taiwan<br>Diagnosis: hepatoma with a tumor of 2.0 cm, liver cirrhosis and hepatic coma |
| Condition before trial: | Precedent treatments and results |
| Main cancer-related symptoms:<br>Pain of right costal region and swelling of stomach<br>Other minor symptoms:<br>Tiredness and fatigue, unsolidified stool of twice a day, and frequent micturition of small amount<br>This subject has enrolled into this trial since Apr. 14, 1998 till Aug. 27, 1998 for a total of 6 courses and 76 days.<br>Trial procedure:<br>The medication combination, specific for treating hepatoma and pancreatic cancer, is taken within 90 minutes after meals, that is 3 times a day for a total of 12 gm.<br>On May 7 of 1998, frequency of pain of the right costal region has reduced and the severity of swelling of stomach has amended. His condition has further | Hepatic coma while hospitalized in the original hospital. Pre-administration of medication was requested and officially enrolled into this trial after regaining conscious.<br><br><br><br><br><br><br><br><br><br>Determination of efficiency: with efficiency<br>Filed on Mar. 15, 2002 |

-continued

| | |
|---|---|
| improved on May 21 and stabilized on July 11 with solidified stool and better spirit. The medication was discontinued on August 15 for 22 days. Due to drinking, his stomach swelled again but no pain in the right costal region. The medication was continued for 12 days. | |

| The practical subject in this clinical trial No. 2 ||
|---|---|
| Cancer type: pancreatic cancer with metastasis<br>Original number of case: 01031521<br>The hospital making diagnosis: Pingtung Christian Hospital<br>Hospital grade: regional (the 2$^{nd}$ grade)<br>Diagnosis method: biopsy, CT and ultrasonic scan, and endoscopegraphy | Name of subject: Mr. Ching-Guy Wang<br>Date of birth: Mar. 6, 1932<br>Address: Yanpu, Pingtung Hsien<br><br>Date of diagnosis: Mar. 12, 2001<br>Place of hospital: Pingtung Hsien, Taiwan<br>Diagnosis: (1) pancreatic cancer diagnosed by Pingtung Christian Hospital (2) cancers metastasized to pancreas, liver, stomach and duodenum as diagnosed by Chang Gung Hospital |
| Condition before trial: | Precedent treatments and results |
| Main cancer-related symptoms: hindrance in upper digestive tracts and stomach and continuous hiccup after meals, as well as numbness and tightness in right costal area<br>Other minor symptoms: tiredness and fatigue, thirst, darken of facial skin and red spots on the left forehead.<br><br>This subject has enrolled into this trial since Mar. 15, 2001 till Feb. 27, 2002 for a total of 6 courses and 72 days.<br>Trial procedure:<br>The medication combination, specific for treating hepatoma and pancreatic cancer, is taken within 90 minutes after meals, that is 3 times a day for a total of 12 gm.<br>On May 10, 2001, he officially came in for seeking treatment. After a course of medication, these main symptoms disappeared and the medication was stopped. On October 26 of 2001, the main symptoms reappeared and he decided to continuously use this medication and enrolled into this trial. On January 16, the main symptoms disappeared again, including red spots on the left forehead. Stayed in the trial. | He was hospitalized with an implantation of a bile catheter. This execution unit was informed on March 15 and he was treated for a total of 3 times with medications for 15 days.<br>On April 17, he was transferred to Chang Gung Hospital for a surgical dissection of gallbladder, pancreatic-bile duct, a part of pancreas, duodenum (about 2 inches), and stomach (1/2) since all abovementioned areas have been metastasized by cancer cells.<br><br><br><br><br>Determination of efficiency:<br>Significant efficiency<br>Filed on Mar. 15, 2002 |

| The practical subject in this clinical trial No. 3 ||
|---|---|
| Cancer type: nodular hepatoma<br>Original number of case: 99021114<br>The hospital making diagnosis: Kaohsiung Medical University Hospital<br>Hospital grade: teaching (the 1$^{st}$ grade)<br>Diagnosis method: CT and ultrasonic scan | Name of subject: Mr. Kuo-Ping Wang<br>Date of birth: Sep. 24, 1945<br>Address: Gushan District, Kaohsiung City<br><br>Date of diagnosis: October, 1998<br>Place of hospital: Kaohsiung City<br>Diagnosis: nodular hepatoma, fatty liver, HBV carrier and vesicle in right kidney |
| Condition before trial: | Precedent treatments and results |
| Main cancer-related symptoms: occasional pain and tenderness of right costal region, swelling of stomach<br>Other minor symptoms: incomplete urination, salivation and burning under feet<br>This subject has enrolled into this trial since Feb. 11, 1999 till Mar. 30, 1999 for a total of 3.5 courses and 42 days.<br>Trial procedure:<br>The medication combination, specific for treating hepatoma and pancreatic cancer, is taken within 90 minutes after meals, that is 3 times a day for a total of 12 gm.<br>On Mar. 3, 1999 during the 2$^{nd}$ course, pain of right costal region has vanished and the swelling of stomach has amended. | Unknown<br><br><br><br><br><br><br><br><br><br><br><br>Determination of efficiency: significant efficiency<br>Filed on Mar. 15, 2002 |

-continued

On Mar. 25, 1999 during the 3rd course, the main symptoms have vanished, but the minor symptoms were unstable.

| The practical subject in this clinical trial No. 4 | |
|---|---|
| Cancer type: hepatoma with metastasis<br>Original number of case: 01032201<br>The hospital making diagnosis: Keelung Chang Gung Hospital<br>Hospital grade: regional (the 2nd grade)<br>Diagnosis method: CT and ultrasonic scan | Name of subject: Mr. Huo-Yan Chiang<br>Date of birth: Jan. 10, 1937<br>Address: Chidu District, Keelung<br><br>Date of diagnosis: October, 1996<br>Place of hospital: Keelung City, Taiwan<br>Diagnosis: hepatoma with 1 tumor of 2.0 cm, in 1998, 2 in left lobes and 3 in right lobes recurred |
| Condition before trial: | Precedent treatments and results |
| Main cancer-related symptoms: occasional pain of the right costal region and swelling of stomach, as well as abnormal sound during respiration and constriction during deep respiration<br>Other minor symptoms: tiredness and fatigue, dryness in mouth and tongue, and frequent micturition during the night<br><br>This subject has enrolled into this trial since Mar. 22, 2001 till Jun. 19, 2001 for a total of 7 courses and 84 days.<br>Trial procedure:<br>The medication combination, specific for treating hepatoma and pancreatic cancer, is taken within 90 minutes after meals, that is 3 times a day for a total of 12 gm.<br>On Apr. 1, 2001, the main symptoms have been improved and the diagnosis reports dated on March 27 and 31 of the original hospital were informed.<br>On April 16 and May 1, the main symptoms were continuously improved but limited improvement on the minor symptoms.<br>On May 16, the main symptoms were continuously improved with a pc of 270 and AFP has decreased from 50,000 to 23,950.<br>On June 5, results of laboratory examinations were informed and the condition was not deteriorating with an AFP of 25,405. | In 1996, 2 tumors were detected and alcohol chemotherapy was performed on October. Another 3 tumors were recurred in April 1998. Thrombosis was performed in October, 1998 and January 2001 and the AFP value ranged between 7,000 and 4,300. On Mar. 27, 2001, AFP elevated to 50,000 and on March 31, multiple tumors were discovered by ultrasonic scan.<br><br><br><br><br><br>Determination of efficiency: with efficiency<br>Filed on Mar. 15, 2002 |

| The practical subject in this clinical trial No. 5 | |
|---|---|
| Cancer type: hepatoma<br>Original number of case: 98112201<br>The hospital making diagnosis: An Tai Hospital, Dunggang<br>Hospital grade: regional (the 2nd grade)<br>Diagnosis method: CT and ultrasonic scan | Name of subject: Mr. Tan-Tsai Chiang<br>Date of birth: Oct. 14, 1929<br>Address: Shinbei, Pingtung Hsien<br><br>Date of diagnosis: September, 1998<br>Place of hospital: Pingtung Hsien, Taiwan<br>Diagnosis: hepatoma |
| Condition before trial: | Precedent treatments and results |
| Main cancer-related symptoms:<br>swelling of right costal area, abdominal illness, skin itchiness<br>Other minor symptoms:<br>Insufficient strength, movement difficulty, dizziness and unable to stand, and lost of appetite.<br>This subject has enrolled into this trial since Nov. 22, 1998 till Jun. 14, 1999 for a total of 6 courses and 72 days.<br>Trial procedure:<br>The medication combination, specific for treating hepatoma and pancreatic cancer, is taken within 90 minutes after meals, that is 3 times a day for a total of 12 gm.<br>On December 7, during the first course of treatment, all symptoms were significantly alleviated and the original hospital urged him to go back for checking. The treatment has stopped for 120 days.<br>On April 3 of 1999, he was back to receive this | After being diagnosed as hepatoma, he was admitted into hospital and has accepted thrombosis procedure twice.<br><br><br><br><br><br><br><br><br><br>Determination of efficiency: with efficiency<br>Filed on Mar. 15, 2002 |

|  |  |
|---|---|
| medication due to the condition deterioration, insufficient strength, sharp pain of right costal region and hardness of tumor area. On April 17, during the second course of treatment, the main symptoms were significantly improved. On May 3, the pain was mild and occasional and his tumor mass has become soft. |  |

| The practical subject in this clinical trial No. 6 ||
|---|---|
| Cancer type: hepatoma with metastasis in backbone Original number of case: 01122604 The hospital making diagnosis: Cheng Gong University Hospital, Tainan Hospital grade: teaching (the 1$^{st}$ grade) Diagnosis method: CT and ultrasonic scan | Name of subject: Mr. Zao-Yon Lee Date of birth: Sep. 18, 1942 Address: Jiading, Kaohsiung Hsien  Date of diagnosis: Nov. 28, 2001 Place of hospital: Tainan City, Taiwan Diagnosis: hepatoma metastasized to backbone after radiation, and liver cirrhosis. |
| Condition before trial: | Precedent treatments and results |
| Main cancer-related symptoms: Sharp pain in the costal region and swelling of abdomen, numbness and pain of left back, arms and feet, and movement difficulty. Other minor symptoms: lack of strength, incapability of movement, difficulty in excretion and frequent micturition of small amounts. This subject has enrolled into this trial since Dec. 26, 2001 till Feb. 26, 2002 for a total of 5 courses and 60 days. Trial procedure: The medication combination, specific for treating hepatoma and pancreatic cancer, is taken within 90 minutes after meals, that is 3 times a day for a total of 12 gm. On Jan. 6, 2002, during the first course, the sharp pain of right costal region has alleviated, movement difficulty has been improved with being able to lift the left foot. On January 20 and February 2, the pain of right costal region has vanished and other symptoms have been improved. On February 20, the swelling of abdomen has been alleviated. | After confirmed diagnose, he was admitted into Cheng Gong University Hospital on November 28, 2001 for 12 times of radiation therapy. The cancer has metastasized to spine and therefore, induced numbness and pain of lower body.   Determination of efficiency: with efficiency Filed on Mar. 15, 2002 |

| The practical subject in this clinical trial No. 7 ||
|---|---|
| Cancer type: hepatoma Original number of case: 99090913 The hospital making diagnosis: Kaohsiung Medical University Hospital Hospital grade: teaching (the 1$^{st}$ grade) Diagnosis method: CT and ultrasonic scan | Name of subject: Mr. Gin-Ying Lee Date of birth: 1993 Address: Lingya District, Kaohsiung City  Date of diagnosis: Sep. 7, 1999 Place of hospital: Kaohsiung City, Taiwan Diagnosis: hepatoma |
| Condition before trial: | Precedent treatments and results |
| Main cancer-related symptoms: Hard tumor mass, touched as stones, and occasional sudden pain in the right costal region and stomach, and swelling and complaint on both sides of abdomen. Other minor symptoms: movement difficulty of lower body during sleep, red urination and once or twice of excretion in a day. This subject has enrolled into this trial since Sep. 9, 1999 till Nov. 29, 1999 for a total of 4.5 courses and 54 days. Trial procedure: The medication combination, specific for treating hepatoma and pancreatic cancer, is taken within 90 minutes after meals, that is 3 times a day for a total of 12 gm. On Sep. 24, 1999, the tumor mass at the right costal region and stomach were significantly dispersed and soften. The sudden pain and swelling | Unknown        Determination of efficiency: with efficiency Filed on Mar. 15, 2002 |

| | |
|---|---|
| have been alleviated.<br>On October 8, the tumor mass has been dispersed and moveable due to the softening and contracting. The main symptoms have been further alleviated.<br>The medication has been stopped for 22 days after the condition improvement. The original hospital has asked him to visit for treatment, however, his condition has deteriorated.<br>On November 14, he was back into this trial and the symptoms have been alleviated again. | |

| The practical subject in this clinical trial No. 8 ||
|---|---|
| Cancer type: hepatoma<br>Original number of case: 98070701<br>The hospital making diagnosis: National Taiwan University Hospital<br>Hospital grade: teaching (the 1$^{st}$ grade)<br>Diagnosis method: nuclear examination and CT and ultrasonic scan | Name of subject: Mr. Wang-Tsai Lee<br>Date of birth: Dec. 16, 1941<br>Address: Luodung, Ilan Hsien<br><br>Date of diagnosis: May 22, 1998<br>Place of hospital: Taipei City, Taiwan<br>Diagnosis: hepatoma with a tumor of 5.5 cm, higher hepatic index, protein inversion, and lower RBC count |
| Condition before trial: | Precedent treatments and results |
| Main cancer-related symptoms:<br>Swelling and pain of right costal region and emaciation with darken skin<br>Other minor symptoms: tiredness and fatigue, frequent micturition of large amounts, lack of strength and complicated with hypertension and gout.<br>This subject has enrolled into this trial since Jul. 7, 1998 till Jun. 19, 1999 for a total of 22 courses and 244 days.<br>Trial procedure:<br>The medication combination, specific for treating hepatoma and pancreatic cancer, is taken within 90 minutes after meals, that is 3 times a day for a total of 12 gm.<br>On Jul. 18, 1998, the main symptoms have been alleviated.<br>On August 5, the tiredness has been alleviated and local pain and gout has vanished with a albumin of 3.2, globulin of 3.9, and RBC of 3,850,000. The protein inversion was still present but has been reduced.<br>On Nov. 29, 1998, his vitality, physical strength and life were as normal and he joined a travel group to Mainland China.<br>On March 2 of 1999, during a group tour to southern part of this island, he complained a weakness of feet and shin and occasional sprain and his AFP decreased from 1200 to 205.<br>A further improvement on his condition was observed on June 19 and his life and daily activity was as normal. | Initially diagnosed and treated at Luodung Goddess Hospital and then transferred to National Taiwan University Hospital and stayed for 34 days. The previous swelling was alleviated due to diarrhea, but other symptoms were not improved.<br><br><br><br><br><br><br>Determination of efficiency: significant efficiency<br>Filed on Mar. 15, 2002 |

| The practical subject in this clinical trial No. 9 ||
|---|---|
| Cancer type: hepatoma<br>Original number of case: 98091212<br>The hospital making diagnosis: Keelung Veteran General Hospital<br>Hospital grade: regional (the 2$^{nd}$ grade)<br>Diagnosis method: CT and ultrasonic scan, | Name of subject: Mrs. Me-May Yu<br>Date of birth: Sep. 5, 1943<br>Address: Keelung City<br><br><br>Date of diagnosis: Sep. 10, 1996<br>Place of hospital: Keelung City, Taiwan<br>Diagnosis: hepatoma and liver cirrhosis, which was reconfirmed by National Taiwan University Hospital. |
| Condition before trial: | Precedent treatments and results |
| Main cancer-related symptoms: occasional pain of the right costal region, swelling of stomach and occasional vomitous feeing, swelling of feet and shin, and headache spreading to the brow.<br>Other minor symptoms: sleep difficulty, constipation, and slight paralysis of the left side<br>This subject has enrolled into this trial since | After a long-term treatment at National Taiwan University Hospital with many times of thrombosis procedures, her condition continued to deteriorate. Tranquilizer was internally administrated for removing the pain. |

-continued

Sep. 12, 1998 till Nov. 29, 1998 for a
total of 4 courses and 48 days.
Trial procedure:
The medication combination, specific for treating
hepatoma and pancreatic cancer, is taken within 90
minutes after meals, that is 3 times a day for a total of
12 gm.
On Sep. 23, 1998, most main symptoms were
alleviated, except sleep difficulty.
On October 25, pain of the right costal region has
vanished and swelling and vomiting feeling have
been significantly improved, as well as the swelling
of feet and shin.
On November 17, apart from hardness of lower
abdomen, urination difficulty, and thirst, other
symptoms have vanished or further improved.

Determination of efficiency: with efficiency
Filed on Mar. 15, 2002

The practical subject in this clinical trial   No. 10

Cancer type: pancreatic adenocarcinoma (with
metastasis to liver)
Original number of case: 01010911
The hospital making diagnosis: Kaohsiung Veteran
General Hospital
Hospital grade: regional (the 2$^{nd}$ grade)
Diagnosis method: CT and ultrasonic scan Name of subject: Mrs. Show-Fong Yu
Date of birth: Mar. 18, 1962
Address: Fengshan, Kaohsiung Hsien Date of diagnosis: January, 2001
Place of hospital: Kaohsiung City, Taiwan
Diagnosis: pancreatic adenocarcinoma of 4.0 cm and
complicated with hepatoma, chronic hepatitis and
gallbladder stones Condition before trial:

Precedent treatments and results

Main cancer-related symptoms:
Swelling and pain of stomach, dryness in the mouth,
and salty or sour on the tongue, and hardness or pain
of the right costal region
Other minor symptoms: insufficient physical strength,
tiredness and fatigue, dizziness and sleepless, lost of
appetite, abnormal menses, pain in the intestine and
hernia, as well as occasional cold with high fever
This subject has enrolled into this trial since Jan.
9, 2001 till Feb. 12, 2002 for a total of 26 courses
and 312 days.
Trial procedure:
The medication combination, specific for treating
hepatoma and pancreatic cancer, is taken within 90
minutes after meals, that is 3 times a day for a total of
12 gm.
On February 3, the man symptoms have alleviated,
however, due to the internal injury from previous car
accident, dull pain of chest has occurred.
On March 7, the main symptoms have been alleviated
with sour on surface of tongue and heartburn.
On March 24, in the follow-up at Veteran General
Hospital, jaundice and liver function index were
normal, sour on the surface of tongue has been
amended, but with no menses, palpitation with fear,
sleepless and pain of chest.
On May 5, all symptoms were further improved.
On August 4, occasional pain, contraction and
hardness at the right costal region.
On August 29, symptoms were amended and via scan
at the original hospital, the tumor has been control
with no deterioration.
Minor symptoms and unexpected conditions of this
patients were exceptional numerous and induce pain
while severe. However, these were rapidly relieved
after taking this trial medication.

After a gallbladder dissection and implantation of a
bile catheter at the original hospital, he started to
receive this medication and while high fever or
temporary symptoms, return to the original hospital
for alternative treatment.

Determination of efficiency: with efficiency
Filed on Mar. 15, 2002

The practical subject in this clinical trial   No. 11

Cancer type: hepatoma
Original number of case: 00022903
The hospital making diagnosis: Kaohsiung Veteran
General Hospital
Hospital grade: regional (the 2$^{nd}$ grade)
Diagnosis method: nuclear examination and CT and
ultrasonic scan Name of subject: Mr. Fu-Chan Song
Date of birth: Mar. 5, 1965
Address: Nantz District, Kaohsiung City Date of diagnosis: September 1999
Place of hospital: Kaohsiung City, Taiwan -continued

| | Diagnosis: With ultrasonic scan in September, CT scan in October, and NMR in February 2002, 4 hepatoma mass of 3.5 cm were detected with a complication of kidney failure, once or twice dialysis in a week. |
|---|---|
| Condition before trial: | Precedent treatments and results |
| Main cancer-related symptoms:<br>Swelling or pain in the right costal region<br>Other minor symptoms: tiredness and fatigue, sleepless, and lost of appetite<br>This subject has enrolled into this trial since Feb. 29, 2000 till May 9, 2000 for a total of 4 courses and 48 days.<br>Trial procedure:<br>The medication combination, specific for treating hepatoma and pancreatic cancer, is taken within 90 minutes after meals, that is 3 times a day for a total of 12 gm. | Unknown except long term dialysis |
| On Mar. 16, 2000, the condition has been improved with the vanishment of pain at the right costal region. However, due to the vomiting at the previous day, there was illness in abdomen and thirst in mouth.<br>On April 7, the pain of right costal region did not happen again, but still sleepless, lost of appetite, weak urination. However, the dialysis interval could be prolonged to once in 10 days. | Determination of efficiency: with efficiency<br>Filed on Mar. 15, 2002 |

The practical subject in this clinical trial   No. 12

| Cancer type: hepatoma<br>Original number of case: 01072531<br>The hospital making diagnosis: Kaohsiung Chang Gung Hospital<br>Hospital grade: regional (the 2$^{nd}$ grade)<br>Diagnosis method: biopsy and CT and ultrasonic scan | Name of subject: Mr. Zong-Bai Wu<br>Date of birth: Jan. 20, 1927<br>Address: Luye, Taitung Hsien<br><br>Date of diagnosis: Jul. 2, 2001<br>Place of hospital: Kaohsiung Hsien<br>Diagnosis: a hepatoma of 5.0 cm, scanned first on July 2 at Liu Guang Shiong Hospital and reconfirmed by Chang Gung Hospital via biopsy. |
|---|---|
| Condition before trial: | Precedent treatments and results |
| Main cancer-related symptoms:<br>Occasional and unclear pain of right costal region and backflow due to belch<br>Other minor symptoms: tiredness and fatigue, lost of appetite, habitual constipation, and frequent and yellowish urination<br>This subject has enrolled into this trial since Jul. 5, 2001 till Sep. 11, 2001 for a total of 3 courses and 36 days.<br>Trial procedure:<br>The medication combination, specific for treating hepatoma and pancreatic cancer, is taken within 90 minutes after meals, that is 3 times a day for a total of 12 gm. | The previous medical record was absent. He directly join this trial and then referred to western treatment. |
| On Aug. 5, 2001, during the first course, main symptoms have been significantly alleviated.<br>On August 17, main symptoms have vanished. | Determination of efficiency: with efficiency<br>Filed on Mar. 15, 2002 |

The practical subject in this clinical trial   No. 13

| Cancer type: hepatoma<br>Original number of case: 01021606<br>The hospital making diagnosis: Kaohsiung Chang Gung Hospital<br>Hospital grade: regional (the 2$^{nd}$ grade)<br>Diagnosis method: CT and ultrasonic scan | Name of subject: Mr. Yue-Chiong Wu<br>Date of birth: Nov. 19, 1948<br>Address: Niausung, Kaohsiung Hsien<br><br>Date of diagnosis: June 2000<br>Place of hospital: Kaohsiung Hsien, Taiwan<br>Diagnosis: multiple radical hepatoma of small than 2.0 cm, complicated with hepatitis C. |
|---|---|
| Condition before trial: | Precedent treatments and results |
| Main cancer-related symptoms:<br>Tightness and pain of right costal region, and swelling of abdomen | Accepted many courses of chemotherapy with alcohol, and complicated with hypertension and uremia with long-term administration of medication |

-continued

| | |
|---|---|
| Other minor symptoms: frequent micturition of normal amount<br>This subject has enrolled into this trial since Feb. 16, 2001 till Apr. 13, 2001 for a total of 4.5 courses and 54 days.<br>Trial procedure:<br>The medication combination, specific for treating hepatoma and pancreatic cancer, is taken within 90 minutes after meals, that is 3 times a day for a total of 12 gm.<br>On Mar. 4, 2001, during the first course of treatment, the condition has been amended.<br>On March 17, the condition has been further improved with vanishment of tightness and pain of right costal region and reduction of swelling of abdomen.<br>On March 25, main symptoms have vanished without any recurrence. | for treatment.<br><br><br><br><br><br>Determination of efficiency: significant efficiency<br>Filed on Mar. 15, 2002 |

The practical subject in this clinical trial   No. 14

| | |
|---|---|
| Cancer type: hepatoma<br>Original number of case: 98081912<br>The hospital making diagnosis: Kaohsiung Veteran General Hospital<br>Hospital grade: regional (the 2$^{nd}$ grade)<br>Diagnosis method: biopsy, and CT and ultrasonic scan | Name of subject: Mr. Jin-Chang Wu<br>Date of birth: Feb. 21, 1928<br>Address: Yanpu, Pingtung Hsien<br><br><br>Date of diagnosis: July 1998<br>Place of hospital: Kaohsiung City, Taiwan<br>Diagnosis: hepatoma progressed from liver cirrhosis |
| Condition before trial: | Precedent treatments and results |
| Main cancer-related symptoms:<br>Hardness around the stomach (operation area of left liver lobe), which is like a inverted bowl, and occasional dull pain<br>Other minor symptoms: occasional numbness and pain of right shoulder and arms, tiredness and fatigue and sleepy<br>This subject has enrolled into this trial since Aug. 19, 1998 till Jun. 30, 1999 for a total of 16 courses and 192 days.<br>Trial procedure:<br>The medication combination, specific for treating hepatoma and pancreatic cancer, is taken within 90 minutes after meals, that is 3 times a day for a total of 12 gm.<br>On Sep. 5, 1998, main symptoms were alleviated.<br>On September 19, his vitality was better, but with swelling in the lower abdomen and indigestion.<br>On October 8, injury at the right costal region due to a fall.<br>On Jun. 30, 1999, main symptoms have vanished and swelling of stomach has dispersed for 4/5.<br>During the trial, due to numerous conditions, including a fall, a cold, or gout, the discontinuity of medication was longer, although the medication was efficient, and therefore, led to a long trial period. | The original diagnosis was liver cirrhosis, however, during the surgical dissection of partial left lobe, cancer cells were detected.<br><br><br><br><br><br><br><br><br>Determination of efficiency: with efficiency<br>Filed on Mar. 15, 2002 |

The practical subject in this clinical trial   No. 15

| | |
|---|---|
| Cancer type: hepatoma<br>Original number of case: 99111806<br>The hospital making diagnosis: Ruan Surgical General Hospital, Kaohsiung<br>Hospital grade: regional (the 2$^{nd}$ grade)<br>Diagnosis method: CT and ultrasonic scan | Name of subject: Mr. Jin-Lang Wu<br>Date of birth: Jan. 12, 1950<br>Address: Chianjen District, Kaohsiung City<br><br><br>Date of diagnosis: October 1999<br>Place of hospital: Kaohsiung City, Taiwan<br>Diagnosis: tumor mass at the distal end of liver, ranging from 6 × 7 cm to 2.0 × 3 cm and complicated with diabetes |
| Condition before trial: | Precedent treatments and results |
| Main cancer-related symptoms:<br>Gasp and cough during respiration, leading to sharp pain of right costal region and occasional pain on both costal sides | On November 4, thrombosis procedure was performed for the large tumor mass of 6 × 7 cm at the Ruan Surgical General Hospital. |

|  |  |
| --- | --- |
| -continued | |
| Other minor symptoms: tiredness and fatigue, frequent and massive amount of urination This subject has enrolled into this trial since Nov. 18, 1999 till Dec. 29, 1999 for a total of 3 courses and 36 days. Trial procedure: The medication combination, specific for treating hepatoma and pancreatic cancer, is taken within 90 minutes after meals, that is 3 times a day for a total of 12 gm. On Nov. 20, 1999, serious headache and high fever occurred on the next day after the trial, due to the spray of pesticide, and alternative medication was prescribed and administrated. On November 30, main symptoms were alleviated and accidental symptoms has been relieved. On December 5, the small tumor mass, which has not been through thrombosis procedure, has dispersed as proved by scanning at the original hospital. | Determination of efficiency: significant efficiency Filed on Mar. 15, 2002 |

| The practical subject in this clinical trial   No. 16 |
| --- |

| | |
| --- | --- |
| Cancer type: hepatoma (metastasized from nasopharyngeal cancer) Original number of case: 99092416 The hospital making diagnosis: Chi-Mei Hospital, Tainan Hospital grade: regional (the 2$^{nd}$ grade) Diagnosis method: biopsy, and CT and ultrasonic scan | Name of subject: Mr. An-Huei, Chiou Date of birth: Jun. 23, 1941 Address: Annan District, Tainan City  Date of diagnosis: August 1998 Place of hospital: Tainan City, Taiwan Diagnosis: nasopharyngeal cancer, which has metastasized as hepatoma as diagnosed in 1999) |
| Condition before trial: | Precedent treatments and results |
| Main cancer-related symptoms: Swelling and pain of stomach and abdomen, burn and sweating of waist and back, swelling and lump at the left costal region and tightness of chest Other minor symptoms: dryness in mouth and tongue and short of saliva after diathermy, frequent micturition of small amount (once in a hour during the night), and constipation. This subject has enrolled into this trial since Sep. 24, 1999 till Nov. 24, 1999 for a total of 3.5 courses and 42 days. Trial procedure: The medication combination, specific for treating hepatoma and pancreatic cancer, is taken within 90 minutes after meals, that is 3 times a day for a total of 12 gm. On Oct. 6, 1999, swelling and pain of stomach and abdomen have alleviated, so did the tightness of chest. On Oct. 21, 1999, his vitality was better and the pain has further alleviated. The swelling and hardness of left costal region has softened and dispersed. The medication has stopped from October 21 to November 12 for 16 days. He may go back to the hospital for treatment and the condition relapsed. On November 8, the medication was restarted again. | After being diagnosed as nasopharyngeal cancer, radiation and diathermy have been performed for 39 cycles at the original hospital. In June 1999, the tumor size was 4 × 4 cm in an ultrasonic scan, 5 × 6 cm after the treatment, and became 6.4 × 6 cm after 30 days.  On August 3 and Sep. 2, 1999, AFP value was 42.9 and 26.5, respectively. On September 25, before the trial, AFP was 37.9 and on October 20, after the trial, AFP was 34.0, which was stable and reduced.    Determination of efficiency: with efficiency Filed on Mar. 15, 2002 |

| The practical subject in this clinical trial   No. 17 |
| --- |

| | |
| --- | --- |
| Cancer type: hepatoma Original number of case: 01022432 The hospital making diagnosis: Dali Ren-Ai Hospital, Taichung Hospital grade: general (the 3$^{rd}$ grade) Diagnosis method: CT and ultrasonic scan | Name of subject: Mr. Yong-Tang Lin Date of birth: Apr. 18, 1940 Address: Dali City, Taichung Hsien  Date of diagnosis: November 2000 Place of hospital: Taichung Hsien, Taiwan Diagnosis: hepatoma, swelling and prostate hypertrophy |
| Condition before trial: | Precedent treatments and results |
| Main cancer-related symptoms: Swelling of right costal region and local varicosity, swelling of feet and shin, swelling of abdomen with | After the confirmation of diagnosis, thrombosis procedure was performed 3 times at the original hospital, however, tumor mass was continuously |

| -continued | |
|---|---|
| reduced fart, and jaundice.<br>Other minor symptoms:<br>Tiredness and fatigue, sleepless, atrophy of feet, skin itch, anus prolapse, prostate hypertrophy, and frequent micturition during the night<br>This subject has enrolled into this trial since Feb. 24, 2001 for a total of 3 courses and 36 days.<br>Trial procedure:<br>The medication combination, specific for treating hepatoma and pancreatic cancer, is taken within 90 minutes after meals, that is 3 times a day for a total of 12 gm.<br>On Mar. 8, 2001, the frequency of sudden pain of the right costal region was reduced, and pain, swelling, and varicosity were alleviated.<br>On March 22, swelling has vanished, blue veins only existed around the navel, and pain of right costal region has alleviated, but with tiredness, sleepiness and un-solidified stool. | enlarged and the conditions was deteriorating. Gastric hemorrhage occurred during the second thrombosis procedure.<br><br><br><br><br>Determination of efficiency: with efficiency<br>Filed on Mar. 15, 2002 |

| The practical subject in this clinical trial No. 18 | |
|---|---|
| Cancer type: hepatoma (with metastasis to lung cancer)<br>Original number of case: 99120202<br>The hospital making diagnosis: Linnei Hong-Yang Hospital<br>Hospital grade: general (the 3$^{rd}$ grade)<br>Diagnosis method: CT and ultrasonic scan | Name of subject: Mr. Zhi-Ming Lin<br>Date of birth: Mar. 1, 1967<br>Address: Linnei, Yunlin Hsien<br><br>Date of diagnosis: Jun. 14, 1999<br>Place of hospital: Yunlin Hsien, Taiwan<br>Diagnosis: hepatoma of 8.0 cm |
| Condition before trial: | Precedent treatments and results |
| Main cancer-related symptoms:<br>Occasional pain of the right costal region, pain of the right arm and backache of the hepatic area.<br>Other minor symptoms:<br>Skin pityriasis but not itchy<br><br><br><br>This subject has enrolled into this trial since<br>Dec. 2, 1999 till October<br>in a total of courses and days.<br>Trial procedure:<br>The medication combination, specific for treating hepatoma and pancreatic cancer, is taken within 90 minutes after meals, that is 3 times a day for a total of 12 gm.<br><br>On Dec. 14, 1999, main symptoms have been improved.<br>On Jan. 11, 2000, he informed us that via examination by Ren-Ai Hospital, tumor was significantly contracted and condition was improved with slight enlargement of lung.<br>On Mar. 29, 2000, he informed us that hepatoma was contracted from 8.0 cm to 3.6 cm and lung was back to normal again | The diagnosis was reconfirmed by Kaohsiung Medical University Hospital and Linko Chang Gung Hospital (both are teaching hospital of the 1$^{st}$ grade), and Dali Ren-Ai Hospital. After one thrombosis procedure in July 1999 at Kaohsiung Medical University Hospital and once again on November 2 at Ren-Ai Hospital, he was referred to Kaohsiung Medical University Hospital. However, the cancer has metastasized to lung and inoperable.<br><br>On Mar. 15, 2000, he called to inform us that the hepatoma was disappeared but occasional pain of right costal region with a rise of AFP from 5000 to 10,000. On Mar. 28, he informed us that the scan results of 2 hospitals were negative but one hospital has detected some spots. His pain of right costal region has vanished on June 7.<br>Determination of efficiency: with efficiency<br>Filed on Mar. 15, 2002 |

| The practical subject in this clinical trial No. 19 | |
|---|---|
| Cancer type: hepatoma<br>Original number of case: 10160603<br>The hospital making diagnosis: Kaohsiung Ruan Surgical General Hospital<br>Hospital grade: regional (the 2$^{nd}$ grade)<br>Diagnosis method: CT and ultrasonic scan | Name of subject: Mr. Wei-Shan Lin<br>Date of birth: Nov. 15, 1965<br>Address: Luju, Kaohsiung Hsien<br><br>Date of diagnosis: May, 2000<br>Place of hospital: Kaohsiung City<br>Diagnosis: hepatoma with metastasis to lung cancer |
| Condition before trial: | Precedent treatments and results |
| Main cancer-related symptoms:<br>Pain of right costal region, hypersensitivity or pain at the esophagus of chest | After confirmation of diagnosis at Kaohsiung Women and Children Hospital in July 1999 and reconfirmation and operation at Ruan Surgical |

-continued

| | |
|---|---|
| Other minor symptoms:<br>Sleepless, and un-solidified stool for 2–3 times a day, frequent and irregular yellowish urination.<br><br>This subject has enrolled into this trial since Jun. 6, 2001 till Jan. 17, 2002 for a total of 11 courses and 132 days.<br>Trial procedure:<br>The medication combination, specific for treating hepatoma and pancreatic cancer, is taken within 90 minutes after meals, that is 3 times a day for a total of 12 gm.<br>During the initial treatment, all symptoms were alleviated.<br>On Jul. 11, 2001, he was back to the hospital for follow-up and no recurrence was detected.<br>Due to various reasons, he discontinue the medication several times. During the follow-up on Dec. 14, 2001, recurrence has been detected. | General Hospital in May 2000, local cauterization was performed due to liver cirrhosis. He was admitted again due to the metastasis to lung cancer and treated with alcohol treatment, however, no efficient and hepatoma recurred.<br><br><br><br><br><br>Determination of efficiency: undetermined<br>Filed on Mar. 15, 2002 |

| The practical subject in this clinical trial No. 20 | |
|---|---|
| Cancer type: intrahepatic bile duct cancer<br>Original number of case: 01061008<br>The hospital making diagnosis: Kaohsiung Chang Gung Hospital<br>Hospital grade: regional (the 2$^{nd}$ grade)<br>Diagnosis method: CT and ultrasonic scan | Name of subject: Mr. Fu-Zhu Lin<br>Date of birth: Aug. 6, 1947<br>Address: Tianliau, Kaohsiung Hsien<br><br><br>Date of diagnosis: Jun. 17, 2001<br>Place of hospital: Kaohsiung Hsien, Taiwan<br>Diagnosis: 4 tumor mass, each of 6.0 cm, which was confirmed by Taipei He-Shin Hospital |
| Condition before trial: | Precedent treatments and results |
| Main cancer-related symptoms:<br>Occasional pain of right costal region and stomach, which was more serious during the night, and swelling of stomach without feeling hungry<br>Other minor symptoms:<br>Frequent and yellowish urination, tiredness and fatigue, lack of strength of feet, movement difficulty, dizziness, vomit, and constipation with once in 3–4 days.<br>This subject has enrolled into this trial since Sep. 12, 2001 till Jan. 9, 2002.<br>Trial procedure:<br>The medication combination, specific for treating hepatoma and pancreatic cancer, is taken within 90 minutes after meals, that is 3 times a day for a total of 12 gm.<br>On Sep. 12, 2001, after the trial, the condition was unstable and not much improved. At the end of treatment, his condition was even worse. | This patient was recommended for a recheck by big hospitals due to the suspicion of hepatoma from diagnosis on June 10 and 17 of 2001 (unrelated to this trial). The condition was not serious at the time. After being diagnosed by big hospitals, he started this trial as late as September 12 while his condition has deteriorated as listed left. If any thrombosis procedure or chemotherapy during these 3 months were unknown.<br><br><br><br><br><br>Determination of efficiency: inefficiency<br>Filed on Mar. 15, 2002 |

| The practical subject in this clinical trial No. 21 | |
|---|---|
| Cancer type: hepatoma<br>Original number of case: 98092601<br>The hospital making diagnosis: Kaohsiung Chang Gung Hospital<br>Hospital grade:<br>Diagnosis method: CT and ultrasonic scan and endoscopegraphy | Name of subject: Mr. Chuan-Yin Lin<br>Date of birth: Dec. 1, 1951<br>Address: Yanpu, Pingtung Hsien<br><br><br>Date of diagnosis: February, 1998<br>Place of hospital: Kaohsiung Hsien, Taiwan<br>Diagnosis: radical hepatoma, hypertrophy of veins at the distal end of esophagus |
| Condition before trial: | Precedent treatments and results |
| Main cancer-related symptoms:<br>Swelling and pain of the right costal region, and slight pain of esophagus and right chest during swallow.<br>Other minor symptoms:<br>Appetite, urination and excretion were normal<br>This subject has enrolled into this trial since Sep. 26, 1998 till Jun. 5, 1999 for a total of 6 courses and 72 days.<br>Trial procedure:<br>The medication combination, specific for treating | This patient was dumb and represented by the family. After the confirmation of diagnosis, he was treated by thrombosis and chemotherapy at the original hospital. |

-continued

| | |
|---|---|
| hepatoma and pancreatic cancer, is taken within 90 minutes after meals, that is 3 times a day for a total of 12 gm.<br>On Oct. 10, 1998, after the first course, the condition has been improved.<br>On Nov. 4, 1998, the main symptoms have vanished.<br>On December 6, at the end of treatment, all symptoms did not recur.<br>On Mar. 18, 1999, another 2 courses of treatment was given due to the pain at esophagus or pharynx during swallow. | Determination of efficiency: significant efficiency<br>Filed on Mar. 15, 2002 |

| The practical subject in this clinical trial No. 22 ||
|---|---|
| Cancer type: hepatoma<br>Original number of case: 01030806<br>The hospital making diagnosis: Pingtung Christian Hospital<br>Hospital grade: regional (the 2$^{nd}$ grade)<br>Diagnosis method: CT and ultrasonic scan | Name of subject: Mr. Zheng-Liang Zhou<br>Date of birth: Jul. 10, 1940<br>Address: Fengshan, Kaohsiung Hsien<br><br>Date of diagnosis: Feb. 5, 2001<br>Place of hospital: Pingtung City, Taiwan<br>Diagnosis: a hepatoma of 4.6 cm, referred to Chang Gung Hospital on February 9 and scanned on March 8 with a tumor of 4.9 cm |
| Condition before trial: | Precedent treatments and results |
| Main cancer-related symptoms:<br>Hardness and tightness of the right costal region, stuffiness or pain of stomach and chest<br>Other minor symptoms:<br>Insufficient physical strength, poor appetite, constipation, frequent micturition and Parkinson's disease<br>This subject has enrolled into this trial since Mar. 8, 2001 till Apr. 26, 2001 for a total of 4 courses and 48 days.<br>Trial procedure:<br>The medication combination, specific for treating hepatoma and pancreatic cancer, is taken within 90 minutes after meals, that is 3 times a day for a total of 12 gm.<br>On Mar. 21, 2001, main symptoms has been alleviated, so did the minor symptoms. From the scan, hepatoma has contracted and hepatic function index, except ALT/AST, was reduced for performing the thrombosis procedure.<br>On Apr. 4 and 10, 2001, conditions were further improved. | After referring to Chang Gung Hospital on Feb. 9 2001, due to the weakness of patients and the enormous size of tumor, thrombosis procedure was difficult and too risky to performe.<br><br><br><br><br><br><br><br><br><br><br>Determination of efficiency: with efficiency<br>Filed on Mar. 15, 2002 |

| The practical subject in this clinical trial No. 23 ||
|---|---|
| Cancer type: hepatoma (metastasized from sigmoid cancer)<br>Original number of case: 99011911<br>The hospital making diagnosis: Shalu Kuang-Tian Hospital<br>Hospital grade: regional (the 2$^{nd}$ grade)<br>Diagnosis method: CT and ultrasonic scan | Name of subject: Mrs. Jin-Lian Zhuo<br>Date of birth: Aug. 26, 1961<br>Address: Chingshuei, Taichung Hsien<br><br>Date of diagnosis: August 1998<br>Place of hospital: Taichung Hsien, Taiwan<br>Diagnosis: sigmoid cancer and after the dissection, a metastasized tumor of 2.0 cm was to intrahepatic bile duct |
| Condition before trial: | Precedent treatments and results |
| Main cancer-related symptoms:<br>Numbness and pain, which was radial outward, of right costal region, shoulder and back, stuffiness of chest, sharp pain at the local operation area (intestine) during cough<br>Other minor symptoms:<br>Occasional constipation<br>This subject has enrolled into this trial since Jan. 19, 1999 till Nov. 23, 2000 for a total of 10 courses and 120 days.<br>Trial procedure:<br>The medication combination, specific for treating | After dissection of sigmoid cancer in August 1998, a metastasized tumor of 2.0 cm was found in the intrahepatic bile duct, 3 courses of chemotherapy were performed right after. |

|  |  |
|---|---|
| -continued | |
| hepatoma and pancreatic cancer, is taken within 90 minutes after meals, that is 3 times a day for a total of 12 gm.<br>On Feb. 2, 1999, main symptoms have been alleviated.<br>On Mar. 2, 1999, symptoms were further improved.<br>On Apr. 22, 1999, the metastasized tumor has shrunk to only 1.3 cm as seen by scanning and main symptoms have vanished | Determination of efficiency: significant efficiency<br>Filed on Mar. 15, 2002 |

| The practical subject in this clinical trial   No. 24 ||
|---|---|
| Cancer type: intrahepatic bile duct cancer<br>Original number of case: 01020806<br>The hospital making diagnosis: Linko Chung Gang Hospital<br>Hospital grade: teaching (the 1$^{st}$ grade)<br>Diagnosis method: biopsy | Name of subject: Mrs. Yang-Zhi Zhuo<br>Date of birth: Nov. 20, 1949<br>Address: Chingshuei, Taichung Hsien<br><br>Date of diagnosis: November 2000<br>Place of hospital: Taipei Hsien, Taiwan<br>Diagnosis: intrahepatic bile duct cancer and recurrence after dissection |
| Condition before trial: | Precedent treatments and results |
| Main cancer-related symptoms:<br>Jaundice and pain of right costal region due to implantation of catheter, swelling of abdomen and stomach, stuffiness, unclear pain at the navel, and ache of shoulder, arms and back<br>Other minor symptoms:<br>Dizziness, tiredness and fatigue, movement difficulty, sleepless, thirst, and lost of appetite<br>This subject has enrolled into this trial since Feb. 8, 2001 till Jul. 19, 2001 for a total of 8 courses and 96 days.<br>Trial procedure:<br>The medication combination, specific for treating hepatoma and pancreatic cancer, is taken within 90 minutes after meals, that is 3 times a day for a total of 12 gm.<br>On Feb. 20, 2001, the condition was severe.<br>On Mar. 7, 2001, main symptoms were greatly improved. Sharp pain of right costal region recurred after 5 courses of treatment.<br>On May 3, 2001, he informed us that tumor was found to be slightly larger through a scan at Chang Gung Hospital. | The tumor recurred after dissection. From Dec. 15, 2000, chemotherapy was performed for 6 courses and tumor was still enlarged with significant deterioration of hepatic function, anesthesia and tranquilizer were needed due to the unbearable pain.<br><br><br><br><br><br><br><br><br><br>Determination of efficiency: inefficiency<br>Filed on Mar. 15, 2002 |

| The practical subject in this clinical trial   No. 25 ||
|---|---|
| Cancer type: hepatoma (metastasis of ovary cancer and intestine cancer)<br>Original number of case: 00042111<br>The hospital making diagnosis: Kaohsiung Veteran General Hospital<br>Hospital grade: regional (the 2$^{nd}$ grade)<br>Diagnosis method: biopsy and CT and ultrasonic scan | Name of subject: Mrs. Gui-Zhu Hu<br>Date of birth: Apr. 23, 1954<br>Address: Sanmin District, Kaohsiung<br><br>Date of diagnosis: November 1999<br>Place of hospital: Kaohsiung City, Taiwan<br>Diagnosis: ovary cancer which metastasized to intestine and liver after dissection |
| Condition before trial: | Precedent treatments and results |
| Main cancer-related symptoms:<br>Local lump of abdomen, swelling and pain of abdomen, ache of right shoulder and arm, movement difficulty, pain of costal region and chest, and swelling of feet and shin.<br>Other minor symptoms:<br>Tiredness and easy to gasping, insufficient strength, incomplete urination and obstruction of excretion<br><br><br>This subject has enrolled into this trial since Apr. 21, 2000 till Dec. 27, 2001 for a total of 48 courses and 576 days. | After undergone a surgery on Dec. 6, 1999 to remove the ovary and surrounding lymph nodes (her uterus has been removed at 9 years age due to myoma, she had another surgery at May 11 2000 to dissect a 7 cm of intestine due to metastasis. Not for a long time, via scanning at Ruan Surgical Hospital, a metastasized tumor of 0.9 cm was found in liver and her condition was deteriorating. According to doctors of Veteran General Hospital and Chung Gung Hospital, she may die before June of 2000 if without treatment. |

-continued

| | |
|---|---|
| Trial procedure:<br>The medication combination, specific for treating hepatoma and pancreatic cancer, is taken within 90 minutes after meals, that is 3 times a day for a total of 12 gm.<br>After taking this medication, her main symptoms were significantly alleviated or even disappeared. Although her condition was undulated due to the complexity or accidental infections, all could be alleviated by this medication. Her CA125 level was back to normal from original 44.1, so did CEA, which is maintained below the normal levels till the end of trial. | Determination of efficiency: significant efficiency<br>Filed on Mar. 15, 2002 |

| The practical subject in this clinical trial No. 26 | |
|---|---|
| Cancer type: hepatoma<br>Original number of case: 01021511<br>The hospital making diagnosis: MacKay Memorial Hospital<br>Hospital grade: regional (the 2$^{nd}$ grade)<br>Diagnosis method: CT and ultrasonic scan | Name of subject: Mr. Zhu Hong<br>Date of birth: 1929<br>Address: Houlung, Miaoli Hsien<br><br>Date of diagnosis: Sep. 10, 2001<br>Place of hospital: Taipei City, Taiwan<br>Diagnosis: a hepatoma of 10 cm complicated with hypertension |
| Condition before trial: | Precedent treatments and results |
| Main cancer-related symptoms:<br>Hardness and local persistent pain of right costal region, and swelling of abdomen and shin<br>Other minor symptoms:<br>Lost of appetite and obstructed urination<br>This subject has enrolled into this trial since Feb. 15, 2001 till Mar. 22, 2001 a total of 3 courses and 36 days.<br>Trial procedure:<br>The medication combination, specific for treating hepatoma and pancreatic cancer, is taken within 90 minutes after meals, that is 3 times a day for a total of 12 gm.<br>On Apr. 24, 2001, persistent pain of the right costal region has been significantly improved with a normal blood pressure.<br>On Mar. 15, 2001, condition was stable without any further improvement. | Determination of efficiency: inefficiency<br>Filed on Mar. 15, 2002 |

| The practical subject in this clinical trial No. 27 | |
|---|---|
| Cancer type: hepatoma<br>Original number of case: 98010712<br>The hospital making diagnosis: Luju Wen Surgical Hospital<br>Hospital grade: general (the 3$^{rd}$ grade)<br>Diagnosis method: CT and ultrasonic scan | Name of subject: Mr. Jin-Lai Hon<br>Date of birth: Jul. 22, 1955<br>Address: Luju, Kaohsiung Hsien<br><br>Date of diagnosis: 1997<br>Place of hospital: Ksohsiung Hsien, Taiwan<br>Diagnosis: hepatoma with liver cirrhosis and AFP over 1000 |
| Condition before trial: | Precedent treatments and results |
| Main cancer-related symptoms:<br>Occasional swelling and pain of the right costal region and subacute jaundice<br>Other minor symptoms:<br>Tiredness and fatigue, sleepless, and yellowish urination<br>This subject has enrolled into this trial since Jan. 7, 1998 till Apr. 25, 1998 for a total of 6 courses.<br>Trial procedure:<br>The medication combination, specific for treating hepatoma and pancreatic cancer, is taken within 90 minutes after meals, that is 3 times a day for a total of 12 gm.<br>On Jan. 20, 1998, main symptoms were alleviated.<br>On Jan. 27, due to the cold and cough, alternative "Shuang Jie San" was administrated.<br>On Feb. 12, 1998, main symptoms were further | Directly enrolled into this trial<br><br><br><br><br><br><br><br><br><br><br><br>Determination of efficiency: with efficiency<br>Filed on Mar. 15, 2002 |

-continued alleviated as confirmed by Tainan County Hospital, and main symptoms have vanished before the end of treatment.

| The practical subject in this clinical trial No. 28 | |
|---|---|
| Cancer type: hepatoma<br>Original number of case: 01091603<br>The hospital making diagnosis: Ren-Ai Hospital, Taipei<br>Hospital grade: regional (the 2$^{nd}$ grade)<br>Diagnosis method: CT and ultrasonic scan | Name of subject: Mrs. Lai-Mei-Gui Chiang<br>Date of birth: Apr. 2, 1936<br>Address: Shiaying, Tainan Hsien<br><br>Date of diagnosis: April 2000<br>Place of hospital: Taipei City, Taiwan<br>Diagnosis: hepatoma with a large one of 4 cm and numerous small ones from 2 to 10 cm, complicated with hypertension |
| Condition before trial: | Precedent treatments and results |
| Main cancer-related symptoms:<br>Pain of the right costal region, swelling of stomach, stuffiness of chest and abdominal swelling<br>Other minor symptoms:<br>Tiredness and fatigue, lost of appetite, constipation, obstructed urination and weakness<br>This subject has enrolled into this trial since Sep. 16, 2001 till Nov. 20, 2001 for a total of 5 courses and 60 days.<br>Trial procedure:<br>The medication combination, specific for treating hepatoma and pancreatic cancer, is taken within 90 minutes after meals, that is 3 times a day for a total of 12 gm.<br>On September 28, during the first course, main symptoms were greatly improved, however, urination was still obstructed and waist was too weak to sit for long.<br>On Oct. 11, 2001, abdominal swelling was alleviated and no obstruction for urination and excretion. At the end of treatment, main symptoms were greatly improved with the vanishment of swelling. | After 3 thrombosis procedures being performed at the original hospital, the patient's condition still deteriorated.<br><br><br><br><br><br><br><br><br><br>Determination of efficiency: with efficiency<br>Filed on Mar. 15, 2002 |

| The practical subject in this clinical trial No. 29 | |
|---|---|
| Cancer type: hepatoma<br>Original number of case: 01021613<br>The hospital making diagnosis: National Chung Gung University Hospital<br>Hospital grade: teaching (the 1$^{st}$ grade)<br>Diagnosis method: CT and ultrasonic scan | Name of subject: Mr. Wen-Shan Hou<br>Date of birth: Oct. 21, 1941<br>Address: Beimen, Tainan Hsien<br><br>Date of diagnosis: Feb. 16, 2001<br>Place of hospital: Tainan City, Taiwan<br>Diagnosis: hepatoma |
| Condition before trial: | Precedent treatments and results |
| Main cancer-related symptoms:<br>Stuffy pain and sudden pain of right costal region, which was even severe during the night, chest pain and cough<br>Other minor symptoms:<br>Obstructed and unsolidified excretion, frequent micturition of small amount and sleepless<br>This subject has enrolled into this trial since Feb. 16, 2001 till Apr. 28, 2001 for a total of 6 courses.<br>Trial procedure:<br>The medication combination, specific for treating hepatoma and pancreatic cancer, is taken within 90 minutes after meals, that is 3 times a day for a total of 12 gm.<br>On Feb. 16, 2001, during the first course, main symptoms were improved and further improved on Mar. 8, 2001.<br>On Mar. 22, 2001, via the scan at the original hospital, tumor was stable and slightly shrunken with a decrease of AFP from 242 to about 100. | After the confirmation of diagnosis, the patient was enrolled into this study.<br>On Apr. 4, 2001, after the improvement of condition, the original hospital asked the patient to go back for unknown treatment.<br><br><br><br><br><br><br><br><br>Determination of efficiency: with efficiency<br>Filed on Mar. 15, 2002 |

-continued

| The practical subject in this clinical trial No. 30 | |
|---|---|
| Cancer type: hepatoma<br>Original number of case: 00091312<br>The hospital making diagnosis: Kaohsiung Chang<br>Gung Hospital<br>Hospital grade: regional (the 2$^{nd}$ grade)<br>Diagnosis method: biopsy and CT and ultrasonic scan | Name of subject: Mr. Wei-Zhang Hou<br>Date of birth: Apr. 17, 1960<br>Address: Putz, Chiai Hsien<br><br>Date of diagnosis: February 1999<br>Place of hospital: Kaohsiung Hsien<br>Diagnosis: hepatoma, which recurred after the dissection |
| Condition before trial: | Precedent treatments and results |
| Main cancer-related symptoms: sharp pain of the right costal region (heavy sweating if happen), and enormous swelling of stomach and abdomen<br>Other minor symptoms: unsolidifled excretion of 4 times a day but normal urination<br><br>This subject has enrolled into this trial since Sep. 13, 2000 till Oct. 19, 2000 for a total of 3 courses and 36 days.<br>Trial procedure:<br>The medication combination, specific for treating hepatoma and pancreatic cancer, is taken within 90 minutes after meals, that is 3 times a day for a total of 12 gm.<br>On September 24, during the first course of treatment, severe pain has vanished and the swelling has amended.<br>On October 7 of 2000, he has transferred to National Taiwan University Hospital for examination. His condition has been greatly improved and thrombosis and chemotherapy were applicable. | In the middle of February 1999, he underwent a surgery for removing hepatoma and stayed in the original hospital for treatment and follow-up. On September 7 of 2000, he collapsed due to sharp pain of right costal region and checked in the Emergency Department of the original hospital. However, doctors reckoned that nothing could be done and transplantation was impossible.<br><br><br><br><br><br>Determination of efficiency: significant efficiency, efficiency, no efficiency and undetermined<br>Filed on Mar. 15, 2002 |

| The practical subject in this clinical trial No. 31 | |
|---|---|
| Cancer type: hepatoma<br>Original number of case: 99071406<br>The hospital making diagnosis: Kaohsiung Chang<br>Gung Hospital<br>Hospital grade: regional (the 2$^{nd}$ grade)<br>Diagnosis method: CT and ultrasonic scan and Angiography | Name of subject: Mr. Rong-Zhou Kuo<br>Date of birth: Feb. 3, 1943<br>Address: Nantz District, Kaohsiung City<br><br>Date of diagnosis: Jun. 10, 1999<br>Place of hospital: Kaohsiung Hsien, Taiwan<br>Diagnosis: diagnosed by CT scan at Veteran General Hospital on May 1 1999, and confirmed by angiography at Chang Gung Hospital. |
| Condition before trial: | Precedent treatments and results |
| Main cancer-related symptoms:<br>Occasional swelling and pain of the right costal region, frequent and yellowish urination of small amount, and swelling of shin<br>Other minor symptoms:<br>Tiredness and fatigue<br>This subject has enrolled into this trial since Jul. 14, 1999 till Dec. 12, 1999 for a total of 8 courses and 96 days.<br>Trial procedure:<br>The medication combination, specific for treating hepatoma and pancreatic cancer, is taken within 90 minutes after meals, that is 3 times a day for a total of 12 gm.<br>On Jul. 26, 1999, main symptoms have been improved.<br>On August 10, frequent micturition of little amount during the night.<br>On September 26, during the treatment course, hospitalization due to esophagus hemorrhage.<br>On October 9, hepatic index has dropped and platelet count has increased to normal.<br>On October 19, via a scan at Chang Gung Hospital, large tumor mass has gradually dispersed with the | 3 hepatoma masses, including two big ones of 6.0 cm and one small one of 1.8 cm, were detected with complication of liver cirrhosis. Thrombosis procedure was performed at Chang Gung Hospital. AFP level was normal with low platelet count and hepatic index of much too higher.<br><br><br><br><br><br><br><br>Determination of efficiency: significant efficiency<br>Filed on Mar. 15, 2002 |

-continued

| | |
|---|---|
| vanishment of small tumors. Hepatic function has been improved and maintained till the end of treatment. | |

| The practical subject in this clinical trial   No. 32 ||
|---|---|
| Cancer type: hepatoma<br>Original number of case: 98122514<br>The hospital making diagnosis: Kaohsiung Chang Gung Hospital<br>Hospital grade: regional (the 2$^{nd}$ grade)<br>Diagnosis method: CT and ultrasonic scan, and Angiography | Name of subject: Mr. Yong-Chin Liang<br>Date of birth: Dec. 25, 1947<br>Address: Chianjen District, Kaohsiung City<br><br>Date of diagnosis: April 1998<br>Place of hospital: Kaohsiung Hsien, Taiwan<br>Diagnosis: initially diagnosed at Tainan City Hospital and then confirmed and treated with thrombosis procedure at Chung Gung Hospital. |
| Condition before trial: | Precedent treatments and results |
| Main cancer-related symptoms:<br>Pain of the right costal region<br>Other minor symptoms:<br>Dizziness, fatigue, twice or three times of excretions in a day, and sleeping difficulty<br>This subject has enrolled into this trial since Dec. 25, 1998 till Apr. 10, 1999 for a total of 6 courses and 72 days.<br>Trial procedure:<br>The medication combination, specific for treating hepatoma and pancreatic cancer, is taken within 90 minutes after meals, that is 3 times a day for a total of 12 gm.<br>On Jan. 9, 1999, main symptoms were alleviated and then vanished on January 24.<br>On Feb. 13, all symptoms were disappeared with a normal hepatic index. Till the end of trial, he was in health condition. | Thrombosis procedures were performed 5 times at Chung Gung Hospital.<br><br><br><br><br><br><br><br><br><br>Determination of efficiency: with efficiency<br>Filed on Mar. 15, 2002 |

| The practical subject in this clinical trial   No. 33 ||
|---|---|
| Cancer type: hepatoma<br>Original number of case: 00091511<br>The hospital making diagnosis: Kaohsiung Chang Gung Hospital<br>Hospital grade: regional (the 2$^{nd}$ grade)<br>Diagnosis method: CT and ultrasonic scan and Angiography | Name of subject: Mrs. Shu-Fen Show<br>Date of birth: Jul. 30, 1963<br>Address: Sanmin Distric, Kaohsiung City<br><br>Date of diagnosis: March 2000<br>Place of hospital: Kaohsiung Hsien, Taiwan<br>Diagnosis: a tumor mass of 3 × 4 cm at the right liver lobe and × 3 of the left lobe. |
| Condition before trial: | Precedent treatments and results |
| Main cancer-related symptoms:<br>Occasional stuffiness of the right costal region and back and feeling empty and hungry of the stomach<br>Other minor symptoms:<br>Tiredness and lack of strength<br>This subject has enrolled into this trial since Sep. 16, 2000 till Nov. 15, 2000 for a total of 4.5 courses and 54 days.<br>Trial procedure:<br>The medication combination, specific for treating hepatoma and pancreatic cancer, is taken within 90 minutes after meals, that is 3 times a day for a total of 12 gm.<br>On September 27, main symptoms were alleviated and further alleviated on October 14.<br>On Nov. 3, 2000, via a scan at Chang Gung Hospital, the previous plugged tumor did not deteriorate anymore, no new tumor occurred and the small one disappeared. | After the confirmation of diagnosis, thrombosis procedure was performed for the tumor of 3 × 4 cm of the right lobe for 3 times.<br><br><br><br><br><br><br><br><br><br>Determination of efficiency: with efficiency<br>Filed on Mar. 15, 2002 |

| The practical subject in this clinical trial   No. 34 ||
|---|---|
| Cancer type: hepatoma<br>Original number of case: 01032803<br>The hospital making diagnosis: National Cheng Kung University Hospital<br>Hospital grade: teaching (the 1$^{st}$ grade) | Name of subject: Mrs. Yue-Li Chen<br>Date of birth: May 16, 0936<br>Address: Lioying, Tainan Hsien |

-continued

| | |
|---|---|
| Diagnosis method: CT and ultrasonic scan | Date of diagnosis: Mar. 26, 2001<br>Place of hospital: Tainan Hsien, Taiwan<br>Diagnosis: a tumor of 11 cm was detected by screening at Ming Sheng Clinic, Lioujia, and then confirmed by Cheng Kung University Hospital |
| Condition before trial: | Precedent treatments and results |
| Main cancer-related symptoms:<br>Swelling of large area at the right costal region and abdomen with occasional pain<br>Other minor symptoms:<br>Heart function difficulty, hypertension, burning pain of back chest, frequent micturition and constipation.<br>This subject has enrolled into this trial since Mar. 28, 2001 till Sep. 12, 2001.<br>Trial procedure:<br>The medication combination, specific for treating hepatoma and pancreatic cancer, is taken within 90 minutes after meals, that is 3 times a day for a total of 12 gm.<br>On Apr. 18, 2001, the swelling of right costal and abdominal region has gradually softened.<br>On May 30, 2001, the swelling of right costal and abdominal region has softened and contracted to only 1/2. At the end of trial, minor symptoms were alleviated due to medication administration, but relapsed soon after. The pain of the right costal and abdominal region has vanished. | Long usage of drugs for lowering blood pressure and sleeping pills.<br><br><br><br><br><br><br><br><br><br>Determination of efficiency: significant efficiency<br>Filed on Mar. 15, 2002 |
| The practical subject in this clinical trial No. 35 | |
| Cancer type: hepatoma<br>Original number of case: 99052201<br>The hospital making diagnosis: Pingtung Christian Hospital<br>Hospital grade: regional (the 2$^{nd}$ grade)<br>Diagnosis method: CT and ultrasonic scan | Name of subject: Mr. Zhi-Qing Chen<br>Date of birth: Aug. 26, 1945<br>Address: Pingtung City, Pingtung Hsien<br><br><br>Date of diagnosis: Mar. 18, 1999<br>Place of hospital: Pingtung City, Taiwan<br>Diagnosis: hepatoma |
| Condition before trial: | Precedent treatments and results |
| Main cancer-related symptoms:<br>A protruding tumor at the stomach, hard as stone and pain while touch and swelling of stomach<br>Other minor symptoms:<br>Sleepless, thirst and weakness of feet<br>This subject has enrolled into this trial since May 22, 1999 till Jun. 9, 1999 for a total of 4 courses and 48 days.<br>Trial procedure:<br>The medication combination, specific for treating hepatoma and pancreatic cancer, is taken within 90 minutes after meals, that is 3 times a day for a total of 12 gm.<br>On May 28, 1999, main symptoms were slightly alleviated and not much improved by following treatment. It was known later that patients have used alternative medication. | Transferred to Ren-Ai Hospital (the 3$^{rd}$ grade) for treatment and rechecked on May 15, 1999.<br><br><br><br><br><br><br><br><br>Determination of efficiency: undetermined<br>Filed on Mar. 15, 2002 |
| The practical subject in this clinical trial No. 36 | |
| Cancer type: hepatoma<br>Original number of case: 99051608<br>The hospital making diagnosis: Kaohsiung Chang Gung Hospital<br>Hospital grade: regional (the 2$^{nd}$ grade)<br>Diagnosis method: biopsy and CT and ultrasonic scan | Name of subject: Mrs. Hong-Yun Chen<br>Date of birth: Oct. 21, 1937<br>Address: Gangshan, Kaohsiung Hsien<br><br>Date of diagnosis: November, 1998<br>Place of hospital: Kaohsiung Hsien, Taiwan<br>Diagnosis: a big hepatoma of 3.0 cm and a small one of 2.0 cm, complicated with liver cirrhosis |
| Condition before trial: | Precedent treatments and results |
| Main cancer-related symptoms:<br>Swelling of stomach and abdomen, and occasional pain, which was more severe during the night<br>Other minor symptoms: | One thrombosis procedure and twice alcohol injections at Chang Gung Hospital |

-continued

| | |
|---|---|
| This subject has enrolled into this trial since May 16, 1999 till Sep. 8, 1999 for a total of 7 courses and 84 days. Trial procedure: The medication combination, specific for treating hepatoma and pancreatic cancer, is taken within 90 minutes after meals, that is 3 times a day for a total of 12 gm. On Jun. 20, 1999, via a CT scan at Chung Gung Hospital, intrahepatic tumor has shrunken, however, swelling of stomach and abdomen was alleviated till July 1. | Determination of efficiency: inefficiency Filed on Mar. 15, 2002 |

The practical subject in this clinical trial No. 37

| | |
|---|---|
| Cancer type: radical hepatoma Original number of case: 97080902 The hospital making diagnosis: Tainan City Hospital Hospital grade: regional (the $2^{nd}$ grade) Diagnosis method: biopsy, CT and ultrasonic scan, and Angiography | Name of subject: Mr. Ching-Rong Chen Date of birth: Apr. 15, 1927 Address: Annan District, Tainan City<br><br>Date of diagnosis: February 1997 Place of hospital: Tainan City, Taiwan Diagnosis: radical hepatoma and HBV carrier, similar diagnosis after treatment at Kaohsiung Medical University Hospital |
| Condition before trial: | Precedent treatments and results |
| Main cancer-related symptoms: Tiredness and fatigue, drowsy and insignificant main symptoms Other minor symptoms: Abnormality of prostate This subject has enrolled into this trial since Aug. 9, 1997 till Oct. 24, 1997 for a total of 5 courses and 60 days. Trial procedure: The medication combination, specific for treating hepatoma and pancreatic cancer, is taken within 90 minutes after meals, that is 3 times a day for a total of 12 gm. Main symptoms were insignificant and the alleviation of minor symptoms was not due to the effect of this trial medication (alternative medication was supplemented). This patient's vitality and physical strength were not improved. | Due to the senility and weakness of patient, the original hospital did not perform thrombosis procedure and then transferred to Kaohsiung Medical University Hospital for unknown treatment.<br><br><br><br><br><br>Determination of efficiency: inefficiency Filed on Mar. 15, 2002 |

The practical subject in this clinical trial No. 38

| | |
|---|---|
| Cancer type: hepatoma Original number of case: 97111608 The hospital making diagnosis: Kaohsiung Chang Gung Hospital Hospital grade: regional (the $2^{nd}$ grade) Diagnosis method: CT and ultrasonic scan, and Angiography | Name of subject: Mr. Chong-Kuang Chen Date of birth: Aug. 6, 1944 Address: Fengshan, Kaohsiung Hsien<br><br>Date of diagnosis: May 1997 Place of hospital: Kaohsiung Hsien, Taiwan Diagnosis: hepatoma, liver cirrhosis and HBV carrier, FPE was 696 while examined in 1997 |
| Condition before trial: | Precedent treatments and results |
| Main cancer-related symptoms: Slight pain of the right costal region and abdominal swelling Other minor symptoms: Frequent and yellowish urination of small amount, swelling of shin, and thirsty but not wanting drinking This subject has enrolled into this trial since Nov. 16, 1997 till Apr. 12, 1998 for a total of 10 courses and 120 days. Trial procedure: The medication combination, specific for treating hepatoma and pancreatic cancer, is taken within 90 minutes after meals, that is 3 times a day for a total of 12 gm On Nov. 30, 1997, pain of the right costal region has reduced but abdomen still swelled. On Jan. 24, 1998, all symptoms were improved with the vanishment of swelling of shin, but occasional pain occurred at shoulder, back and chest. | The patient worked at the $3^{rd}$ nuclear plant where 4 workers had diagnosed with cancer with 2 deaths in recent time. After the diagnosis, he stayed in the original hospital for thrombosis procedure and other necessary treatments.<br><br><br><br><br><br><br><br>Determination of efficiency: with efficiency Filed on Mar. 15, 2002 |

-continued

On Feb. 21, 1998, symptoms were improved.
On Mar. 7, 1998, alternative medication was taken
for function failure of heart.
On Mar. 28, 1998, slight pain of the right costal
region has vanished with significant improvement of
abdominal swelling. FPE was decreased to 232 (+).

The practical subject in this clinical trial No. 39

| | |
|---|---|
| Cancer type: hepatoma | Name of subject: Mr. Chi-Chang Chen |
| Original number of case: 97070922 | Date of birth: Aug. 30, 1932 |
| The hospital making diagnosis: Tainan Chi-Mei Hospital | Address: unknown |
| Hospital grade: regional (the 2$^{nd}$ grade) | |
| Diagnosis method: CT and ultrasonic scan and angiography | Date of diagnosis: January 1997 |
| | Place of hospital: Tainan City, Taiwan |
| | Diagnosis: a hepatoma of 12.5 cm |

| Condition before trial: | Precedent treatments and results |
|---|---|
| Main cancer-related symptoms: Tightness and pain of the right costal region, abdominal swelling and swelling of shin Other minor symptoms: Arrhythmia and frequent micturition during the night This subject has enrolled into this trial since Jul. 9, 1997 till Aug. 16, 1997 for a total of 3 courses and 36 days. Trial procedure: The medication combination, specific for treating hepatoma and pancreatic cancer, is taken within 90 minutes after meals, that is 3 times a day for a total of 12 gm. | After hospitalization at the original hospital for treatment, he was referred to Kaohsiung Chang Gung Hospital for thrombosis procedure and treatment in March 1997. |
| On Jul. 22, 1997, symptoms of tightness and pain of the right costal region and abdominal swelling were alleviated. On Aug. 2, 1997, main symptoms were significantly improved. | Determination of efficiency: with efficiency Filed on Mar. 15, 2002 |

The practical subject in this clinical trial No. 40

| | |
|---|---|
| Cancer type: hepatoma (metastasized from colon) | Name of subject: Mrs. Show-Ying Chen |
| Original number of case: 97081426 | Date of birth: Aug. 20, 1948 |
| The hospital making diagnosis: Taichung Veteran General Hospital | Address: N. District, Taichung |
| Hospital grade: regional (the 2$^{nd}$ grade) | |
| Diagnosis method: biopsy, CT and ultrasonic scan and angiography | Date of diagnosis: January 1994 |
| | Place of hospital: Taichung City, Taiwan |
| | Diagnosis: after dissection and chemotherapy, colon cancer metastasized to liver and then to ovary. |

| Condition before trial: | Precedent treatments and results |
|---|---|
| Main cancer-related symptoms: Occasional sudden pain of the right costal region and occasional illness of lower abdomen Other minor symptoms: Weakness | After dissection cancer and chemotherapy of colon cancer at Veteran General Hospital, cancer was metastasized to liver. After ineffective chemotherapy, cancer was metastasized to ovary. She has been treated at China Medical College Hospital and Taichung Ren-Ai Hospital. |
| This subject has enrolled into this trial since Aug. 14, 1997 till Sep. 22, 1997 for a total of 3.5 courses and 42 days. Trial procedure: The medication combination, specific for treating hepatoma and pancreatic cancer, is taken within 90 minutes after meals, that is 3 times a day for a total of 12 gm. | |
| On Aug. 19, 1997, main symptoms were alleviated. On Sep. 4, 1997, main symptoms were further alleviated. | Determination of efficiency: with efficiency Filed on Mar. 15, 2002 |

The practical subject in this clinical trial No. 41

| | |
|---|---|
| Cancer type: hepatoma | Name of subject: Mrs. Shu-Nv Chen |
| Original number of case: 01061306 | Date of birth: Nov. 11, 1942 |
| The hospital making diagnosis: Taichung Veteran General Hospital | Address: Guosing, Nantou Hsien |
| Hospital grade: regional (the 2$^{nd}$ grade) | |

| | |
|---|---|
| | -continued |
| Diagnosis method: CT and ultrasonic scan and angiography | Date of diagnosis: Feb. 15, 2001<br>Place of hospital: Taichung City, Taiwan<br>Diagnosis: hepatoma |
| Condition before trial: | Precedent treatments and results |
| Main cancer-related symptoms:<br>Hard swelling of the right costal region, as well as right abdomen, swelling hard as stone of stomach, belch, and fever around nightfall<br>Other minor symptoms: tiredness and fatigue, subclinical jaundice, yellowish micturition during night, and lost of appetite<br>This subject has enrolled into this trial since Jun. 13, 2001 till Oct. 3, 2001 in a total of 10 courses and 120 days.<br>Trial procedure:<br>The medication combination, specific for treating hepatoma and pancreatic cancer, is taken within 90 minutes after meals, that is 3 times a day for a total of 12 gm.<br>On Jun. 27, 2001, abdominal swelling was alleviated during the night.<br>On July 11, hard swelling of the right costal region has softened and dispersed.<br>On Aug. 8, 2001, tumor of stomach has dispersed for over 1/3 and nightfall fever has vanished | Thrombosis procedures were performed at the original hospital after diagnosis.<br><br><br><br><br><br><br><br><br>Determination of efficiency: with efficiency<br>Filed on Mar. 15, 2002 |
| The practical subject in this clinical trial   No. 42 | |
| Cancer type: hepatoma<br>Original number of case: 98041902<br>The hospital making diagnosis: Pingtung Christian Hospital.<br>Hospital grade: regional (the 2$^{nd}$ grade)<br>Diagnosis method: CT and ultrasonic scan and angiography | Name of subject: Mr. Jin-Qian Chen<br>Date of birth: Mar. 22, 1959<br>Address: Changjr, Pingtung Hsien<br><br><br>Date of diagnosis: Apr. 2, 1998<br>Place of hospital: Pingtung Hsien, Taiwan<br>Diagnosis: hepatoma and liver cirrhosis |
| Condition before trial: | Precedent treatments and results |
| Main cancer-related symptoms:<br>Occasional pain of the right costal region, abdominal swelling and swelling of shin<br>Other minor symptoms:<br>Gastric ulcer, tiredness and lack of strength, and yellow-brownish facial skin, slight swelling edema, and normal urination and excretion<br>This subject has enrolled into this trial since Apr. 19, 1998 till Apr. 15, 1999 for total of 20 courses and 240 days.<br>Trial procedure:<br>The medication combination, specific for treating hepatoma and pancreatic cancer, is taken within 90 minutes after meals, that is 3 times a day for a total of 12 gm.<br>On May 1, 1998, the main symptoms have been improved<br>On May 13, 1998, the liver tumor was dispersed as seen in scan.<br>On May 26, 1998, gastric ulcer has been amended.<br>On Jul. 23, 1998, main symptoms were significantly alleviated or vanished.<br>On Nov. 1, intestinal hemorrhage occurred, as well as insufficient platelet.<br>Since Dec. 27, 1998, all symptoms have all vanished and his spirit and physical strength were better. | After confirmation of diagnosis, he was transferred to Dunggang An-Tai hospital on April 9 for thrombosis procedure.<br><br><br><br><br><br><br><br><br><br><br>Determination of efficiency: significant efficiency, efficiency, no efficiency and undetermined<br>Filed on Mar. 15, 2002 |
| The practical subject in this clinical trial   No. 43 | |
| Cancer type: hepatoma<br>Original number of case: 01080801<br>The hospital making diagnosis: Chunghua Christian Hospital | Name of subject: Mrs. Pao-Zhu Chen<br>Date of birth: Dec. 17, 1939<br>Address: Beitou, Chunghua Hsien |

-continued

| | |
|---|---|
| Hospital grade: regional (the 2nd grade)<br>Diagnosis method: CT and ultrasonic scan and angiography | Date of diagnosis: March 2001<br>Place of hospital: Chunghua Hsien, Taiwan<br>Diagnosis: a hepatoma of 5.2 cm complicated with hepatitis C infection |
| Condition before trial: | Precedent treatments and results |
| Main cancer-related symptoms:<br>Hardness of stomach and left spleen, pain of the right costal and abdominal region, swelling and belching<br>Other minor symptoms:<br>3 or 4 times of excretions after taking laxative, micturition of small amount with difficulty, and swelling of shin<br>This subject has enrolled into this trial since Aug. 8, 2001 till Sep. 24, 2001 for a total of 4 courses and 48 days.<br>Trial procedure:<br>The medication combination, specific for treating hepatoma and pancreatic cancer, is taken within 90 minutes after meals, that is 3 times a day for a total of 12 gm.<br>On August 16, main symptoms were alleviated.<br>On Aug. 31, 2001, due to the administration of western medicines for cold and long term diarrhea, her spleen has been damaged. A hepatoma of 6.5 cm was detected via scan and the trial medication was continuously taken for 24 days. No follow-up report was available. | At the original hospital, she has been through one thrombosis procedure on March 19, another on May 15 and a alcohol chemotherapy on July 25.<br><br><br><br><br><br><br><br><br><br>Determination of efficiency: inefficiency<br>Filed on Mar. 15, 2002 |

| The practical subject in this clinical trial   No. 44 | |
|---|---|
| Cancer type: hepatoma<br>Original number of case: 99111103<br>The hospital making diagnosis: Kaohsiung Ruan Surgical General Hospital<br>Hospital grade: regional (the 2nd grade)<br>Diagnosis method: CT and ultrasonic scan | Name of subject: Mr. Guo Shiong Chen<br>Date of birth: Mar. 25, 1962<br>Address: Chianjen District, Kaohsiung City<br><br><br>Date of diagnosis: March 1997<br>Place of hospital: Kaohsiung City, Taiwan<br>Diagnosis: diagnosed in March 1997 by Ruan Surgical General Hospital and had a thrombosis procedure on Oct. 20, 1999 and then scanned again at Min-Sheng Hospital. |
| Condition before trial: | Precedent treatments and results |
| Main cancer-related symptoms:<br>Occasional pain of the right costal region and abdominal swelling<br>Other minor symptoms:<br>Yellowish normal urination, lost of appetite and 2 or 3 times of excretion in a day<br>This subject has enrolled into this trial since Nov. 11, 1999 till Jan. 25, 2000 for a total of 4 courses and 48 days.<br>Trial procedure:<br>The medication combination, specific for treating hepatoma and pancreatic cancer, is taken within 90 minutes after meals, that is 3 times a day for a total of 12 gm.<br>On November 25, the pain of the right costal region has alleviated and the swelling of stomach has vanished.<br>On December 2, the pain of the right costal region and the swelling of stomach have vanished.<br>The scan performed on January 13 of 2000 has shown that the recurred tumor mass of 3.7 cm has significant reduced with no sign of tumor cells. | A recurrence hepatoma of 3.7 cm together with carcinoma and a previous gastric hemorrhage on Oct. 20, 1999.<br><br><br><br><br><br><br><br><br><br><br>Determination of efficiency: significant efficiency<br>Filed on Mar. 15, 2002 |

| The practical subject in this clinical trial   No. 45 | |
|---|---|
| Cancer type: intrahepatic bile duct cancer<br>Original number of case: 99040216<br>The hospital making diagnosis: Kaohsiung Veteran General Hospital<br>Hospital grade: regional (the 2nd grade)<br>Diagnosis method: CT and ultrasonic scan | Name of subject: Mr. Ming-Zhu Zhuang<br>Date of birth: Mar. 2, 1935<br>Address: Tzuoying District, Kaohsiung City<br><br><br>Date of diagnosis: Apr. 1, 1999<br>Place of hospital: Ksohsiung City, Taiwan |

-continued

| | Diagnosis: a total of 3 intrahepatic bile duct tumor with a big one of 3.4 cm |
|---|---|
| Condition before trial: | Precedent treatments and results |
| Main cancer-related symptoms:<br>Complaints of heart and the right costal areas and swelling of stomach (hypertrophy of veins)<br>Other minor symptoms:<br>Headache, facial edema, tiredness and fatigue, micturition of small amounts, skin itchiness and impotence of heart<br>This subject has enrolled into this trial since Apr. 2, 1999 till Jul. 7, 1999.<br>Trial procedure:<br>The medication combination, specific for treating hepatoma and pancreatic cancer, is taken within 90 minutes after meals, that is 3 times a day for a total of 12 gm.<br>On Apr. 15, 1999, main symptoms have alleviated with a slow heartbeat.<br>On Apr. 27, 1999, main symptoms have vanished with a better facial color and vitality.<br>The trial medication was continuously taken after May 1, 1999, although a thrombosis procedure was performed (which was known thereafter) which was unrelated to this trial. | After direct enrollment into this trial, his condition has improved after 3 courses. However, some of his family has disobeyed the trial regulation to refer him to thrombosis procedures.<br><br>Before trial, his AFP value was 38.9 with a liver tumor of 3.4 cm.<br>On May 4 (after 2 courses), his AFP has dropped to 26.6 and the size of tumor has shrunken to 2.7 cm.<br><br>Determination of efficiency: with efficiency<br>Filed on Mar. 15, 2002 |

| The practical subject in this clinical trial No. 46 | |
|---|---|
| Cancer type: hepatoma<br>Original number of case: 97112112<br>The hospital making diagnosis: Pingtung Christian Hospital<br>Hospital grade: regional (the 2$^{nd}$ grade)<br>Diagnosis method: CT and ultrasonic scan | Name of subject: Mr. Shu-Shun Zhuang<br>Date of birth: 1938<br>Address: Yanpu, Pingtung Hsien<br><br>Date of diagnosis: October 1997<br>Place of hospital: Pingtung Hsien, Taiwan<br>Diagnosis: hepatoma and liver cirrhosis |
| Condition before trial: | Precedent treatments and results |
| Main cancer-related symptoms:<br>Pain of the right costal region and swelling of stomach<br>Other minor symptoms:<br>Tiredness and fatigue, yellowish micturition of small amounts<br>This subject has enrolled into this trial since Nov. 21, 1997 till Sep. 5, 1998 for a total of 14 courses and 168 days.<br>Trial procedure:<br>The medication combination, specific for treating hepatoma and pancreatic cancer, is taken within 90 minutes after meals, that is 3 times a day for a total of 12 gm.<br>On December 3, main symptoms were significantly alleviated.<br>On December 17, symptoms were further improved and the pain of the right costal region has vanished.<br>On Jan. 1, 1998, main symptoms have vanished without any recurrence before the end of trial. | Directly enrolled into this trial<br><br><br>In February, 1999, the main symptoms occasionally occurred, which have vanished after a further 3 courses of treatments.<br><br><br>Determination of efficiency: significant efficiency<br>Filed on Mar. 15, 2002 |

| The practical subject in this clinical trial No. 47 | |
|---|---|
| Cancer type: hepatoma<br>Original number of case: 01061501<br>The hospital making diagnosis: Kaohsiung Chang Gung Hospital<br>Hospital grade: regional (the 2$^{nd}$ grade)<br>Diagnosis method: biopsy, CT and ultrasonic scan and angiography | Name of subject: Mrs. Ying Shu<br>Date of birth: 1939<br>Address: Daliau, Kaohsiung Hsien<br><br>Date of diagnosis: June, 1998<br>Place of hospital: Kaohsiung Hsien, Taiwan<br>Diagnosis: hepatoma, liver cirrhosis and hepatitis C infection |
| Condition before trial: | Precedent treatments and results |
| Main cancer-related symptoms:<br>Pain of the right costal region, abdominal swelling, difficulty in excretion and urination, swelling of shin | After confirmation of diagnosis, serial alcohol chemotherapies were performed at the original hospital, together with 4 thrombosis procedures. |

-continued

| | |
|---|---|
| and bleeding of gums<br>Other minor symptoms:<br>Darken facial color, tiredness and fatigue, weakness of the upper eyelids, high fever during the night<br>This subject has enrolled into this trial since Jun. 15, 2001 till Oct. 11, 2001 for a total of 6 courses and 72 days.<br>Trial procedure:<br>The medication combination, specific for treating hepatoma and pancreatic cancer, is taken within 90 minutes after meals, that is 3 times a day for a total of 12 gm.<br>On Jul. 10, 2001, during the 2$^{nd}$ course, main symptoms have significantly improved, so did the minor symptoms. However, due to the family matters, mediation was stopped for 45 days.<br>On Sep. 11, 2001, pain of the right costal region has vanished, urination difficulty and shin swelling have improved, and however, abdominal swelling and excretion difficulty was not changed. Till the end of treatment, pain of the right costal region did not recur and main symptoms were improved, however, his vitality and physical strength were not significantly improved. | However, the condition was not improved.<br><br><br><br><br><br><br><br><br><br>Determination of efficiency: with efficiency<br>Filed on Mar. 15, 2002 |

The practical subject in this clinical trial No. 48

| | |
|---|---|
| Cancer type: hepatoma<br>Original number of case: 01040402<br>The hospital making diagnosis: Cheng Kung University Hospital<br>Hospital grade: teaching (the 1$^{st}$ grade)<br>Diagnosis method: nuclear examination and CT and ultrasonic scan | Name of subject: Mr. Yi-Wan Chang<br>Date of birth: May 19, 1940<br>Address: Chigu, Tainan Hsien<br><br>Date of diagnosis: Apr. 9, 2001<br>Place of hospital: Tainan City, Taiwan<br>Diagnosis: a hepatoma of 3.0 cm, liver cirrhosis and diabetes |
| Condition before trial: | Precedent treatments and results |
| Main cancer-related symptoms:<br>Stuffy pain of the right costal region, abdominal swelling and swelling of shin<br>Other minor symptoms:<br>Sleepless, micturition of small amounts, skin itchiness, 6 or 7 times of excretion in a day and diarrhea<br>This subject has enrolled into this trial since Apr. 28, 2001 till Aug. 9, 2001 for a total of 8 courses and 96 days.<br>Trial procedure:<br>The medication combination, specific for treating hepatoma and pancreatic cancer, is taken within 90 minutes after meals, that is 3 times a day for a total of 12 gm.<br>During the 1$^{st}$ and 2$^{nd}$ courses, main symptoms have significantly improved, however, after June 9, the condition was fluctuant and unstable.<br>One Jul. 21, 2001, via the examination at Taiwan University Hospital, cancer metastasis was found on both sides of liver, therefore, this case was classified as not efficient. | After confirmation of diagnosis at Cheng Kung University Hospital, he was hospitalized at Chi-Mei Hospital and has taken folk prescriptions, which resulted in his diarrhea.<br><br><br><br><br><br><br><br>Determination of efficiency: inefficiency<br>Filed on Mar. 15, 2002 |

The practical subject in this clinical trial No. 49

| | |
|---|---|
| Cancer type: hepatoma<br>Original number of case: 97060738<br>The hospital making diagnosis: Kaohsiung Medical University Hospital<br>Hospital grade: teaching (the 1$^{st}$ grade)<br>Diagnosis method: CT and ultrasonic scan | Name of subject: Mr. Wen-Tai Zeng<br>Date of birth: 1954<br>Address: Gangshan, Kaohsiung Hsien<br><br>Date of diagnosis: Sep. 15, 2000<br>Place of hospital: Kaohsiung Hsien, Taiwan<br>Diagnosis: 3 hepatoma masses and liver cirrhosis |
| Condition before trial: | Precedent treatments and results |
| Main cancer-related symptoms:<br>Pain of the right costal region and abdominal swelling<br>Other minor symptoms:<br>Sleepless, tiredness and fatigue, difficulty of | On October 25, after the 1$^{st}$ course of treatment, thrombosis procedure was performed at Kaohsiung Medical University Hospital. |

-continued

| | |
|---|---|
| urination, spontaneous sweating, sprain of limbs and 3 times of excretion in a day.<br>This subject has enrolled into this trial since Sep. 16, 2000 till Oct. 26, 2001.<br>Trial procedure:<br>The medication combination, specific for treating hepatoma and pancreatic cancer, is taken within 90 minutes after meals, that is 3 times a day for a total of 12 gm.<br>During the 1$^{st}$ course, symptoms were alleviated, however, after a thrombosis procedure at Kaohsiung Medical University Hospital on October 25; the condition was deteriorated and not improved by medication or chemotherapy.<br>On November 23, medication for an half course was given.<br>He was back to this trial on Mar. 22, 2001. | On Apr. 3, 2001, after the re-disappearance of main symptoms, trial medication was taken on and off till the end of trial and main symptoms did not recur.<br><br>Determination of efficiency: with efficiency<br>Filed on Mar. 15, 2002 |

| The practical subject in this clinical trial   No. 50 | |
|---|---|
| Cancer type: hepatoma<br>Original number of case: 97071602<br>The hospital making diagnosis: Pingtung Ren-Ai Hospital<br>Hospital grade: general (the 3$^{rd}$ grade)<br>Diagnosis method: biopsy and CT and ultrasonic scan | Name of subject: Mr. Guo-Ke Zeng<br>Date of birth: Sep. 3, 1928<br>Address: Shinbei, Pingtung Hsien<br><br>Date of diagnosis: March 1997<br>Place of hospital: Pingtung Hsien, Taiwan<br>Diagnosis: hepatoma and recurrence after chemotherapy |
| Condition before trial: | Precedent treatments and results |
| Main cancer-related symptoms:<br>Abdominal swelling and occasional pain around the navel<br>Other minor symptoms:<br>Tiredness and fatigue, lost of appetite, and difficulty in excretion<br>This subject has enrolled into this trial since Jul. 16, 1997 till Sep. 2, 1998 for a total of 28 courses and 336 days.<br>Trial procedure:<br>The medication combination, specific for treating hepatoma and pancreatic cancer, is taken within 90 minutes after meals, that is 3 times a day for a total of 12 gm.<br>On Aug. 13, 1997, during the 2$^{nd}$ course, man symptoms were significantly alleviated and minor symptoms were nearly disappeared. During the 4$^{th}$ course, all symptoms were disappeared.<br>Based on the recurrence of symptoms after the last chemotherapy, the trial medication was continuously taken with occasional abdominal swelling. | After confirmative diagnosis at Kaohsiung Chang Gung Hospital in 1995, unknown treatment was given. In March 1997, after scanning at Ren-Ai Hospital, chemotherapy was performed but the condition deteriorated with abdominal swelling and a AFP of 350.<br>Symptoms, including vomiting, belching and accidiental erysipelas, were cured with administration of this trial medication, sometime supplemented with alternative drugs. Till the end of this trial, hepatic function was normal with no recurrence of abdominal swelling.<br><br>Determination of efficiency: significant efficiency<br>Filed on Mar. 15, 2002 |

| The practical subject in this clinical trial   No. 51 | |
|---|---|
| Cancer type: hepatoma<br>Original number of case: 98120104<br>The hospital making diagnosis: Linko Chang Gung Hospital<br>Hospital grade: teaching (the 1$^{st}$ grade)<br>Diagnosis method: biopsy and CT and ultrasonic scan | Name of subject: Mrs. Jia-He Zeng<br>Date of birth: Jan. 5, 1940<br>Address: Shinpu, Hsinchu Hsien<br><br>Date of diagnosis: November 1998<br>Place of hospital: Taipei Hsien, Taiwan<br>Diagnosis: hepatoma |
| Condition before trial: | Precedent treatments and results |
| Main cancer-related symptoms:<br>Stomach pain with 2 masses, hard as stone, and pain at one side of abdomen<br>Other minor symptoms:<br>Bitterness and thirst of mouth, lost of appetite, 3 or 4 times of excretion in a day and difficulty of urination<br>This subject has enrolled into this trial since Dec. 1, 1998 till Jan. 13, 1999 for a total of 3 courses and 36 days.<br>Trial procedure:<br>The medication combination, specific for treating hepatoma and pancreatic cancer, is taken within 90 | After confirmative diagnosis, thrombosis procedure was performed and health food, Ginseng powder, was taken (which was known afterwards) |

-continued

| | |
|---|---|
| minutes after meals, that is 3 times a day for a total of 12 gm.<br>On Dec. 16, 1999, during the first course, the tumor mass has dispersed for 1/3 and his vitality and strength has been improved.<br>On Jan. 1, 1999, he violated the contradiction by taking food that increased blood pressure of the portal vein and therefore, resulted in an extreme abdominal swelling, which was unrelated to this trial medication. | Determination of efficiency: with efficiency<br>Filed on Mar. 15, 2002 |

| The practical subject in this clinical trial   No. 52 | |
|---|---|
| Cancer type: hepatoma with metastasis<br>Original number of case: 98111206<br>The hospital making diagnosis: Kaohsiung Ruan Surgical General Hospital<br>Hospital grade: regional (the 2$^{nd}$ grade)<br>Diagnosis method: biopsy and CT and ultrasonic scan | Name of subject: Mr. Rui-Feng Ye<br>Date of birth: Aug. 20, 1957<br>Address: Chijin District, Kaohsiung City<br><br>Date of diagnosis: September 1998<br>Place of hospital: Kaohsiung City, Taiwan<br>Diagnosis: hepatoma, liver cirrhosis, higher hepatic index, a blood sugar AC of 152 and Gout |
| Condition before trial: | Precedent treatments and results |
| Main cancer-related symptoms:<br>Stomach swelling, pain of the right costal region and stuffiness of chest<br>Other minor symptoms:<br>Darken facial skin, skinny, tiredness and fatigue, yellowish micturition of small amounts and swelling of shin<br>This subject has enrolled into this trial since Nov. 12, 1998 till Nov. 6, 1999 for a total of 16 courses and 192 days.<br>Trial procedure:<br>The medication combination, specific for treating hepatoma and pancreatic cancer, is taken within 90 minutes after meals, that is 3 times a day for a total of 12 gm.<br>On Nov. 24, 1998, all symptoms were alleviated but feet tendons were occasionally suffered from sprain.<br>On Dec. 26, 1998, symptoms were further alleviated but with gout at feet.<br>On Jan. 9, 1999, all symptoms were nearly vanished, together with normal hepatic index and vanishment of complication. | After hospitalization at the original hospital, his condition continuously deteriorated with a hepatic index higher than normal.<br><br>During the examination at Ruan Surgical General Hospital on March 9, the metastasized site was calcified and the original tumor was under control.<br>During the follow-up at Ruan Surgical General Hospital in August 1999, intrahepatic spot was detected but without any sign of cancer cells via biopsy. Digestive tracts were normal as checked by laparoscopy.<br>Determination of efficiency: significant efficiency<br>Filed on Mar. 15, 2002 |

| The practical subject in this clinical trial   No. 53 | |
|---|---|
| Cancer type: hepatoma<br>Original number of case: 97030402<br>The hospital making diagnosis: Cheng Kung University Hospital<br>Hospital grade: teaching (the 1$^{st}$ grade)<br>Diagnosis method: CT and ultrasonic scan | Name of subject: Mr. Tian-Cai Huang<br>Date of birth: Sep. 22, 1929<br>Address: Lioujia, Tainan Hsien<br><br>Date of diagnosis: Feb. 20, 1997<br>Place of hospital: Tainan City, Taiwan<br>Diagnosis: hepatoma with metastasis to lung |
| Condition before trial: | Precedent treatments and results |
| Main cancer-related symptoms:<br>Pain at the lower right costal region and abdominal swelling<br>Other minor symptoms:<br>Tiredness and fatigue, excretion difficulty, micturition, weakness and movement difficulty<br>This subject has enrolled into this trial since Mar. 4, 1997 till May 6, 1997 for a total of 4.5 courses and 54 days.<br>Trial procedure:<br>The medication combination, specific for treating hepatoma and pancreatic cancer, is taken within 90 minutes after meals, that is 3 times a day for a total of 12 gm.<br>On Mar. 15, 1997, symptoms were significantly alleviated and able to walk independently to Activity Center of Senior. Since he was asked to stop medication for anesthesia, he has experienced | Peaceful managements, such as anesthesia and pain killing, were adopted by the original hospital.<br><br><br><br><br><br><br><br><br><br><br><br><br><br>Determination of efficiency: significantly efficiency<br>Filed on Mar. 15, 2002 |

| -continued |  |
|---|---|
| palpitation, vomiting and yawning in the first 3 or 4 days.<br>On Mar. 29, 1997, pain of the lower right costal region has vanished, so did the abdominal swelling, without any recurrence | |

| The practical subject in this clinical trial No. 54 | |
|---|---|
| Cancer type: hepatoma<br>Original number of case: 98012708<br>The hospital making diagnosis: Pingtung Christian Hospital<br>Hospital grade: regional (the 2$^{nd}$ grade)<br>Diagnosis method: CT and ultrasonic scan | Name of subject: Mrs. Mei-Huei Huang<br>Date of birth: Sep. 8, 1951<br>Address: Yanpu, Pingtung Hsien<br><br>Date of diagnosis: December 1997<br>Place of hospital: Pingtung Hsien, Taiwan<br>Diagnosis: a hepatic angioma of 5.0 cm |
| Condition before trial: | Precedent treatments and results |
| Main cancer-related symptoms:<br>Pain of the right costal region and no hungry feeling of stomach<br>Other minor symptoms: tiredness and fatigue, yellowish-pale facial skin, dryness and bitterness of mouth, sleepless, unsolidified stool and micturition<br>This subject has enrolled into this trial since Jan. 24, 1998 till Aug. 5, 1998 for a total of 11.5 courses and 138 days.<br>Trial procedure:<br>The medication combination, specific for treating hepatoma and pancreatic cancer, is taken within 90 minutes after meals, that is 3 times a day for a total of 12 gm.<br>On Feb. 13, 1998, symptoms were alleviated.<br>On Feb. 26, 1998, symptoms have vanished except the occasional pain of the right costal region.<br>On Mar. 18, 1998, via a scan at the original hospital, intrahepatic tumor has shrunken. No symptoms recurred before the end of trial. The patient's vitality and strength were as normal and able to work at the beginning of April (he was a building worker) | Folk prescriptions with a nature of cold have been taken which were harmful for spleen and therefore led to diarrhea.<br><br><br><br><br><br><br><br><br><br>Determination of efficiency: significant efficiency<br>Filed on Mar. 15, 2002 |

| The practical subject in this clinical trial No. 55 | |
|---|---|
| Cancer type: hepatoma<br>Original number of case: 01011409<br>The hospital making diagnosis: Chi-Mei Hospital, Tainan<br>Hospital grade: regional (the 2$^{nd}$ grade)<br>Diagnosis method: biopsy and CT and ultrasonic scan | Name of subject: Mrs. Qiu-Yue Huang<br>Date of birth: Sep. 14, 1935<br>Address: Shinshing District, Kaohsiung City<br><br>Date of diagnosis: July 2000<br>Place of hospital: Tainan City, Taiwan<br>Diagnosis: 5 tumor mass of hepatoma |
| Condition before trial: | Precedent treatments and results |
| Main cancer-related symptoms:<br>Pain of the right costal region, sharp pain from right waist, hip to foot, abdominal pain and swelling, urination difficulty, and swelling of shin<br>Other minor symptoms:<br>Weakness, movement difficulty, lost of appetite, sleepless and constipation with twice excretions a day.<br>This subject has enrolled into this trial since Jan. 14, 2001 till February 26 for a total of 3 courses and 36 days.<br>Trial procedure:<br>The medication combination, specific for treating hepatoma and pancreatic cancer, is taken within 90 minutes after meals, that is 3 times a day for a total of 12 gm.<br>On Jan. 31, 2001, during the treatment course, swelling was gradually dispersed and pain of the right costal region reduced, however, due to the eagerness of family and unbearable sharp pain from right waist, hip to foot, she still went back to Ruan Surgical | After confirmative diagnosis at Chi-Mei Hospital in July, 2000, thrombosis procedure was performed right after. She was transferred to Ruan Surgical General Hospital in August for a treatment of 14 days. After discharged from the hospital, she has taken Chinese medicines, which led to deterioration and swelling. She was admitted into Ruan Surgical General Hospital again to treatment till Jan. 17, 2001.<br><br><br><br><br><br><br><br>Determination of efficiency: undetermined<br>Filed on Mar. 15, 2002 |

-continued

| | |
|---|---|
| General Hospital for anesthesia treatment during the treatment course. Therefore, the trial medication could not exert the full effect. | |

| The practical subject in this clinical trial No. 56 | |
|---|---|
| Cancer type: liver carcinoma<br>Original number of case: 99080108<br>The hospital making diagnosis: Kaohsiung Medical University Hospital<br>Hospital grade: teaching (the 1$^{st}$ grade)<br>Diagnosis method: CT and ultrasonic scan | Name of subject: Mr. Wu-Shiong Huang<br>Date of birth: Nov. 29, 1939<br>Address: Fengshan, Kaohsiung Hsien<br><br>Date of diagnosis: March 1994<br>Place of hospital: Kaohsiung City, Taiwan<br>Diagnosis: liver carcinoma complicated with hepatitis B, hepatitis C, uremia, diabetes and hypertension |
| Condition before trial: | Precedent treatments and results |
| Main cancer-related symptoms:<br>Stuffiness of chest with sputum, abdominal swelling and occasional pain of the right costal region<br>Other minor symptoms:<br>Lost of appetite, usual constipation, micturition, swelling of shin, sleepless, waist ache and dizziness<br>This subject has enrolled into this trial since Aug. 1, 1999 till Apr. 21, 2001 for a total of 44 courses and 528 days.<br>Trial procedure:<br>The medication combination, specific for treating hepatoma and pancreatic cancer, is taken within 90 minutes after meals, that is 3 times a day for a total of 12 gm.<br>After long-term thrombosis procedure, patient's condition was unique and complicated. However, main symptoms were partially alleviated and AFP was stably maintained, which could support the efficiency of this trial medication on hepatoma. Furthermore, new tumor mass appeared at less than 90 days after the previous thrombosis procedure. However, another new tumor mass was found as late as Nov. 5, 2000, which was as far as 450 days after Aug. 1, 1999, the date of starting the trial. This could further support the efficiency on this case. | Alcohol chemotherapy or thrombosis procedure was performed at Kaohsiung Medical University Hospital in 1994. However, after less than 90 days, another tumor recurred and complicated with other conditions, such as uremia (tumor size about 1.0 cm).<br><br><br><br><br><br><br><br>Determination of efficiency: with efficiency<br>Filed on Mar. 15, 2002 |

| The practical subject in this clinical trial No. 57 | |
|---|---|
| Cancer type: hepatoma<br>Original number of case: 97083102<br>The hospital making diagnosis: Ksohsiung Chang Gung Hospital<br>Hospital grade: regional (the 2$^{nd}$ grade)<br>Diagnosis method: biopsy and CT and ultrasonic scan | Name of subject: Mr. Jin-Fu Huang<br>Date of birth: Feb. 20, 1932<br>Address: Chaujou, Pingtung Hsien<br><br>Date of diagnosis: Aug. 14, 1997<br>Place of hospital: Kaohsiung Hsien, Taiwan<br>Diagnosis: malignant multiple hepatoma, complicated with diabetes and hepatitis B. |
| Condition before trial: | Precedent treatments and results |
| Main cancer-related symptoms:<br>Sharp and sudden pain of the right costal region, and abdominal swelling<br>Other minor symptoms: excretion difficulty, reddish micturition, tiredness and fatigue, sleepiness, thirst and high fever<br>This subject has enrolled into this trial since Aug. 31, 1997 till Nov. 6, 1997 for a total of 5 courses and 60 days.<br>Trial procedure:<br>The medication combination, specific for treating hepatoma and pancreatic cancer, is taken within 90 minutes after meals, that is 3 times a day for a total of 12 gm.<br>On Sep. 12, 1997, during the 1$^{st}$ course, main symptoms were significantly alleviated. Thereafter, he admitted into Tian-Suen Hospital due to the high fever and ache. After administration of this | Unknown<br><br><br><br><br><br><br><br><br><br><br><br><br><br>Determination of efficiency: inefficiency<br>Filed on Mar. 15, 2002 |

-continued

| | |
|---|---|
| medication, his vitality and appetite were better and therefore continued for 1 course. In following, he has taken another 2 courses with no further improvement. | |

| The practical subject in this clinical trial No. 58 ||
|---|---|
| Cancer type: hepatoma<br>Original number of case: 97082002<br>The hospital making diagnosis: Ksohsiung Chang Gung Hospital<br>Hospital grade: regional (the $2^{nd}$ grade)<br>Diagnosis method: CT and ultrasonic scan | Name of subject: Mr. Ching-Ke Huang<br>Date of birth: Oct. 26, 1935<br>Address: Yanshuei, Tainan Hsien<br><br>Date of diagnosis: May 1997<br>Place of hospital: Kaohsiung Hsien, Taiwan<br>Diagnosis: a hepatoma mass of 5.0 cm, liver cirrhosis, hepatitis B carrier and complications of coughing and gasping (bronchitis) |
| Condition before trial: | Precedent treatments and results |
| Main cancer-related symptoms:<br>Pain of the lower edge of right costal region and occasional chest pain<br>Other minor symptoms: tiredness and fatigue, night cough and gasp, sleepless, sweating, and micurition<br>This subject has enrolled into this trial since Aug. 20, 1997 till Jan. 10, 1998 for a total of 12 courses and 144 days.<br>Trial procedure:<br>The medication combination, specific for treating hepatoma and pancreatic cancer, is taken within 90 minutes after meals, that is 3 times a day for a total of 12 gm.<br>On Aug. 31, 1997, pain of the lower edge of right costal region and chest pain have alleviated.<br>On Sep. 26, 1999, main symptoms have vanished.<br>Although minor symptoms, such as gasping and coughing, were not relieved, none main symptoms recurred before the end of trial. Even the occasional pain happened which could be relieved right after the administration of the trial medication. | Unknown and a hepatoma of 6.0 cm was scanned at Wang Kuo Chin Clinical in August 1997.<br><br><br><br><br><br><br><br>Determination of efficiency: with efficiency<br>Filed on Mar. 15, 2002 |

| The practical subject in this clinical trial No. 59 ||
|---|---|
| Cancer type: hepatoma<br>Original number of case: 99042312<br>The hospital making diagnosis: Chiai St. Martin<br>Hospital grade: regional (the $2^{nd}$ grade)<br>Diagnosis method: biopsy and CT and ultrasonic scan | Name of subject: Mrs. Shu-Yuan Huang<br>Date of birth: Oct. 21, 1935<br>Address: Shiluo, Yunlin Hsien<br><br>Date of diagnosis: April. 1999<br>Place of hospital: Chiai Hsien, Taiwan<br>Diagnosis: hepatoma |
| Condition before trial: | Precedent treatments and results |
| Main cancer-related symptoms:<br>Pain of the right chest and costal region and swelling and occasional pain of abdomen<br>Other minor symptoms:<br>6 to 8 times of unsolidified stool, small amount of urination and cough<br>This subject has enrolled into this trial since Apr. 23, 1999 till Jul. 23, 1999 for a total of 7 courses and 84 days.<br>Trial procedure:<br>The medication combination, specific for treating hepatoma and pancreatic cancer, is taken within 90 minutes after meals, that is 3 times a day for a total of 12 gm.<br>On May 2, 1999, man symptoms were significantly alleviated and the minor symptoms were slightly improved.<br>On Jun. 12, 1999, main symptoms recurred but not as serious as previous. Till the end of trial, main symptoms were continuously improved. | Chemotherapy performed at the original hospital<br><br><br><br><br><br><br><br>Determination of efficiency: with efficiency<br>Filed on Mar. 15, 2002 |

| The practical subject in this clinical trial No. 60 ||
|---|---|
| Cancer type: pancreatic adenocarcinoma<br>Original number of case: 01011215 | Name of subject: Mrs. Ye Ge Chiu Huang<br>Date of birth: Sep. 10, 1911 |

-continued

| | |
|---|---|
| The hospital making diagnosis: Kaohsiung Ming-Sheng Hospital<br>Hospital grade: regional (the 2nd grade)<br>Diagnosis method: nuclear examination and CT and ultrasonic scan | Address: Chianjin District, Kaohsiung City<br><br>Date of diagnosis: January 2001<br>Place of hospital: Kaohsiung City, Taiwan<br>Diagnosis: pancreatic adenocarcinoma, CA19-9: 17200, CA72-4: 7.70 |
| Condition before trial: | Precedent treatments and results |
| Main cancer-related symptoms: abdominal swelling and pain, pain of the right costal region, and pain of inner side of the left leg with movement difficulty<br>Other minor symptoms:<br>Abnormal excretion and urination, lost of appetite, and occasional trace blood or lump in stool<br>This subject has enrolled into this trial since Jan. 21, 2001 till May 22, 2001 for a total of 6 courses and 72 days.<br>Trial procedure:<br>The medication combination, specific for treating hepatoma and pancreatic cancer, is taken within 90 minutes after meals, that is 3 times a day for a total of 12 gm.<br>On Feb. 15, 2001, stomach pain was significantly alleviated, able to walk and urination amounts increased.<br>On Mar. 7, 2001, stomach pain was further alleviated; pain of the right costal region reduced and pain of legs has vanished. The administration of trial medication was often discontinued due to certain reasons. During the trial period, main symptoms were continuously alleviated with the administration of medication. | Since the patient was old, alternative therapies, including diuretics and laxatives, were temporarily given by the hospital.<br><br><br><br><br><br><br><br><br><br>Determination of efficiency: with efficiency<br>Filed on Mar. 15, 2002 |

The practical subject in this clinical trial   No. 61

| | |
|---|---|
| Cancer type: hepatoma<br>Original number of case: 01101201<br>The hospital making diagnosis: Kaohsiung Chang Gung Hospital<br>Hospital grade: regional (the 2nd grade)<br>Diagnosis method: biopsy and CT and ultrasonic scan | Name of subject: Mr. Shui-Yuan Yang<br>Date of birth: Sep. 8, 1941<br>Address: Fengshan, Kaohsiung Hsien<br><br><br>Date of diagnosis: November 2000<br>Place of hospital: Kaohsiung Hsien, Taiwan<br>Diagnosis: a hepatoma of 2.4 cm, and pancreatic abnormality with a CA 19-9 of 57.02 and a higher hepatic index |
| Condition before trial: | Precedent treatments and results |
| Main cancer-related symptoms:<br>Abdominal swelling, occasional pain of the right costal region, swelling of shin and occasional pain at navel.<br>Other minor symptoms:<br>Tiredness and fatigue, dryness and bitterness of mouth, urination difficulty, and occasional bleeding of veins in stomach<br>This subject has enrolled into this trial since Oct. 12, 2001 till Dec. 6, 2001 for a total of 5 courses and 60 days.<br>Trial procedure:<br>The medication combination, specific for treating hepatoma and pancreatic cancer, is taken within 90 minutes after meals, that is 3 times a day for a total of 12 gm.<br>On Oct. 24, 2001, abdominal swelling and pain of the right costal region have vanished and swelling has alleviated.<br>On Nov. 4, 2001, all symptoms were further alleviated with a reduction of hepatic index. At the end of treatment, main symptoms were significantly alleviated with the vanishment of swelling and the shrunken of tumor mass from 2.4 cm to 1.6 cm. | After confirmation of diagnosis, alcohol chemotherapies were performed in the original hospital on and off till October 2001.<br><br><br><br><br><br><br><br><br><br>Determination of efficiency: significant efficiency<br>Filed on Mar. 15, 2002 |

The practical subject in this clinical trial   No. 62

| | |
|---|---|
| Cancer type: hepatoma<br>Original number of case: 97050102 | Name of subject: Mrs. Liu Zhi Ying Zhan<br>Date of birth: Jun. 6, 1919 |

-continued

| | |
|---|---|
| The hospital making diagnosis: Taichung Veteran General Hospital<br>Hospital grade: regional (the 2nd grade)<br>Diagnosis method: biopsy and CT and ultrasonic scan | Address: S. District, Tainan City<br><br>Date of diagnosis: April 1997<br>Place of hospital: Taichung City, Taiwan<br>Diagnosis: a hepatoma of 12.0 cm with an AFP of 268 and a higher hepatic index |
| Condition before trial: | Precedent treatments and results |
| Main cancer-related symptoms:<br>Pain of the right costal region, abdominal swelling, hunger without the desire to eat and yellowish urination<br>Other minor symptoms:<br>Tiredness and fatigue, insufficient strength, movement difficulty and lost of appetite<br>This subject has enrolled into this trial since May 1, 1997 till Feb. 27, 1998 for a total of 12 courses and 144 days.<br>Trial procedure:<br>The medication combination, specific for treating hepatoma and pancreatic cancer, is taken within 90 minutes after meals, that is 3 times a day for a total of 12 gm.<br>On May 31, 1997, pain of the right costal region was alleviated.<br>On Jun. 21, 1997, pain of the right costal region has vanished; abdominal swelling and appetite have improved.<br>On Aug. 26, 1997, after examination of Taichung Veteran General Hospital, hepatoma has been found to shrink with a normal AFP and she was able to help with the housework. | Due to senility, she was not willing to be through procedures of dissection, thrombosis or chemotherapy. Therefore she directly participated this trial.<br><br><br><br><br><br><br><br><br><br><br>Determination of efficiency: significant efficiency<br>Filed on Mar. 15, 2002 |

The practical subject in this clinical trial   No. 63

| | |
|---|---|
| Cancer type: intrahepatic bile duct cancer<br>Original number of case: 97110826<br>The hospital making diagnosis: Taipei Veteran General Hospital<br>Hospital grade: regional (the 2nd grade)<br>Diagnosis method: CT and ultrasonic scan | Name of subject: Mrs. Shi Mei yu Ge<br>Date of birth: Jun. 15, 1922<br>Address: Hsinchu, City, Hsinchu Hsien<br><br><br>Date of diagnosis: October 1997<br>Place of hospital: Taipei City, Taiwan<br>Diagnosis: intrahepatic bile duct cancer with a higher hepatic index |
| Condition before trial: | Precedent treatments and results |
| Main cancer-related symptoms:<br>Pain and swelling of the right costal region, abdominal swelling, jaundice and vomit<br>Other minor symptoms:<br>Weakness, insufficient strength, and accustomed constipation<br>This subject has enrolled into this trial since Nov. 8, 1997 till Mar. 4, 1998 for a total of 9 courses and 108 days.<br>Trial procedure:<br>The medication combination, specific for treating hepatoma and pancreatic cancer, is taken within 90 minutes after meals, that is 3 times a day for a total of 12 gm.<br>On Nov. 25, 1997, main symptoms were alleviated but still vomiting during taking the medication. Appetite was improved.<br>On Dec. 19, 1997, the vomit was stopped with better appetite and vitality, however, still with constipation. At the end of treatment, main symptoms were significantly alleviated and physical strength was gradually recovered. | Unknown<br><br><br><br><br><br><br><br><br><br><br><br>Determination of efficiency: with efficiency<br>Filed on Mar. 15, 2002 |

The practical subject in this clinical trial   No. 64

| | |
|---|---|
| Cancer type: pancreatic adenocarcinoma<br>Original number of case: 00062311<br>The hospital making diagnosis: Linko Chang Gung Hospital<br>Hospital grade: teaching (the 1st grade) | Name of subject: Mr. Wei-Ren Cheng<br>Date of birth: Oct. 25, 1966<br>Address: Tsztung, Yunlin Hsien |

-continued

| | |
|---|---|
| Diagnosis method: | Date of diagnosis: December 1999<br>Place of hospital: Taipei Hsien, Taiwan<br>Diagnosis: pancreatic adenocarcinoma |
| Condition before trial: | Precedent treatments and results |
| Main cancer-related symptoms:<br>Vomiting mucus at 1 hour after breakfast, abdominal swelling, diarrhea of 5 or 6 times in a day<br>Other minor symptoms:<br>Tiredness and fatigue, gasping and emaciation<br><br>This subject has enrolled into this trial since Jun. 23, 2000 till Aug. 5, 2000 for a total of 3 courses and 36 days.<br>Trial procedure:<br>The medication combination, specific for treating hepatoma and pancreatic cancer, is taken within 90 minutes after meals, that is 3 times a day for a total of 12 gm.<br>From Jun. 6, 2000, the beginning of this trial till the end of treatment, condition was merely maintained without deterioration. Main symptoms, vitality, and physical strength were not improved. | He was treated for diabetes at Chunghua Christian Hospital during 1996. Via scan at Chiai Christian Hospital and Zhushan Showchuan Hospital, unidentified objective was found. After angiography performed at Shalu Guang Tain Hospital, pancreatic adenocarcinoma was confirmed by Linko Chang Gung Hospital.<br><br><br><br><br><br>Determination of efficiency: inefficiency<br>Filed on Mar. 15, 2002 |

The practical subject in this clinical trial  No. 65

| | |
|---|---|
| Cancer type: hepatoma<br>Original number of case: 01030406<br>The hospital making diagnosis: Linko Chang Gung Hospital<br>Hospital grade: teaching (the 1$^{st}$ grade)<br>Diagnosis method: CT and ultrasonic scan | Name of subject: Mr. Jian Chuan Su<br>Date of birth: Oct. 1, 1947<br>Address: Gueishan, Taoyuan Hsien<br><br><br>Date of diagnosis: February 2000<br>Place of hospital: Taipei Hsien, Taiwan<br>Diagnosis: a small hepatoma was detected in February 2000. After chemotherapy and examined again in February, 2001, a hepatoma of 0.6 cm was detected. |
| Condition before trial: | Precedent treatments and results |
| Main cancer-related symptoms:<br>Occasional sudden pain and tightness of the right costal region, abdominal stuffiness and heartburn<br>Other minor symptoms:<br>Tiredness and fatigue, excretion of twice a day, and sleepiness<br>This subject has enrolled into this trial since Mar. 4, 2001 till Mar. 10, 2002 for a total of 28 courses and 346 days.<br>Trial procedure:<br>The medication combination, specific for treating hepatoma and pancreatic cancer, is taken within 90 minutes after meals, that is 3 times a day for a total of 12 gm.<br>On Mar. 20, 2001, main symptoms was alleviated and, during the following courses, main symptoms vasinshed or occasionally occurred but slightly.<br>On Apr. 7, 2001, CEA was 7.1, AFP was 16.25, CA19-9 51.20 and hepatic index was reduced.<br>On Jun. 1, 2001, CEA was 12.3, AFP was 15.23, CA19-9 was 54.9 and hepatic index was slightly elevated. On Sep. 21, 2001, CEA was 7.30, AFP was 12.66, and CA19-9 was 52.9. On Jan. 17, 2002, CEA was 6.0, AFP was 14.25 and CA19-9 was 21.9. | On Feb. 21, 2001, CEA was 7.83, AFP was 16.34, CA19-9 was 55.51 and hepatic indexes were too high.<br><br><br><br><br><br><br><br><br>Determination of efficiency: with efficiency<br>Filed on Mar. 15, 2002 |

The practical subject in this clinical trial  No. 66

| | |
|---|---|
| Cancer type: hepatoma<br>Original number of case: 00052501<br>The hospital making diagnosis: Gangshan Weishan General Hospital | Name of subject: Mrs. Chang Yue Li Zheng<br>Date of birth: Sep. 1, 1929<br>Address: Hunei, Kaohsiung Hsien |

-continued

| | |
|---|---|
| Hospital grade: general (the 3rd grade)<br>Diagnosis method: CT and ultrasonic scan | Date of diagnosis: May 3, 2000<br>Place of hospital: Kaohsiung Hsien, Taiwan<br>Diagnosis: 2 hepatomas of 4.0 cm and 1.0 cm, with lipidemia and a ALT/AST over 60 |
| Condition before trial: | Precedent treatments and results |
| Main cancer-related symptoms:<br>Tightness of the right costal region, abdominal swelling and acid retching<br>Other minor symptoms:<br>Sleepless, dizziness, constipation firstly and then diarrhea twice a day.<br>This subject has enrolled into this trial since May 25, 2000 till Aug. 31, 2000 for a total of 4 courses and 48 days.<br>Trial procedure:<br>The medication combination, specific for treating hepatoma and pancreatic cancer, is taken within 90 minutes after meals, that is 3 times a day for a total of 12 gm.<br>On Jul. 11, 2000, main symptoms were alleviated.<br>On Aug. 3, 2000, the hepatoma has shrunken from 4.0 cm to 2.0 cm and another hepatoma of 1.0 cm has vanished. Hepatic indexes and neutral fatty acid were normal. | After the medication of the original hospital with no efficiency, main symptoms were not improved, she participated this trial.<br><br>Determination of efficiency: significant efficiency<br>Filed on Mar. 15, 2002 |

| The practical subject in this clinical trial No. 67 ||
|---|---|
| Cancer type: hepatoma<br>Original number of case: 97090702<br>The hospital making diagnosis: National Cheng Gung University Hospital<br>Hospital grade: teaching (the 1st grade)<br>Diagnosis method: CT and ultrasonic scan | Name of subject: Mr. Ming Ho Liu<br>Date of birth: Oct. 27, 1931<br>Address: Yanshuei, Tainan Hsien<br><br>Date of diagnosis: December 1994<br>Place of hospital: Tainan City, Taiwan<br>Diagnosis: a hepatoma of 2.0 cm, which was deteriorated via the diagnosis of Kaohsiung Chang Gung Hospital in January 1997 |
| Condition before trial: | Precedent treatments and results |
| Main cancer-related symptoms:<br>Pain of the right lower costal region, diarrhea with more than 10 times in a day, back pain and ache and vomiting<br>Other minor symptoms:<br>Micturition of small amount, sleepless, tiredness and fatigue, weakness and insufficient strength, thirst and gasping<br>This subject has enrolled into this trial since Sep. 7, 1997 till Dec. 25, 1997 for a total of 7 courses and 84 days.<br>Trial procedure:<br>The medication combination, specific for treating hepatoma and pancreatic cancer, is taken within 90 minutes after meals, that is 3 times a day for a total of 12 gm.<br>In the initial stage of treatment, the condition was merely maintained without deterioration. At the end of treatment, main symptoms, vitality and physical strength were not improved at all. | Unknown, complicated with liver cirrhosis, diabetes, hypersensitivity of prostate<br><br>Determination of efficiency: inefficiency<br>Filed on Mar. 15, 1992 |

| The practical subject in this clinical trial No. 68 ||
|---|---|
| Cancer type: hepatoma<br>Original number of case: 99031012<br>The hospital making diagnosis: Taipei Veteran General Hospital<br>Hospital grade: regional (the 2nd grade)<br>Diagnosis method: biopsy and CT and ultrasonic scan | Name of subject: Mr. Shing Yun Liu<br>Date of birth: Apr. 4, 1943<br>Address: Shinfeng, Hsinchu Hsien<br><br>Date of diagnosis: Aug. 12, 1998<br>Place of hospital: Taipei Hsien, Taiwan<br>Diagnosis: hepatoma and liver cirrhosis |
| Condition before trial: | Precedent treatments and results |
| Main cancer-related symptoms:<br>Pain of the left and right costal region, abdominal | Surgery was performed at Taipei Veteran General Hospital in 1998 followed by chemotherapy with a |

-continued

| | |
|---|---|
| swelling and hard as stone, occasionally sharp pain of the waist and abdomen and numbness of limbs<br>Other minor symptoms:<br>Micturition of small amount, and sleepless<br>This subject has enrolled into this trial since Mar. 10, 1999 till Jul. 20, 1999 for a total of 7 courses and 84 days.<br>Trial procedure:<br>The medication combination, specific for treating hepatoma and pancreatic cancer, is taken within 90 minutes after meals, that is 3 times a day for a total of 12 gm.<br>After 2 courses of treatment, main symptoms were alleviated and the catheter for chemotherapy was removed. However, during the following courses, main symptoms recurred with no efficiency | normal AFP. At 120 days after, AFP was elevated again and tumor has metastasized into the spinal bone of waist and hip.<br><br><br><br><br><br>Determination of efficiency: inefficiency<br>Filed on Mar. 15, 2002 |

| The practical subject in this clinical trial No. 69 ||
|---|---|
| Cancer type: hepatoma<br>Original number of case: 99101304<br>The hospital making diagnosis: Linko Chang Gung Hospital<br>Hospital grade: teaching (the $1^{st}$ grade)<br>Diagnosis method: CT and ultrasonic scan | Name of subject: Mr. Yu-Lai Lai<br>Date of birth: Nov. 8, 1942<br>Address: Zhuolan, Miaoli Hsien<br><br><br>Date of diagnosis: June 1999<br>Place of hospital: Taipei Hsien, Taiwan<br>Diagnosis: multiple hepatoma with a radical pattern and the big one is of 5.6 cm |
| Condition before trial: | Precedent treatments and results |
| Main cancer-related symptoms:<br>Tightness of the right costal region, abdominal swelling with occasional pain and vomiting, small amount of urination<br>Other minor symptoms:<br>Diarrhea of 5 or 6 times in a day, tiredness and dizziness<br><br>This subject has enrolled into this trial since Oct. 13, 1999 till Apr. 5, 2000 for a total of 7 courses and 84 days.<br>Trial procedure:<br>The medication combination, specific for treating hepatoma and pancreatic cancer, is taken within 90 minutes after meals, that is 3 times a day for a total of 12 gm.<br>During the first course, main symptoms were alleviated and further improved during the second course.<br>On Jan. 5, 2000, via the scan before the $2^{nd}$ thrombosis procedure, the original cancer of 5.6 cm has vanished. On Mar. 1, 2000, this trial was resumed. From the scan at Taichung Ton General Hospital, cancer mass was merely a spot, eventually disappeared with an excellent condition.<br>Note: although the tumor mass has disappeared, before the surrounding pathology has eliminated, it was not cured. | After hospitalization at Linko Chang Gung Hospital, in June 1999, he has taken Chinese medicine. On Oct. 2, 1999, the first thrombosis procedure was performed in Taichung Ton General Hospital. After entering this trial, on January 5, the second thrombosis procedure was performed in Ton Surgical Hospital, and also decided to stay on this trial (blood vomiting occurred after the thrombosis procedure).<br><br><br><br><br>Determination of efficiency: significant efficiency<br>Filed on Mar. 15, 2002 |

| The practical subject in this clinical trial No. 70 ||
|---|---|
| Cancer type: hepatoma<br>Original number of case: 00072201<br>The hospital making diagnosis: Kaohsiung Veteran General Hospital<br>Hospital grade: regional (the $2^{nd}$ grade)<br>Diagnosis method: CT and ultrasonic scan | Name of subject: Mr. Ming-Jie Tsai<br>Date of birth: Jan. 4, 1935<br>Address: Chijin District, Kaohsiung City<br><br><br>Date of diagnosis: Jul. 20, 2000<br>Place of hospital: Kaohsiung City, Taiwan<br>Diagnosis: a hepatoma of 7.8 cm |
| Condition before trial: | Precedent treatments and results |
| Main cancer-related symptoms:<br>Jaundice with yellowish facial and body, abdominal swelling or pain and ache of waist and hip<br>Other minor symptoms:<br>Accustomed constipation, red-brownish urination, and lost of appetite | After a scan examination on Jul. 19, 2000, at Chung Gung Hospital, he transferred to Veteran General Hospital on July 20 and the diagnosis was reconfirmed. Doctors told the family that surgery was applicable for tumor smaller than 5 cm and he was not suitable for operation. Therefore, he asked to join |

|  |  |
| --- | --- |
| This subject has enrolled into this trial since Jul. 22, 2000 till Sep. 27, 2000 for a total of 4 courses and 48 days.<br>Trial procedure:<br>The medication combination, specific for treating hepatoma and pancreatic cancer, is taken within 90 minutes after meals, that is 3 times a day for a total of 12 gm.<br>During the 2$^{nd}$ course, jaundice has been greatly reduced and pain has vanished with a reduced hepatic index. The catheter was removed. Critical condition of hepatoma was surly relieved. Following treatment after the end of trial was unknown. | this trial. The bile catheter was implanted on July 24 at Veteran General Hospital.<br><br><br><br><br>Determination of efficiency: with efficiency<br>Filed on Mar. 15, 2002 |

| The practical subject in this clinical trial   No. 71 | |
| --- | --- |
| Cancer type: hepatoma<br>Original number of case: 99091104<br>The hospital making diagnosis: Linko Chang Gung Hospital<br>Hospital grade: teaching (the 1$^{st}$ grade)<br>Diagnosis method: CT and ultrasonic scan | Name of subject: Mr. Zhen Fu Tsai<br>Date of birth: Feb. 15, 1946<br>Address: Jungli City, Taoyuan Hsien<br><br><br>Date of diagnosis: Sep. 7, 1999<br>Place of hospital: Taipei Hsien, Taiwan<br>Diagnosis: hepatoma |
| Condition before trial: | Precedent treatments and results |
| Main cancer-related symptoms:<br>Abdominal swelling and stuffiness of the right costal region<br>Other minor symptoms:<br>Facial spots of while sediment, and normal urination and excretion<br>This subject has enrolled into this trial since Sep. 11, 1999 till Oct. 26, 1999 for a total of 4 courses and 48 days.<br>Trial procedure:<br>The medication combination, specific for treating hepatoma and pancreatic cancer, is taken within 90 minutes after meals, that is 3 times a day for a total of 12 gm.<br>On September 23, during the 1$^{st}$ course, main symptoms were eliminated without any recurrence after another 2 courses | Internal medication or other treatment of short term without any thrombosis or chemotherapy.<br><br><br><br><br><br><br><br><br><br><br>Determination of efficiency: significant efficiency<br>Filed on Mar. 15, 2002 |

| The practical subject in this clinical trial   No. 72 | |
| --- | --- |
| Cancer type: hepatoma<br>Original number of case: 98082202<br>The hospital making diagnosis: Kaohsiung Chang Gung Hospital<br>Hospital grade: regional (the 2$^{nd}$ grade)<br>Diagnosis method: CT and ultrasonic scan | Name of subject: Mr. Chian-Ming Tsai<br>Date of birth: Feb. 9, 1948<br>Address: Nantz District, Ksohsiung City<br><br>Date of diagnosis: April 1998<br>Place of hospital: Kaohsiung Hsien, Taiwan<br>Diagnosis: hepatoma |
| Condition before trial: | Precedent treatments and results |
| Main cancer-related symptoms:<br>Occasional pain of the right costal region<br>Other minor symptoms:<br>Tiredness and fatigue, gasping, sleepless, spontaneous sweating, spermatorrhea, skin itchiness and irritation<br>This subject has enrolled into this trial since Aug. 22, 1998 till Dec. 22, 1998 for a total of 5.5 courses and 66 days.<br>Trial procedure:<br>The medication combination, specific for treating hepatoma and pancreatic cancer, is taken within 90 minutes after meals, that is 3 times a day for a total of 12 gm.<br>On Sep. 3, 1998, during the 1$^{st}$ course, pain of the right costal region was alleviated and irritation was amended.<br>On Sep. 19, 1998, pain of the right costal region has vanished and minor symptoms were alleviated. | A thrombosis procedure was performed on Apr. 30, 1998 at Chung Gung Hospital and others were unknown.<br><br><br><br><br><br><br><br><br><br>Determination of efficiency: significant efficiency<br>Filed on Mar. 15, 2002 |

| | |
|---|---|
| Till Dec. 16, 1999, main symptoms were not recurred and minor symptoms were improved. | |

| The practical subject in this clinical trial No. 73 ||
|---|---|
| Cancer type: hepatoma<br>Original number of case: 97032026<br>The hospital making diagnosis: Kaohsiung Chang Gung Hospital<br>Hospital grade: regional (the 2$^{nd}$ grade)<br>Diagnosis method: CT and ultrasonic scan | Name of subject: Mr. Wen-Kui Hsien<br>Date of birth: Sep. 24, 1953<br>Address: Shigang, Tainan Hsien<br><br>Date of diagnosis: November, 1996<br>Place of hospital: Kaohsiung Hsien, Taiwan<br>Diagnosis: a hepatoma of 13.0 cm with a higher hepatic index and a higher AFP |
| Condition before trial: | Precedent treatments and results |
| Main cancer-related symptoms:<br>Pain of the lower right costal region, swelling and hardness of the left costal region, and abdominal swelling<br>Other minor symptoms:<br>Sciatica of the right leg, cough, diarrhea, spontaneous sweating and night sweat<br>This subject has enrolled into this trial since Mar. 20, 1997 till Jul. 26, 1997 for a total of 9 courses and 108 days.<br>Trial procedure:<br>The medication combination, specific for treating hepatoma and pancreatic cancer, is taken within 90 minutes after meals, that is 3 times a day for a total of 12 gm.<br>Main symptoms were alleviated at the initial stage with an elimination of sciatica of the right leg. Not much improvement was achieved in the following treatment. Apart from the disappearance of pain of the lower right costal region, the left costal region was still swelling with the deterioration of sciatica of the right leg (may due to the cancer metastasis). Not much improvement for the digestive system. The patient returned to Chang Gung for electrical treatment of the leg. The case was classified as not efficient. | Thrombosis procedures performed at Chang Gung Hospital<br><br><br><br><br><br><br><br><br><br>Determination of efficiency: inefficiency<br>Filed on Mar. 15, 2002 |

| The practical subject in this clinical trial No. 74 ||
|---|---|
| Cancer type: intrahepatic bile duct cancer<br>Original number of case: 99071701<br>The hospital making diagnosis: Kaohsiung Medical University Hospital<br>Hospital grade: teaching (the 1$^{st}$ grade)<br>Diagnosis method: CT and ultrasonic scan | Name of subject: Mr. Chian-Lai Zhong<br>Date of birth: Jun. 28, 1936<br>Address: Dashu, Kaohsiung Hsien<br><br>Date of diagnosis: Jun. 28, 1999<br>Place of hospital: Kaohsiung City, Taiwan<br>Diagnosis: intrahepatic bile duct cancer with hepatitis C |
| Condition before trial: | Precedent treatments and results |
| Main cancer-related symptoms:<br>Pain of lower right costal region, chest stuffiness, abdominal swelling, and swelling of shin<br>Other minor symptoms:<br>High fever, tiredness and fatigue, insufficient strength, loss of appetite, micturition and excretion difficulty<br>This subject has enrolled into this trial since Jul. 17, 1999 till Sep. 4, 1999 for a total of 4 courses and 48 days.<br>Trial procedure:<br>The medication combination, specific for treating hepatoma and pancreatic cancer, is taken within 90 minutes after meals, that is 3 times a day for a total of 12 gm.<br>High fever was eliminated on Jul. 21, 1999 and on Jul. 29, 1999, pain of the costal region was reduced with improved appetite and swelling.<br>On Aug. 14, 1999, main symptoms were alleviated with reduction in swelling but occasional acid retching.<br>At the end of treatment, main symptoms were | Chemotherapy at the original hospital<br><br><br><br><br><br><br><br><br><br><br><br>Determination of efficiency: with efficiency<br>Filed on Mar. 15, 2002 |

-continued disappeared or significantly improved and minor symptoms were also significantly improved.

| The practical subject in this clinical trial No. 75 ||
|---|---|
| Cancer type: hepatoma<br>Original number of case: 98020602<br>The hospital making diagnosis: National Chang Kung University Hospital<br>Hospital grade: teaching (the 1$^{st}$ grade)<br>Diagnosis method: CT and ultrasonic scan | Name of subject: Mr. Sin-Ji Yan<br>Date of birth: Jun. 11, 1923<br>Address: Lioujia, Tainan Hsien<br><br>Date of diagnosis: February 1998<br>Place of hospital: Tainan City, Taiwan<br>Diagnosis: a hepatoma of 7.5 cm, hepatitis B carrier, and hepatitis C carrier |
| Condition before trial: | Precedent treatments and results |
| Main cancer-related symptoms:<br>Ache of the right neck and bone joint, chest stuffiness and excretion right after meal<br>Other minor symptoms:<br>Dizziness and lost of appetite<br><br>This subject has enrolled into this trial since Feb. 6, 1998 till Oct. 23, 1998 for a total of 7 courses and 84 days.<br>Trial procedure:<br>The medication combination, specific for treating hepatoma and pancreatic cancer, is taken within 90 minutes after meals, that is 3 times a day for a total of 12 gm.<br>On Feb. 12, 1998, main symptoms were improved and the diarrhea was recovered.<br>On Mar. 4, 1998, main symptoms were alleviated or recovered. Although the efficient was significant, this case did not fulfill the requirement due to the short period of trial.<br>On Aug. 18, 1998, after the additional 5 courses, main symptoms were not improved, as well as the vitality and strength, especially the excretion right after meal. | After the confirmation of diagnosis, he joined this trial with efficiency. After unknown treatment, he resumed this treatment on Aug. 18, 1998. The tumor size in March 1998 was 6.5 cm via scan at Chang Gung and was 9.0 cm in July 1998 via scan at National Chang Kung University Hospital<br><br><br><br><br><br>Determination of efficiency: inefficiency<br>Filed on Mar. 15, 2002 |

| The practical subject in this clinical trial No. 76 ||
|---|---|
| Cancer type: hepatoma<br>Original number of case: 01086401<br>The hospital making diagnosis: Taipei Veteran General Hospital<br>Hospital grade: regional (the 2$^{nd}$ grade)<br>Diagnosis method: CT and ultrasonic scan | Name of subject: Mrs. Yu-Chian Su<br>Date of birth: May 2, 1934<br>Address: Chungshan District, Taipei City<br><br>Date of diagnosis: June 1999<br>Place of hospital: Taipei Hsien, Taiwan<br>Diagnosis: hepatoma, liver cirrhosis, vesicles in pancreas and kidney hypofunction |
| Condition before trial: | Precedent treatments and results |
| Main cancer-related symptoms:<br>Occasional pain of the right costal region and abdomen, tenderness of stomach and pain while hungry, respiration difficulty, chest stuffiness, edema and swelling of shin<br>Other minor symptoms:<br>Tiredness and weakness, lost of appetite, difficulty in excretion and urination<br>This subject has enrolled into this trial since Aug. 4, 2001 till Sep. 8, 2001 for a total of 3 courses and 36 days.<br>Trial procedure:<br>The medication combination, specific for treating hepatoma and pancreatic cancer, is taken within 90 minutes after meals, that is 3 times a day for a total of 12 gm.<br>On Aug. 16, 2001, after the 1$^{st}$ course, via scan at Taian Hospital, the metastasized tumor has dispersed with normal GOT/GTP. Vesicles in pancreas were blurred due to exudates and kidney function did not deteriorate.<br>On Aug. 26, 2001, main symptoms were significantly alleviated with the gradual dispersion of | After being diagnosed at Veteran General Hospital, she was transferred to Taipei Taian Hospital for unknown treatment.<br><br><br><br><br><br><br><br><br><br>Determination of efficiency: significant efficiency<br>Filed on Mar. 15, 2002 |

| -continued | |
|---|---|
| edema and swelling. The tumor of 2.0 cm at the right liver lobe has dispersed, which indicated the significant efficiency of this trial. However, other treatments performed by the original hospital after such amazing improvement of condition, as well as the weakness of patient, have acted against the "surrounding pathology". The injection of plasma, preparation of high protein has resulted in the high pressure of portal vein and then led to hepatic coma. | |

| The practical subject in this clinical trial No. 77 | |
|---|---|
| Cancer type: hepatoma<br>Original number of case: 98050116<br>The hospital making diagnosis: Kaohsiung Chang Gung Hospital<br>Hospital grade: regional (the $2^{nd}$ grade)<br>Diagnosis method: biopsy and CT and ultrasonic scan | Name of subject: Mrs. Huang-Ye Gong<br>Date of birth: Oct. 10, 1929<br>Address: Linyuan, Kaohsiung Hsien<br><br>Date of diagnosis: Apr. 28, 1998<br>Place of hospital: Kaohsiung Hsien, Taiwan<br>Diagnosis: multifocal hepatoma (previous rectal cancer was dissected years ago with a normal CEA; all symptoms were referred to be related to hepatoma) |
| Condition before trial: | Precedent treatments and results |
| Main cancer-related symptoms:<br>Stomach swelling and hardness, local swelling or pain, skin itchiness, and swelling of shin<br>Other minor symptoms:<br>Accustomed constipation with once in 2 or 3 days, weakness of legs, potential sprain and occasional urethritis<br>This subject has enrolled into this trial since May 1, 1998 till Dec. 13, 1998 for a total of 12 courses and 144 days.<br>Trial procedure:<br>The medication combination, specific for treating hepatoma and pancreatic cancer, is taken within 90 minutes after meals, that is 3 times a day for a total of 12 gm.<br>On May 13, 1998, during the course, main symptoms were alleviated with gradual dispersion of swelling and vanishment of itchiness.<br>On Jun. 13, 1998, all symptoms were alleviated with the regression of tumor to about 1/2.<br>At the end of treatment, all symptoms were still alleviated but swelling of abdomen and shin was not completely dispersed. | Determination of efficiency: with efficiency<br>Filed on Mar. 15, 2002 |

What is claimed is:

1. A medication combination for treating hepatoma and pancreatic cancer, comprising Baizhu, Danggui, Hanxincao, Huotanmucao, Ainaxiang, Shuodiao, Malan, Ludou, Canger, Daqinggen, Banbianlian, Xingren, Nuzhenzi, Qianhu, Jiatonghao, Yinchenhao, Yujin, Zhishi, and Banxia.

2. The medication combination of claim 1, wherein the combination comprises 3–7% of Baizhu, 3–7% of Danggui, 4–8% of Hanxincao, 2–6% of Huotanmucao, 2–6% of Ainaxiang, 5–9% of Shuodiao, 6–10% of Malan, 5–9% of Ludou, 3–7% of Canger, 4–8% of Daqinggen, 3–7% of Banbianlian, 2–6% of Xingren, 4–8% of Nuzhenzi, 3–7% of Qianhu, 3–7% of Jiatonghao, 3–7% of Yinchenhao, 3–7% of Yujin, 2–6% of Zhishi, and 2–6% of Banxia.

3. The medication combination of claim 2, wherein the combination comprises 5% of Baizhu, 5% of Danggui, 6% of Hanxincao, 4% of Huotanmucao, 4% of Ainaxiang, 7% of Shuodiao, 8% of Malan, 7% of Ludou, 5% of Canger, 6% of Daqinggen, 5% of Banbianlian, 4% of Xingren, 6% of Nuzhenzi, 5% of Qianhu, 5% of Jiatonghao, 5% of Yinchenhao, 5% of Yujin, 5% of Zhishi, and 4% of Banxia.

4. The medication combination of claim 1 further comprising Fuling as a form of powder.

\* \* \* \* \*